(12) United States Patent
Love et al.

(10) Patent No.: US 10,987,636 B2
(45) Date of Patent: Apr. 27, 2021

(54) FILTRATION SYSTEMS AND METHODS FOR MANUFACTURING BIOLOGICALLY-PRODUCED PRODUCTS

(71) Applicant: Massachusetts Institute of Technology, Cambridge, MA (US)

(72) Inventors: J. Christopher Love, Somerville, MA (US); Craig A. Mascarenhas, Brookline, MA (US); Amos Enshen Lu, Cambridge, MA (US); Richard Dean Braatz, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 127 days.

(21) Appl. No.: 16/120,200

(22) Filed: Aug. 31, 2018

(65) Prior Publication Data

US 2019/0070564 A1   Mar. 7, 2019

Related U.S. Application Data

(60) Provisional application No. 62/553,104, filed on Aug. 31, 2017.

(51) Int. Cl.
*B01D 63/04* (2006.01)
*B01D 69/08* (2006.01)
(Continued)

(52) U.S. Cl.
CPC ............ *B01D 69/081* (2013.01); *B01D 63/02* (2013.01); *B01D 63/024* (2013.01); *B01D 63/04* (2013.01);
(Continued)

(58) Field of Classification Search
None
See application file for complete search history.

(56) References Cited

U.S. PATENT DOCUMENTS 4,781,832 A * 11/1988 Takemura .............. B01D 63/02
                                                  210/321.8
5,019,512 A    5/1991 Varecka et al.
(Continued)

FOREIGN PATENT DOCUMENTS

EP          1170052 A1    1/2002
WO   WO 2014/137903 A2    9/2014
(Continued)

OTHER PUBLICATIONS

Mascarenhas, Design and Development of Components of a Modular Bioreactor. MIT Thesis. Master of Science in Mechanical Engineering. Available to the public Dec. 5, 2017 208 pages.
(Continued)

*Primary Examiner* — Chester T Barry
(74) *Attorney, Agent, or Firm* — Wolf, Greenfield & Sacks, P.C.

(57) ABSTRACT

Aspects of the present disclosure relate to filtration systems and methods for production of biologically-produced products, which may include pharmaceutical and/or protein products. Certain biomanufacturing systems described herein comprise a bioreactor (e.g., a perfusion bioreactor, a chemostat) and a filter probe comprising a filter bundle comprising a plurality of hollow fibers (e.g., longitudinally aligned hollow fibers). According to some embodiments, a center-to-center distance between any two hollow fibers within the fiber bundle at one or more points along a length of the fiber bundle is relatively large (e.g., greater than or equal to an average outer diameter of the hollow fibers of the fiber bundle, greater than or equal to 1.1 times a minimum diameter of the two hollow fibers). In some embodiments, the hollow fibers within the fiber bundle are arranged in an array (e.g., a hexagonal, linear, annular, or square array).

20 Claims, 15 Drawing Sheets

(51) Int. Cl.
 C12M 1/00 (2006.01)
 B01D 69/02 (2006.01)
 B01D 63/02 (2006.01)
(52) U.S. Cl.
 CPC .............. *B01D 69/02* (2013.01); *C12M 29/04* (2013.01); *C12M 29/10* (2013.01); *C12M 47/10* (2013.01); *B01D 2313/14* (2013.01); *B01D 2319/025* (2013.01); *B01D 2325/02* (2013.01); *B01D 2325/20* (2013.01)

(56) References Cited

U.S. PATENT DOCUMENTS

| | | | |
|---|---|---|---|
| 5,626,734 | A | 5/1997 | Docoslis et al. |
| 5,783,083 | A * | 7/1998 | Henshaw ............... B01D 61/18 210/636 |
| 5,840,230 | A | 11/1998 | Geleff et al. |
| 6,544,788 | B2 | 4/2003 | Singh |
| 7,923,227 | B2 * | 4/2011 | Hickey .................. C12M 21/12 435/136 |
| 8,383,397 | B2 | 2/2013 | Wojciechowski et al. |
| 9,109,193 | B2 | 8/2015 | Galliher et al. |
| 9,427,699 | B2 * | 8/2016 | Mayer .................... B01D 53/22 |
| 2001/0027951 | A1 * | 10/2001 | Gungerich ............. B01D 65/02 210/636 |
| 2003/0159988 | A1 * | 8/2003 | Daigger .................. C02F 3/006 210/605 |
| 2009/0042253 | A1 | 2/2009 | Hiller |
| 2009/0301959 | A1 * | 12/2009 | Tada ..................... B01D 63/021 210/321.87 |
| 2011/0117538 | A1 | 5/2011 | Niazi |
| 2011/0315055 | A1 * | 12/2011 | Soma ..................... B01D 53/64 110/203 |
| 2011/0315625 | A1 | 12/2011 | Keenan et al. |
| 2013/0197200 | A1 | 8/2013 | Bian et al. |
| 2017/0114381 | A1 | 4/2017 | Goudar et al. |
| 2019/0070564 | A1 * | 3/2019 | Love ..................... B01D 63/024 |

FOREIGN PATENT DOCUMENTS

| | | |
|---|---|---|
| WO | WO 2015/166083 A1 | 11/2015 |
| WO | PCT/US2018/025582 | 3/2018 |
| WO | WO 2018/183848 A8 | 10/2018 |
| WO | WO 2018/183971 A1 | 10/2018 |
| WO | WO 2018/183972 A2 | 10/2018 |

OTHER PUBLICATIONS

Roth et al., Vortex flow filtration for cell separation in bioreactor operations. Ch. 2 in Membrane Separations in Biotechnology. Wang, Ed. New York: Marcel Dekker, Inc. Jan. 2001; 63-83.
Schiraldi et al., High cell density cultivation of probiotics and lactic acid production. Biotechnology and Bioengineering. Apr. 20, 2003; 82(2):213-222.
Seamans et al., Kinetics of growth and antibody production by a hybridoma cell line in a perfusion culture. Journal of Fermentation and Bioengineering. Dec. 1990; 70(4):241-245.
Voisard et al., Potential of cell retention techniques for large-scale high—density perfusion culture of suspended mammalian cells. Biotechnology and Bioengineering. Jun. 30, 2003; 82(7):751-765.
Xenopoulos, A new, integrated, continuous purification process template for monoclonal antibodies: Process modeling and cost of goods studies. Journal of Biotechnology. May 8, 2015; 213:42-53.
PCT/US2018/025582, Aug. 29, 2018, International Search Report and Written Opinion.
International Search Report and Written Opinion dated Aug. 29, 2018 for International Application No. PCT/US2018/025582.
[No Author Listed]. Continuous chromatography in downstream processing of a monoclonal antibody. GE Healthcare. Application Note, 29170800 AA. Oct. 2015 https://www.gelifesciences.co.jp/catal/og/pdf/AKTApccAN_1.PDF [last accessed May 2, 2018].
[No Author Listed]. Webinar: Flow Through Chromatography and Adsorptive Depth Filtration for Continuous Processing I Merck Website. May 24, 2016. https://www.merckmillipore.com/NL/en/20160516_171642?ReferrerURL=https://www.google.com/ [last accessed Jun. 26, 2018]. 8 pages.
Belfort et al., The behavior of suspensions and macromolecular solutions in crossflow microfiltration. Journal of Membrane Science. Nov. 28, 1994; 96(1-2):1-58.
Carstensen et al., In situ product recovery: Submerged membranes vs. external loop membranes. Journal of Membrane Science. Mar. 15, 2012; 394-395:1-36. Epub Dec. 7, 2011.
Carstensen et al., Reverse-flow diafiltration for continuous in situ product recovery. Journal of Membrane Science. Dec. 1, 2012; 421-422:39-50. Epub Jun. 30, 2012.
Clincke et al., Very high density of CHO cells in perfusion by ATF or TFF in WAVE bioreactor. Part I. Effect of the cell density on the process. Biotechnology Progress. May 21, 2013; 29(3):754-767.
Cunha et al., Methanol induction optimization for scFv antibody fragment production in *Pichia pastoris*. Biotechnology and Bioengineering. May 20, 2004; 86(4):458-467. Epub Mar. 30, 2004.
Konstantinov et al., White paper on continuous bioprocessing. Continuous Manufacturing Symposium. May 20-21, 2014. Journal of Pharmaceutical Sciences. Mar. 2015; 104(3):813-820. Epub Nov. 21, 2014.
PCT/US2018/025582, Oct. 10, 2019, International Preliminary Report on Patentability.
PCT/US2018/025582, Jul. 6, 2018, Invitation to Pay Additional Fees.
PCT/US2018/049281, Oct. 7, 2019, International Search Report and Written Opinion.
PCT/US2018/049281, Mar. 12, 2020, International Preliminary Report on Patentability.
PCT/US2018/049281, Aug. 13, 2019, Invitation to Pay Additional Fees.
International Preliminary Report on Patentability dated Oct. 10, 2019 for International Application No. PCT/US2018/025582.
Invitation to Pay Additional Fees dated Jul. 6, 2018 for International Application No. PCT/US2018/025582.
International Search Report and Written Opinion dated Oct. 7, 2019 for International Application No. PCT/US2018/049281.
International Preliminary Report on Patentability dated Mar. 12, 2020 for International Application No. PCT/US2018/049281.
Invitation to Pay Additional Fees dated Aug. 13, 2019 for International Application No. PCT/US2018/049281.

* cited by examiner

FILTRATION SYSTEMS AND METHODS FOR MANUFACTURING BIOLOGICALLY-PRODUCED PRODUCTS

RELATED APPLICATIONS

This application claims priority under 35 U.S.C. § 119(e) to U.S. Provisional Patent Application Ser. No. 62/553,104, filed Aug. 31, 2017, and entitled "Filtration Systems and Methods for Manufacturing Biologically-Produced Products," which is incorporated herein by reference in its entirety for all purposes.

GOVERNMENT FUNDING

This invention was made with Government support under Grant No. N66001-13-C-4025 awarded by the Space and Naval Warfare Systems. The Government has certain rights in the invention.

FIELD

The present invention generally relates to filtration systems and methods for manufacturing biologically-produced products.

BACKGROUND

Biologically-produced products, including therapeutic drugs produced by biological organisms, have revolutionized the pharmaceutical industry. Biological organisms are an attractive source of therapeutic drugs because they are often capable of producing molecules that would be challenging, if not impossible, to synthesize chemically. For example, some biological organisms can be engineered to produce complex proteins, such as antibodies and signaling proteins, which can be used to treat or prevent diseases ranging from cancer to rheumatoid arthritis.

Certain methods of manufacturing biologically-produced products involve substantially continuously-operated bioreactors (e.g., perfusion bioreactors, chemostats). Under substantially continuous operation of a bioreactor, a portion of the contents of the bioreactor may be pumped out of the bioreactor through one or more filters. However, conventional filters may adversely affect the biological health of cells, may be ineffective in filtering high-density cell cultures, and/or may be susceptible to membrane fouling. Accordingly, improved filtration systems for continuously-operated bioreactors are needed.

SUMMARY

The present invention generally relates to filtration systems and methods for manufacturing biologically-produced products. The subject matter of the present invention involves, in some cases, interrelated products, alternative solutions to a particular problem, and/or a plurality of different uses of one or more systems and/or articles.

Certain aspects relate to a filter probe. In some embodiments, the filter probe comprises a fiber bundle comprising a plurality of longitudinally aligned hollow fibers. In certain embodiments, a center-to-center distance between any two hollow fibers within the fiber bundle at one or more points along a length of the fiber bundle is greater than or equal to an average outer diameter of the hollow fibers of the fiber bundle.

In some embodiments, a filter probe comprises a fiber bundle comprising a plurality of longitudinally aligned hollow fibers. In certain embodiments, a center-to-center distance between any two hollow fibers within the fiber bundle at one or more points along a length of the fiber bundle is greater than or equal to 1.1 times a minimum diameter of the two hollow fibers.

In some embodiments, the filter probe comprises a fiber bundle comprising a plurality of hollow fibers. In certain embodiments, a center-to-center distance between any two hollow fibers within the fiber bundle at one or more points along a length of the fiber bundle is greater than or equal to an average outer diameter of the hollow fibers of the fiber bundle.

In some embodiments, a filter probe comprises a fiber bundle comprising a plurality of hollow fibers. In certain embodiments, a center-to-center distance between any two hollow fibers within the fiber bundle at one or more points along a length of the fiber bundle is greater than or equal to 1.1 times a minimum diameter of the two hollow fibers.

In some embodiments, a filter probe comprises a structured segment comprising at least a first region and a second region. In certain embodiments, each region comprises a hollow fiber bundle or a portion of a length of a hollow fiber bundle. In certain embodiments, at least a first hollow fiber of the hollow fiber bundle located in the first region of the structured segment is not longitudinally aligned with a second hollow fiber of the hollow fiber bundle located in the first region or the second region of the structured segment.

In some embodiments, a filter probe comprises a fiber bundle comprising a plurality of hollow fibers. In some embodiments, the filter probe further comprises a secondary filter. In certain embodiments, at least one hollow fiber of the fiber bundle is fluidically connected to the secondary filter.

In some embodiments, a filter probe comprises a fiber bundle comprising a plurality of hollow fibers. In certain embodiments, the filter probe is configured to rotate at a speed of at least about 10 RPM.

Certain aspects relate to a system. In some embodiments, the system comprises a bioreactor comprising a reaction chamber. In some embodiments, the system comprises a filter probe. In certain embodiments, the filter probe comprises a fiber bundle comprising a plurality of longitudinally aligned hollow fibers. In certain embodiments, a center-to-center distance between any two hollow fibers within the fiber bundle at one or more points along a length of the fiber bundle is greater than or equal to an average outer diameter of the hollow fibers of the fiber bundle.

In some embodiments, a system comprises a bioreactor comprising a reaction chamber. In some embodiments, the system comprises a filter probe. In certain embodiments, the filter probe comprises a fiber bundle comprising a plurality of longitudinally aligned hollow fibers. In certain embodiments, a center-to-center distance between any two hollow fibers within the fiber bundle at one or more points along a length of the fiber bundle is greater than or equal to 1.1 times a minimum diameter of the two hollow fibers.

Certain aspects relate to a method of producing at least one biologically-produced product. In some embodiments, the method comprises supplying at least one feed stream comprising at least one cell culture medium to a bioreactor at a first flow rate. In some embodiments, the method comprises producing, within the bioreactor, a suspension comprising the at least one cell culture medium and at least a first type of biological cells expressing the at least one biologically-produced product. In some embodiments, the method comprises causing at least a portion of the suspension to flow through a filter probe at a second flow rate to produce at least one filtrate stream. In certain embodiments, the filter probe comprises a fiber bundle comprising a plurality of longitudinally aligned hollow fibers. In certain embodiments, the second flow rate is at least about 0.5 reactor volumes per day.

Certain aspects relate to a method of harvesting at least one biologically-produced product from a bioreactor. In some embodiments, the method comprises producing, within the bioreactor, a suspension. In some embodiments, the method comprises causing at least a portion of a suspension contained within the bioreactor and comprising at least one cell culture medium and at least a first type of biological cells expressing the at least one biologically-produced product to flow through a hollow fiber filter probe at a flow rate of at least about 0.5 reactor volumes per day to produce at least one filtrate stream lean in the first type of biological cells. In certain embodiments, the filter probe has a diameter of about 25 mm or less.

In some embodiments, a method comprises flowing a cell suspension stream comprising at least one biologically-produced product and biological cells through a first region of a hollow fiber to produce a first filtrate stream in a lumen of the hollow fiber comprising the at least one biologically-produced product and lean in biological cells relative to the cell suspension stream. In some embodiments, the method further comprises directing the first filtrate stream to flow through the lumen of the hollow fiber from the first region to a second region. In some embodiments, the method further comprises directing the first filtrate stream to flow through the second region of the hollow fiber from the lumen to an interior region of a filter housing to produce a second filtrate stream.

Certain aspects relate to a kit. In some embodiments, the kit comprises a filter probe comprising a fiber bundle comprising a plurality of longitudinally aligned hollow fibers, wherein a center-to-center distance between any two hollow fibers within the fiber bundle at one or more points along a length of the fiber bundle is greater than or equal to an average outer diameter of the hollow fibers of the fiber bundle. In some embodiments, the kit comprises a storage container.

In some embodiments, a kit comprises a filter probe comprising a fiber bundle comprising a plurality of longitudinally aligned hollow fibers, wherein a center-to-center distance between any two hollow fibers within the fiber bundle at one or more points along a length of the fiber bundle is greater than or equal to 1.1 times a minimum diameter of the two hollow fibers. In some embodiments, the kit comprises a storage container.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
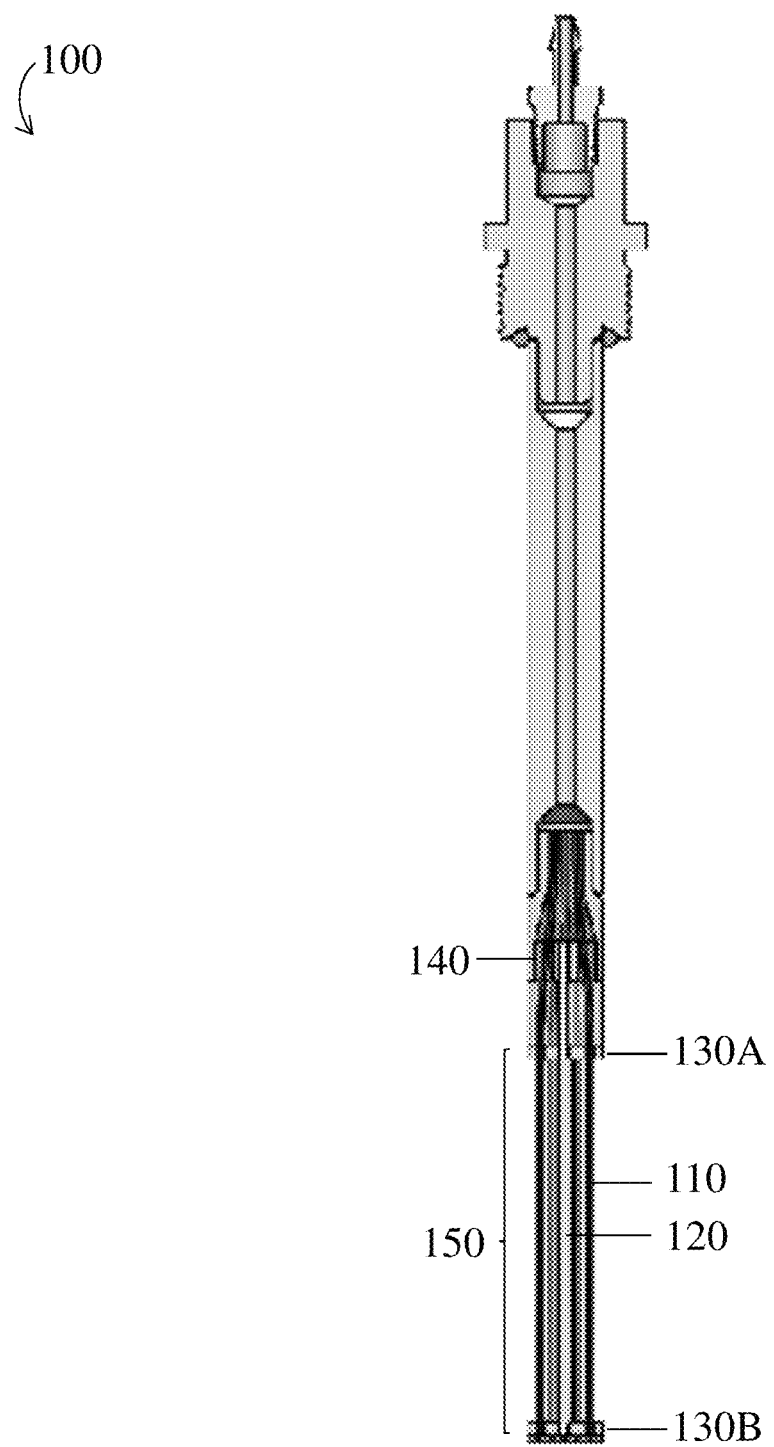
FIG. 1 is a schematic cross-sectional illustration of an exemplary filter probe, according to some embodiments.

Aspects of the present disclosure relate to filtration systems and methods for production of biologically-produced products, which may include pharmaceutical and/or protein products. Certain biomanufacturing systems described herein comprise a bioreactor (e.g., a perfusion bioreactor, a chemostat) and a filter probe comprising a filter bundle comprising a plurality of hollow fibers (e.g., longitudinally aligned hollow fibers). According to some embodiments, a center-to-center distance between any two hollow fibers within the fiber bundle at one or more points along a length of the fiber bundle is relatively large (e.g., greater than or equal to an average outer diameter of the hollow fibers of the fiber bundle, greater than or equal to 1.1 times a minimum diameter of the two hollow fibers). In some embodiments, the hollow fibers within the fiber bundle are arranged in an array (e.g., a hexagonal, linear, annular, or square array).

In some cases, it may be advantageous to operate a bioreactor under substantially continuous or semi-continuous conditions (e.g., continuous conditions temporarily interrupted by periods of non-operation). For example, compared to a fed-batch reactor (e.g., a bioreactor in which cells, media, and biologically-produced products remain in the bioreactor until the end of a run), a continuously-operated bioreactor may result in higher cell concentrations and product yields, lower levels of accumulated waste, immediate availability and reduced degradation (e.g., oxidation, aggregation, deamidation, proteolysis) of target biologically-produced products, and more consistent expression profiles. In order to facilitate substantially continuous or semi-continuous operation of a bioreactor, the bioreactor may be fluidically connected (e.g., directly fluidically connected) to a filter probe configured to filter at least a portion of the contents of the bioreactor.

As the inventors have recognized, however, there are often challenges associated with filtering bioreactor contents. For example, the bioreactor may contain a high-density cell culture that may become viscous and difficult to circulate. Conventional efforts to increase circulation (and thereby promote flow through a filter) through rigorous agitation may adversely affect the biological health of the cells and may even induce lysis and/or undesired transformations of the target biologically-produced product. In addition, other disadvantages have been associated with conventional single-membrane filters and conventional hollow-fiber filters. For example, conventional single-membrane filters may have low flow rates and/or may be susceptible to membrane fouling due to cellular debris, while conventional hollow-fiber filters may have poor circulation in the interior regions, which may reduce the effective surface area of the filter. The exposed hollow fibers of some conventional hollow-fiber filters have also been known to shear under high agitation during attempts to de-foul their surfaces, rendering them ineffective as filters.

The inventors have surprisingly recognized that some of these challenges may be overcome by a filter probe comprising a fiber bundle in which a plurality of hollow fibers (e.g., longitudinally aligned hollow fibers) are spaced such that a center-to-center distance between any two hollow fibers is relatively large (e.g., greater than or equal to an average outer diameter of the hollow fibers of the fiber bundle, greater than or equal to 1.1 times a minimum diameter of the two hollow fibers). Compared to a single-membrane filter probe occupying a certain volume, a hollow fiber filter probe occupying the same volume generally has a higher effective surface area and, therefore, a higher flow rate. In addition, the relatively large center-to-center distances between the hollow fibers of the fiber bundle may advantageously promote circulation within the interior regions of the filter probe.

In some cases, a filter probe comprising a plurality of hollow fibers with relatively large center-to-center distances may be compatible with a wide range of bioreactors (e.g., bioreactors with top ports, bioreactors with side ports). In some instances, at least a portion of the filter probe may have a sufficiently small diameter to pass through a bioreactor port. Accordingly, the filter probe may permit a wide range of bioreactors to be adapted to operate in perfusion and/or chemostat modes (e.g., by adding the filter probe in a standard port and incorporating a pump).

In certain cases, a filter probe positioned within a bioreactor may be associated with certain advantages compared to an external filter (e.g., an externally-mounted hollow fiber probe comprising voluminous loops of fibers at one end of the probe). As an illustrative example, bioreactors often use agitators and/or impellers to maintain a sufficiently high level of dissolved oxygen within a cell culture, and, in some instances, shear forces generated by those agitators and/or impellers may de-foul an in-vessel filter probe. In some cases, the ability of an in-vessel filter probe to be de-fouled by those shear forces may advantageously avoid the need for additional system components (e.g., pumps) or additional expenditures of energy or other resources. In addition, external filters may require extended residence times outside a bioreactor, which may lead to reduced cell viabilities and/or lysis (e.g., due to lack of oxygen). Assembly of one or more external filters may also create additional points of potential contamination. Additionally, while certain types of external filters (e.g., alternating tangential flow membrane filters, tangential flow filtration membrane filters) may seek to minimize membrane fouling by having a significant amount of crossflow across the filtration membranes, high shear within the crossflow-generating pump may lead to degradation of biologically-produced products.

A cross-sectional schematic diagram of an exemplary filter probe is illustrated in FIG. 1. As shown in FIG. 1, filter probe 100 comprises a fiber bundle comprising a plurality of longitudinally aligned hollow fibers 110. In addition to hollow fibers 110, filter probe 100 may further comprise central shaft 120, first spacing element 130A, second spacing element 130B, and end piece 140. In some embodiments, spacing elements 130A and 130B may be configured to maintain a certain distance between hollow fibers 110. For example, each of spacing elements 130A and 130B may comprise a plurality of clearance holes through which hollow fibers 110 can pass. In some instances, structured segment 150 (e.g., a segment of filter probe 100 over which hollow fibers 110 are exposed to the external environment and have relatively large center-to-center distances) may extend from first spacing element 130A to second spacing element 130B. In some embodiments, any portions of hollow fibers 110 extending beyond second spacing element 130B may be sealed (e.g., through potting) to prevent fluids from entering the central cavities (i.e., lumens) of hollow fibers 110 through the ends of the hollow fibers. Within structured segment 150, a center-to-center distance between any two hollow fibers 110 may be greater than or equal to an average outer diameter (OD) of hollow fibers 110 and/or may be greater than or equal to 1.1 times a minimum diameter of the two hollow fibers.

Figure 2:
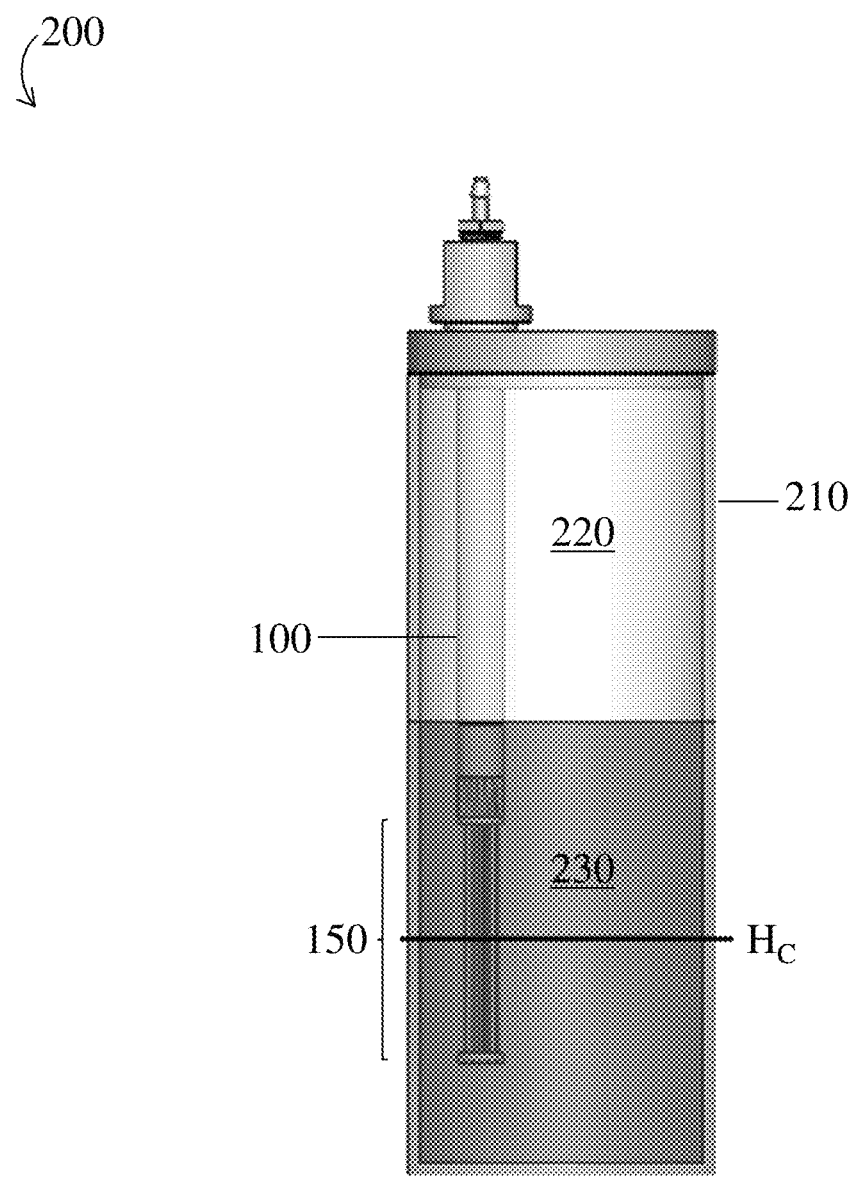
FIG. 2 is, according to some embodiments, a schematic illustration of a system comprising a bioreactor and a filter probe.

A schematic illustration of exemplary system 200 comprising filter probe 100 and bioreactor 210 is shown in FIG. 2. As shown in FIG. 2, bioreactor 210 comprises reaction chamber 220, which contains suspension 230. In some embodiments, bioreactor 210 may be configured to promote the growth and maintenance of a first type of biological cells configured to express at least one biologically-produced product. In some instances, suspension 230 comprises a cell culture medium (e.g., a growth cell culture medium configured to promote growth of the first type of biological cells, a production cell culture medium configured to promote expression of the at least one biologically-produced product) and the first type of biological cells.

In some embodiments, filter probe 100 may be fluidically connected (e.g., directly fluidically connected) to bioreactor 210. For example, as shown in FIG. 2, filter probe 100 may be at least partially submerged in suspension 230. In some instances, filter probe 100 may be positioned in suspension 230 such that a center point along the length of structured segment 150 is aligned with a center point along the height of suspension 230 (indicated with an "Hc" in FIG. 2). In some embodiments, filter probe 100 may be configured to allow at least a portion of suspension 230 to flow through filter probe 100. In certain instances, at least a portion of the cell culture medium may flow through filter probe 100 as a filtrate, while at least a portion of the biological cells may be retained within reaction chamber 220 as a retentate.

Figure 3A:
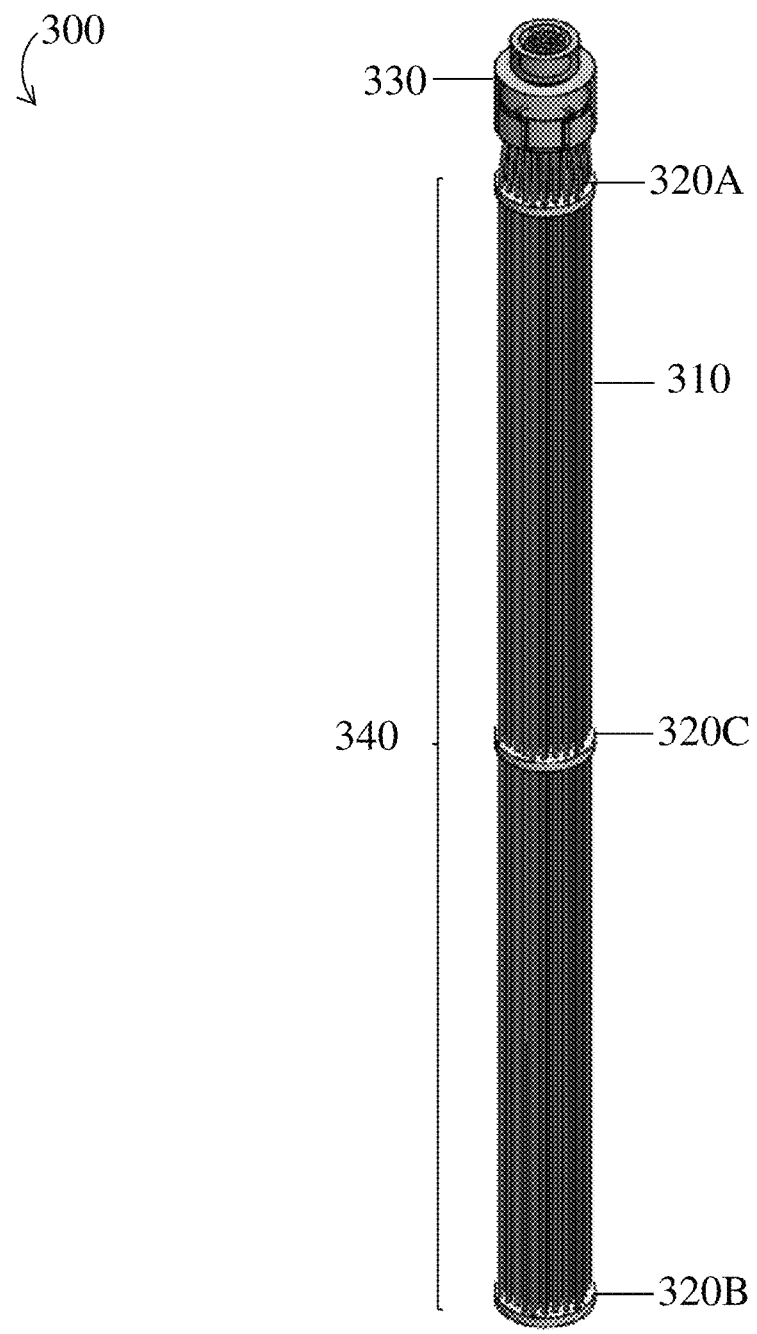
FIG. 3A is a schematic illustration of an active filtering area of a filter probe, according to some embodiments.
Figure 3B:
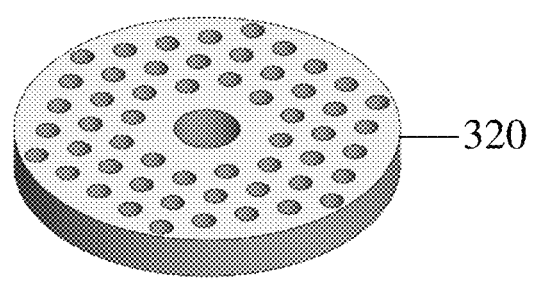
FIG. 3B is a schematic illustration of an exemplary spacing element, according to some embodiments.
Figure 3C:
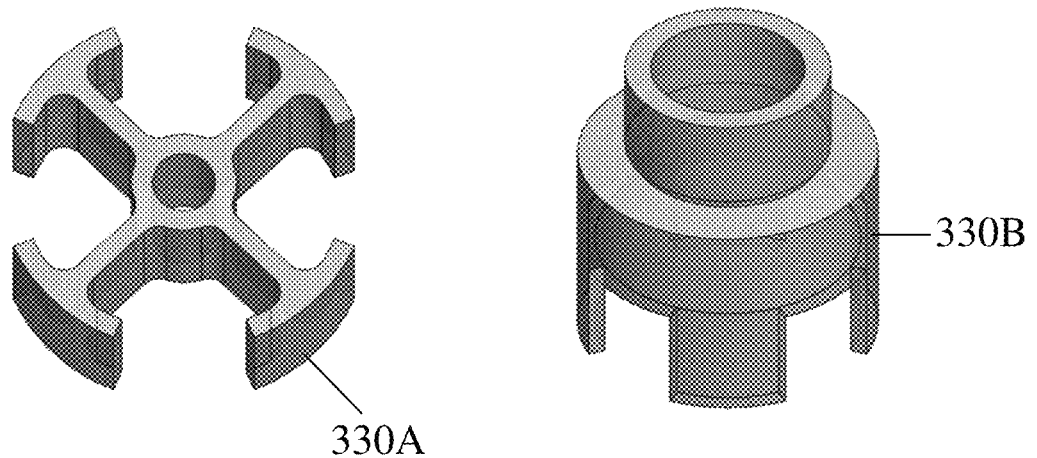
FIG. 3C is a schematic illustration of the components of an exemplary end piece, according to some embodiments.
Figure 3D:
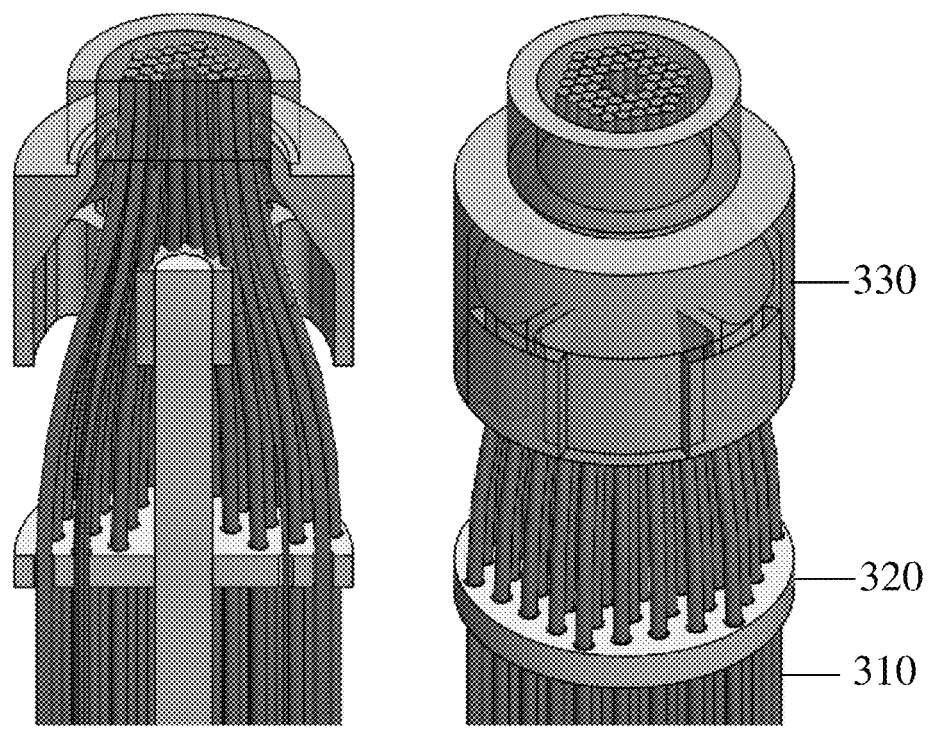
FIG. 3D is a schematic illustration of a portion of an exemplary filter probe, according to some embodiments.

To further illustrate various filter probe components, FIGS. 3A-D provide detailed views of an exemplary embodiment of a filter probe. In particular, FIG. 3A illustrates the active filtering area of exemplary filter probe 300. As shown in FIG. 3A, filter probe 300 comprises a plurality of longitudinally aligned hollow fibers 310. In addition, filter probe 300 further comprises first spacing element 320A, second spacing element 320B, third spacing element 320C, and end piece 330. In FIG. 3A, structured segment 340 extends from first spacing element 320A to second spacing element 320B. In some embodiments, any portions of hollow fibers 310 extending beyond second spacing element 320B may be sealed (e.g., through potting) to prevent fluids from entering the central cavities (i.e., lumens) of hollow fibers 310 through the ends of the hollow fibers. FIG. 3B is a schematic illustration of exemplary spacing element 320. FIG. 3C is a schematic illustration of exemplary hub 330A and exemplary mounting collar 330B, which collectively form end piece 330. FIG. 3D provides additional views of a top portion of the active filtering area of filter probe 300.

In some embodiments, the filter probe comprises a fiber bundle comprising a plurality of hollow fibers. Hollow fiber membranes are generally known and commercially available, and a person of ordinary skill in the art would understand a "hollow fiber" to refer to a membrane (e.g., a porous or semi-porous membrane) surrounding a central cavity (also referred to as a "lumen"). A hollow fiber generally has an outer surface (e.g., an outer surface of the membrane) having an outer diameter (i.e., the largest cross-sectional dimension of the outer surface). In addition, a hollow fiber generally has an inner surface (e.g., an inner surface of the membrane defining the lumen) having an inner diameter (i.e., the largest cross-sectional dimension of the inner surface). The inner and outer surfaces of a hollow fiber may define any suitable shape. In some instances, the inner surface and/or outer surface of a hollow fiber may have a cross section that is substantially circular, substantially hexagonal, substantially elliptical, substantially square, substantially rectangular, or substantially triangular. A hollow fiber generally also has a longitudinal axis. A hollow fiber of the fiber bundle may be characterized by a particular perimetric shape of the outer perimeter and the inner perimeter (delimiting the lumen), as measured for a cross section of the fiber taken perpendicular to its longitudinal axis. Typically, the outer perimetric shape and the inner perimetric shape are substantially the same so that the cross-sectional wall thickness of the membrane will be substantially uniform about the fiber circumference. The particular perimetric shape is typically substantially circular, but may in some embodiments be, for example, substantially hexagonal, substantially elliptical, substantially square, substantially rectangular, or substantially triangular. In certain cases, each hollow fiber of the fiber bundle has substantially the same perimetric shape.

In some embodiments, the fiber bundle comprises a plurality of longitudinally aligned hollow fibers. A person of ordinary skill in the art, in view of the teaching of the present specification, would understand longitudinally aligned hollow fibers to be aligned to be substantially parallel to each other within the constraints of ordinary manufacturing processes. In some embodiments, a plurality of longitudinally aligned hollow fibers are arranged such that at least about 50%, at least about 60%, at least about 70%, at least about 80%, at least about 90%, at least about 95%, at least about 99%, or substantially all of the hollow fibers are substantially parallel to each other (e.g., deviating from absolute parallelism by about 10° or less, about 5° or less, about 2° or less, or about 1° or less) along at least a portion of their lengths (e.g., within a structured segment of a filter probe). In certain cases, the plurality of longitudinally aligned hollow fibers are arranged such that at least about 50%, at least about 60%, at least about 70%, at least about 80%, at least about 90%, at least about 95%, at least about 99%, or substantially all of the hollow fibers do not intersect any adjacent fibers along at least a portion of their lengths (e.g., within a structured segment of a filter probe). In some instances, the plurality of longitudinally aligned hollow fibers are arranged such that at least about 50%, at least about 60%, at least about 70%, at least about 80%, at least about 90%, at least about 95%, at least about 99%, or substantially all of the hollow fibers do not intersect any adjacent fibers along any portion of their lengths.

In some embodiments, the fiber bundle comprises a plurality of hollow fibers having variable alignment along at least a portion of their lengths (e.g., within a structured segment of the filter probe). In certain instances, a structured segment of a filter probe comprises one or more regions delimited by one or more spacing elements (e.g., a first region between a first and second spacing element, a second region between a second and third spacing element, a third region between a third and fourth spacing element, etc.). In some embodiments, alignment of the plurality of hollow fibers in two or more regions of the structured segment may be the same or different. In certain cases, for example, the plurality of hollow fibers in one or more regions of the structured segment may be longitudinally aligned. In some cases, the plurality of hollow fibers in one or more regions of the structured segment may be angled relative to each other and/or to one or more adjacent spacing elements. In certain embodiments, the minimum center-to-center distance between any two hollow fibers in a first region of a structured segment may be the same or different from the minimum center-to-center distance between any two hollow fibers in a second region of the structured segment. In some instances, the average center-to-center distance between hollow fibers in a first region of a structured segment may be the same or different from the average center-to-center distance between hollow fibers in a second region of the structured segment. The average center-to-center distance between hollow fibers in a region generally refers to a number average of the center-to-center distance between each hollow fiber and its nearest neighbor.

Figure 4:
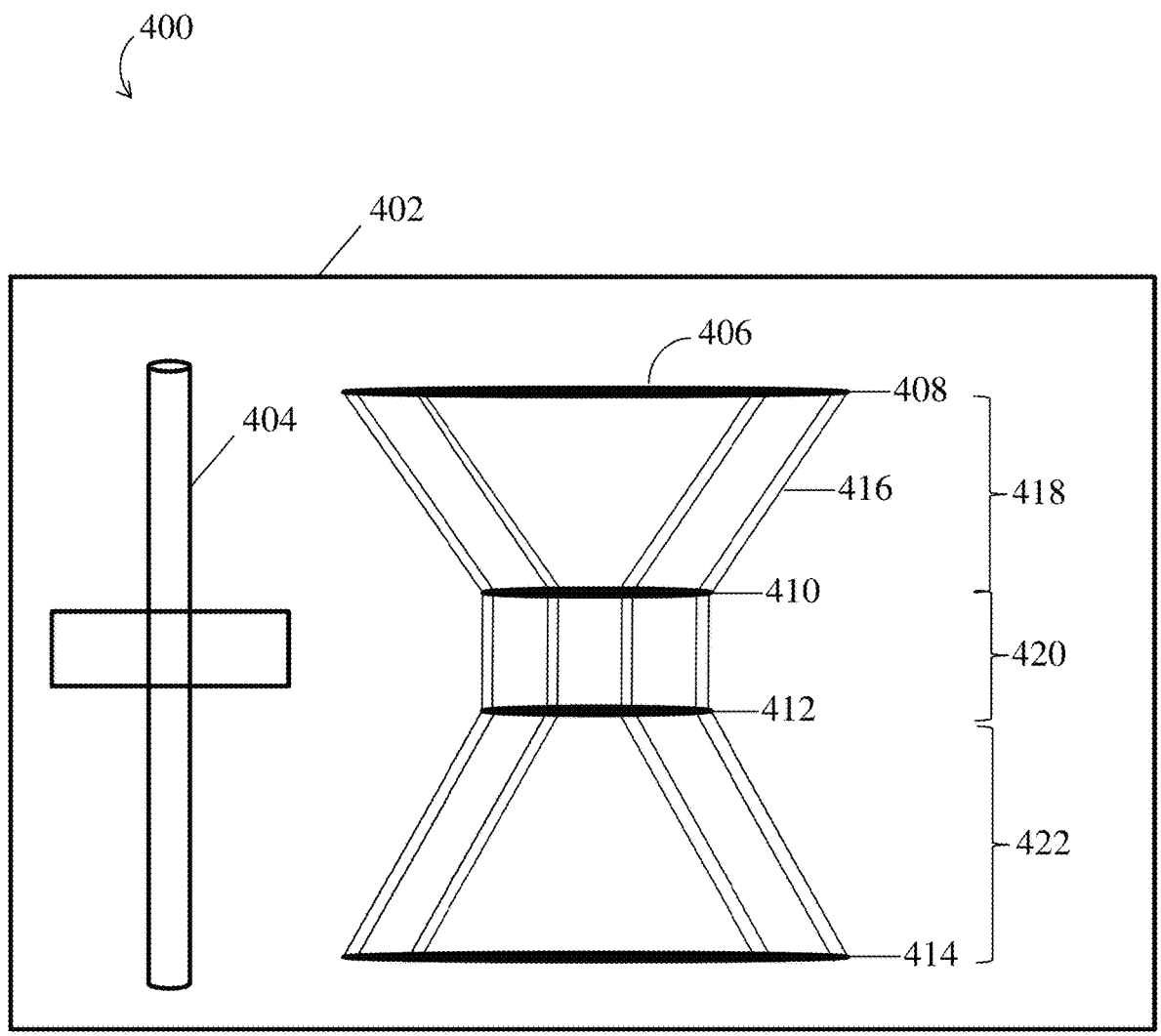
FIG. 4 is, according to some embodiments, a schematic illustration of an exemplary system comprising a bioreactor, an agitator, and a filter probe comprising a plurality of hollow fibers having variable alignment along a structured segment of the filter probe.

A schematic illustration of an exemplary filter probe comprising a fiber bundle comprising a plurality of hollow fibers having variable alignment along at least a portion of their lengths (e.g., within a structured segment of the filter probe) is shown in FIG. 4. In FIG. 4, system 400 comprises bioreactor 402, which contains impeller 404 and filter probe 406. Filter probe 406 comprises a structured segment comprising four spacing elements (first spacing element 408, second spacing element 410, third spacing element 412, fourth spacing element 414) delimiting three regions (first region 418, second region 420, third region 422) of hollow fibers 416. As shown in FIG. 4, second spacing element 410 and third spacing element 412 have smaller diameters than first spacing element 408 and fourth spacing element 414. As a result, hollow fibers 416 in first region 418 and third region 422 are angled with respect to at least a portion of the other fibers in the same region and with respect to the adjacent spacing elements. In second region 420, hollow fibers 416 are longitudinally aligned. Such embodiments may, in some instances, make it possible to accommodate other components inside a bioreactor, such as an impeller, pH probe, one or more baffles, and/or a sparger. For example, the variable alignment of hollow fibers 416 may advantageously prevent filter probe 406 from coming into contact with impeller 404.

Figure 5:
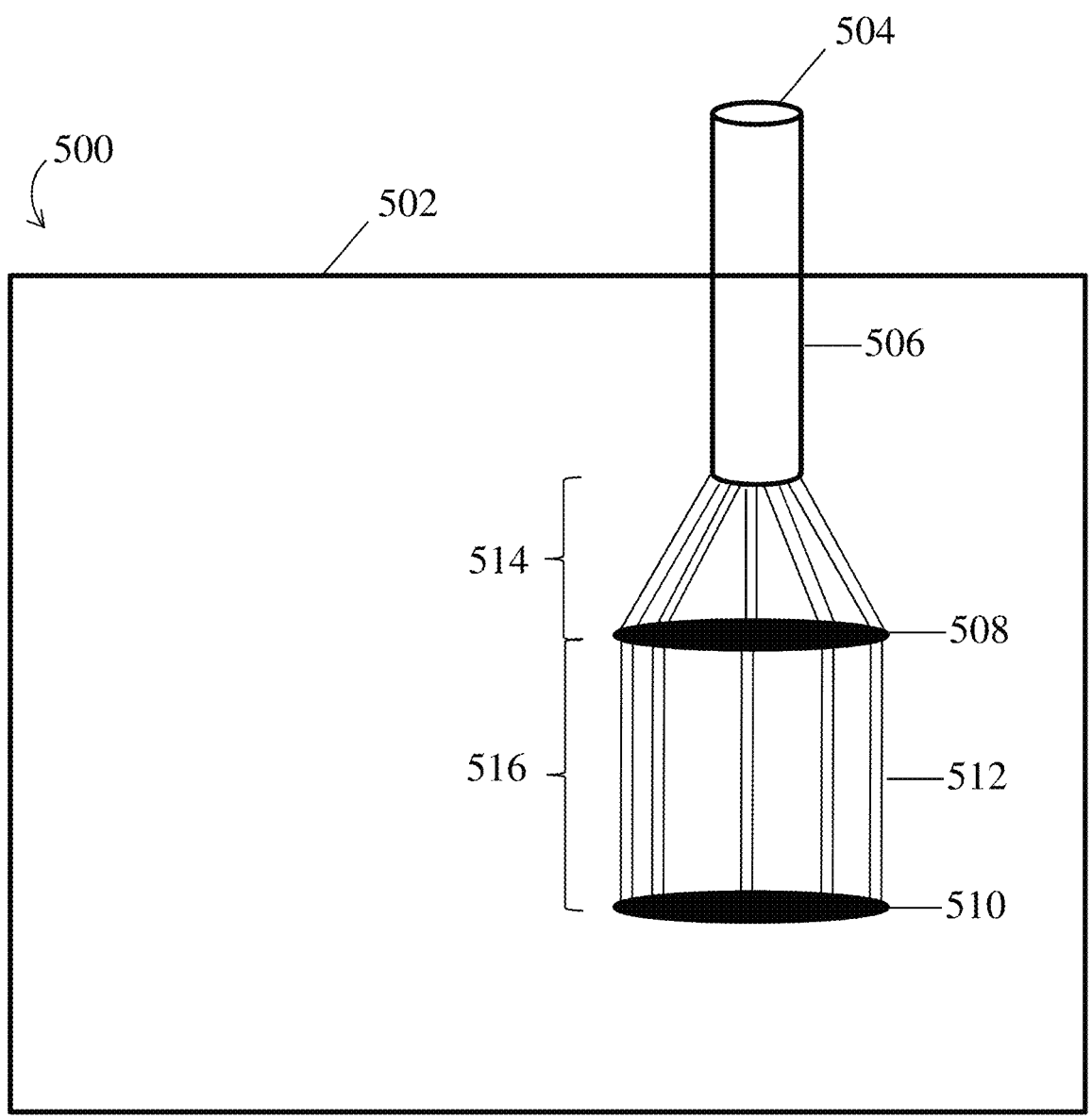
FIG. 5 is a schematic illustration of an exemplary system comprising a bioreactor and a filter probe comprising a plurality of hollow fibers having variable alignment along a structured segment of the filter probe, according to some embodiments.

A schematic illustration of another exemplary filter probe comprising a fiber bundle comprising a plurality of hollow fibers having variable alignment along at least a portion of their lengths (e.g., within a structured segment of the filter probe) is shown in FIG. 5. In FIG. 5, system 500 comprises bioreactor 502, which contains filter probe 504. Filter probe 504 comprises first portion 506, which is configured to be at least partially inserted into bioreactor 502 through a port. Filter probe 504 further comprises a structured segment comprising first region 514, which is delimited by first portion 506 and first spacing element 508, and second region 516, which is delimited by first spacing element 508 and second spacing element 510. As shown in FIG. 5, first spacing element 508 and second spacing element 510 both have larger diameters than first portion 506. In first region 514, hollow fibers 512 are angled with respect to at least a portion of other fibers in this region and with respect to first portion 506 and first spacing element 508. In second region 516, hollow fibers 512 are longitudinally aligned. In some cases, this configuration of hollow fibers may advantageously allow hollow fiber spacing in at least a portion of the structured segment to be unconstrained by bioreactor port size.

In some embodiments, one or more spacing elements of a filter probe may maintain a desired center-to-center spacing between hollow fibers of the filter probe. For example, a spacing element may comprise a plurality of clearance holes (e.g., holes through which a hollow fiber can pass) having an average center-to-center distance (e.g., a number average of the center-to-center distance between each hole and its nearest neighbor).

In certain embodiments, the average center-to-center distance of a plurality of holes of a spacing element of a filter probe is greater than or equal to the minimum hole diameter of the plurality of holes, greater than or equal to 1.1 times the minimum hole diameter of the plurality of holes, greater than or equal to 1.2 times the minimum hole diameter of the plurality of holes, greater than or equal to 1.3 times the minimum hole diameter of the plurality of holes, greater than or equal to 1.4 times the minimum hole diameter of the plurality of holes, greater than or equal to 1.5 times the minimum hole diameter of the plurality of holes, greater than or equal to 2 times the minimum hole diameter of the plurality of holes, greater than or equal to 2.5 times the minimum hole diameter of the plurality of holes, greater than or equal to 3 times the minimum hole diameter of the plurality of holes, greater than or equal to 3.5 times the minimum hole diameter of the plurality of holes, greater than or equal to 4 times the minimum hole diameter of the plurality of holes, greater than or equal to 4.5 times the minimum hole diameter of the plurality of holes, or greater than or equal to 5 times the minimum hole diameter of the plurality of holes. In some embodiments, the average center-to-center distance of a plurality of holes of a spacing element of a filter probe is between 1 and 1.5 times the minimum hole diameter of the plurality of holes, between 1 and 2 times the minimum hole diameter of the plurality of holes, between 1 and 2.5 times the minimum hole diameter of the plurality of holes, between 1 and 3 times the minimum hole diameter of the plurality of holes, between 1 and 3.5 times the minimum hole diameter of the plurality of holes, between 1 and 4 times the minimum hole diameter of the plurality of holes, between 1 and 4.5 times the minimum hole diameter of the plurality of holes, between 1 and 5 times the minimum hole diameter of the plurality of holes, between 1.1 and 1.5 times the minimum hole diameter of the plurality of holes, between 1.1 and 2 times the minimum hole diameter of the plurality of holes, between 1.1 and 2.5 times the minimum hole diameter of the plurality of holes, between 1.1 and 3 times the minimum hole diameter of the plurality of holes, between 1.1 and 3.5 times the minimum hole diameter of the plurality of holes, between 1.1 and 4 times the minimum hole diameter of the plurality of holes, between 1.1 and 4.5 times the minimum hole diameter of the plurality of holes, between 1.1 and 5 times the minimum hole diameter of the plurality of holes, between 2 and 2.5 times the minimum hole diameter of the plurality of holes, between 2 and 3 times the minimum hole diameter of the plurality of holes, between 2 and 3.5 times the minimum hole diameter of the plurality of holes, between 2 and 4 times the minimum hole diameter of the plurality of holes, between 2 and 4.5 times the minimum hole diameter of the plurality of holes, between 2 and 5 times the minimum hole diameter of the plurality of holes, between 2.5 and 3 times the minimum hole diameter of the plurality of holes, between 2.5 and 3.5 times the minimum hole diameter of the plurality of holes, between 2.5 and 4 times the minimum hole diameter of the plurality of holes, between 2.5 and 4.5 times the minimum hole diameter of the plurality of holes, between 2.5 and 5 times the minimum hole diameter of the plurality of holes, between 3 and 3.5 times the minimum hole diameter of the plurality of holes, between 3 and 4 times the minimum hole diameter of the plurality of holes, between 3 and 4.5 times the minimum hole diameter of the plurality of holes, between 3 and 5 times the minimum hole diameter of the plurality of holes, between 3.5 and 4 times the minimum hole diameter of the plurality of holes, between 3.5 and 4.5 times the minimum hole diameter of the plurality of holes, between 3.5 and 5 times the minimum hole diameter of the plurality of holes, between 4 and 4.5 times the minimum hole diameter of the plurality of holes, between 4 and 5 times the minimum hole diameter of the plurality of holes, or between 4.5 and 5 times the minimum hole diameter of the plurality of holes. The minimum hole diameter of the plurality of holes refers to a smallest cross-sectional dimension of the plurality of holes.

In certain embodiments, the average center-to-center distance of a plurality of holes of a spacing element of a filter probe is greater than or equal to the average hole diameter of the plurality of holes, greater than or equal to 1.1 times the average hole diameter of the plurality of holes, greater than or equal to 1.2 times the average hole diameter of the plurality of holes, greater than or equal to 1.3 times the average hole diameter of the plurality of holes, greater than or equal to 1.4 times the average hole diameter of the plurality of holes, greater than or equal to 1.5 times the average hole diameter of the plurality of holes, greater than or equal to 2 times the average hole diameter of the plurality of holes, greater than or equal to 2.5 times the average hole diameter of the plurality of holes, greater than or equal to 3 times the average hole diameter of the plurality of holes, greater than or equal to 3.5 times the average hole diameter of the plurality of holes, greater than or equal to 4 times the average hole diameter of the plurality of holes, greater than or equal to 4.5 times the average hole diameter of the plurality of holes, or greater than or equal to 5 times the average hole diameter of the plurality of holes. In some embodiments, the average center-to-center distance of a plurality of holes of a spacing element of a filter probe is between 1 and 1.5 times the average hole diameter of the plurality of holes, between 1 and 2 times the average hole diameter of the plurality of holes, between 1 and 2.5 times the average hole diameter of the plurality of holes, between 1 and 3 times the average hole diameter of the plurality of holes, between 1 and 3.5 times the average hole diameter of the plurality of holes, between 1 and 4 times the average hole diameter of the plurality of holes, between 1 and 4.5 times the average hole diameter of the plurality of holes, between 1 and 5 times the average hole diameter of the plurality of holes, between 1.1 and 1.5 times the average hole diameter of the plurality of holes, between 1.1 and 2 times the average hole diameter of the plurality of holes, between 1.1 and 2.5 times the average hole diameter of the plurality of holes, between 1.1 and 3 times the average hole diameter of the plurality of holes, between 1.1 and 3.5 times the average hole diameter of the plurality of holes, between 1.1 and 4 times the average hole diameter of the plurality of holes, between 1.1 and 4.5 times the average hole diameter of the plurality of holes, between 1.1 and 5 times the average hole diameter of the plurality of holes, between 2 and 2.5 times the average hole diameter of the plurality of holes, between 2 and 3 times the average hole diameter of the plurality of holes, between 2 and 3.5 times the average hole diameter of the plurality of holes, between 2 and 4 times the average hole diameter of the plurality of holes, between 2 and 4.5 times the average hole diameter of the plurality of holes, between 2 and 5 times the average hole diameter of the plurality of holes, between 2.5 and 3 times the average hole diameter of the plurality of holes, between 2.5 and 3.5 times the average hole diameter of the plurality of holes, between 2.5 and 4 times the average hole diameter of the plurality of holes, between 2.5 and 4.5 times the average hole diameter of the plurality of holes, between 2.5 and 5 times the average hole diameter of the plurality of holes, between 3 and 3.5 times the average hole diameter of the plurality of holes, between 3 and 4 times the average hole diameter of the plurality of holes, between 3 and 4.5 times the average hole diameter of the plurality of holes, between 3 and 5 times the average hole diameter of the plurality of holes, between 3.5 and 4 times the average hole diameter of the plurality of holes, between 3.5 and 4.5 times the average hole diameter of the plurality of holes, between 3.5 and 5 times the average hole diameter of the plurality of holes, between 4 and 4.5 times the average hole diameter of the plurality of holes, between 4 and 5 times the average hole diameter of the plurality of holes, or between 4.5 and 5 times the average hole diameter of the plurality of holes. The average hole diameter of the plurality of holes refers to a number average of the diameters of the plurality of holes.

In some embodiments, the average center-to-center distance of a plurality of holes of a spacing element of a filter probe is at least about 0.5 mm, at least about 1 mm, at least about 1.5 mm, at least about 2 mm, at least about 2.5 mm, at least about 3 mm, at least about 3.5 mm, at least about 4 mm, at least about 4.5 mm, or at least about 5 mm. In some embodiments, the average center-to-center distance of a plurality of holes of a spacing element of a filter probe is between about 0.5 mm and about 1 mm, between about 0.5 mm and about 1.5 mm, between about 0.5 mm and about 2 mm, between about 0.5 mm and about 2.5 mm, between about 0.5 mm and about 3 mm, between about 0.5 mm and about 3.5 mm, between about 0.5 mm and about 4 mm, between about 0.5 mm and about 4.5 mm, between about 0.5 mm and about 5 mm, between about 1 mm and about 2 mm, between about 1 mm and about 2.5 mm, between about 1 mm and about 3 mm, between about 1 mm and about 3.5 mm, between about 1 mm and about 4 mm, between about 1 mm and about 4.5 mm, between about 1 mm and about 5 mm, between about 2 mm and about 3 mm, between about 2 mm and about 3.5 mm, between about 2 mm and about 4 mm, between about 2 mm and about 4.5 mm, between about 2 mm and about 5 mm, between about 3 mm and about 5 mm, or between about 4 mm and about 5 mm.

The fiber bundle may comprise any number of hollow fibers. In some embodiments, the fiber bundle comprises at least about 2 hollow fibers, at least about 5 hollow fibers, at least about 10 hollow fibers, at least about 15 hollow fibers, at least about 20 hollow fibers, at least about 50 hollow fibers, at least about 100 hollow fibers, at least about 200 hollow fibers, at least about 500 hollow fibers, at least about 1000 hollow fibers, at least about 1500 hollow fibers, at least about 2000 hollow fibers, at least about 2200 hollow fibers, or at least about 2500 hollow fibers. In some embodiments, the fiber bundle comprises about 2500 hollow fibers or less, about 2200 hollow fibers or less, about 2000 hollow fibers or less, about 1500 hollow fibers or less, about 1000 hollow fibers or less, about 500 hollow fibers or less, about 200 hollow fibers or less, about 100 hollow fibers or less, about 50 hollow fibers or less, about 20 hollow fibers or less, about 15 hollow fibers or less, about 10 hollow fibers or less, about 5 hollow fibers or less, or about 2 hollow fibers. In some embodiments, the fiber bundle comprises between 2 and 10 hollow fibers, between 2 and 20 hollow fibers, between 2 and 50 hollow fibers, between 2 and 100 hollow fibers, between 2 and 500 hollow fibers, between 2 and 1000 hollow fibers, between 2 and 1500 hollow fibers, between 2 and 2000 hollow fibers, between 2 and 2200 hollow fibers, between 2 and 2500 hollow fibers, between 10 and 20 hollow fibers, between 10 and 50 hollow fibers, between 10 and 100 hollow fibers, between 10 and 500 hollow fibers, between 10 and 1000 hollow fibers, between 10 and 1500 hollow fibers, between 10 and 2000 hollow fibers, between 10 and 2200 hollow fibers, between 10 and 2500 hollow fibers, between 50 and 100 hollow fibers, between 50 and 500 hollow fibers, between 50 and 1000 hollow fibers, between 50 and 1500 hollow fibers, between 50 and 2000 hollow fibers, between 50 and 2200 hollow fibers, between 50 and 2500 hollow fibers, between 100 and 500 hollow fibers, between 100 and 1000 hollow fibers, between 100 and 1500 hollow fibers, between 100 and 2000 hollow fibers, between 100 and 2200 hollow fibers, between 100 and 2500 hollow fibers, between 500 and 1000 hollow fibers, between 500 and 1500 hollow fibers, between 500 and 2000 hollow fibers, between 500 and 2200 hollow fibers, between 500 and 2500 hollow fibers, between 1000 and 1500 hollow fibers, between 1000 and 2000 hollow fibers, between 1000 and 2200 hollow fibers, between 1000 and 2500 hollow fibers, between 1500 and 2000 hollow fibers, between 1500 and 2200 hollow fibers, between 1500 and 2500 hollow fibers, or between 2000 and 2500 hollow fibers.

Each hollow fiber of the fiber bundle may have an outer diameter. The diameter (e.g., outer diameter) of a hollow fiber may be measured according to any method known in the art. For example, the diameter (e.g., outer diameter) may be measured using calipers. The average outer diameter of the hollow fibers of the fiber bundle may be obtained by calculating the number average of the outer diameters of the hollow fibers in the fiber bundle. In some embodiments, the average outer diameter of the hollow fibers of the fiber bundle is at least about 0.5 mm, at least about 0.6 mm, at least about 0.7 mm, at least about 0.8 mm, at least about 0.9 mm, at least about 1 mm, at least about 1.1 mm, at least about 1.2 mm, at least about 1.3 mm, at least about 1.4 mm, at least about 1.5 mm, at least about 2.0 mm, at least about 3.0 mm, at least about 4.0 mm, or at least about 5.0 mm. In some embodiments, the average outer diameter of the hollow fibers of the fiber bundle is about 5.0 mm or less, about 4.0 mm or less, about 3.0 mm or less, about 2.0 mm or less, about 1.5 mm or less, about 1.4 mm or less, about 1.3 mm or less, about 1.2 mm or less, about 1.1 mm or less, about 1 mm or less, about 0.9 mm or less, about 0.8 mm or less, about 0.7 mm or less, about 0.6 mm or less, or about 0.5 mm or less. In some embodiments, the average outer diameter of the hollow fibers of the fiber bundle is in a range between about 0.5 mm and about 0.6 mm, between about 0.5 mm and about 0.7 mm, between about 0.5 mm and about 0.8 mm, between about 0.5 mm and about 0.9 mm, between about 0.5 mm and about 1 mm, between about 0.5 mm and about 1.1 mm, between about 0.5 mm and about 1.2 mm, between about 0.5 mm and about 1.3 mm, between about 0.5 mm and about 1.4 mm, between about 0.5 mm and about 1.5 mm, between about 0.5 mm and about 2.0 mm, between about 0.5 mm and about 3.0 mm, between about 0.5 mm and about 4.0 mm, between about 0.5 mm and about 5.0 mm, between about 0.8 mm and about 0.9 mm, between about 0.8 mm and about 1 mm, between about 0.8 mm and about 1.1 mm, between about 0.8 mm and about 1.2 mm, between about 0.8 mm and about 0.8 mm and about 1.3 mm, between about 0.8 mm and about 1.4 mm, between about 0.8 mm and about 1.5 mm, between about 1.0 mm and about 1.1 mm, between about 1.0 mm and about 1.2 mm, between about 1.0 mm and about 1.3 mm, between about 1.0 mm and about 1.4 mm, between about 1.0 mm and about 1.5 mm, between about 1.0 mm and about 2.0 mm, between about 1.0 mm and about 3.0 mm, between about 1.0 mm and about 4.0 mm, between about 1.0 mm and about 5.0 mm, between about 2.0 mm and about 5.0 mm, between about 3.0 mm and about 5.0 mm, or between about 4.0 mm and about 5.0 mm.

Each hollow fiber of the fiber bundle may also have an inner diameter. The average inner diameter of the hollow fibers of the fiber bundle may be obtained by calculating the number average of the inner diameters of the hollow fibers in the fiber bundle. In some embodiments, the average inner diameter of the hollow fibers of the fiber bundle is at least about 0.5 mm, at least about 0.6 mm, at least about 0.7 mm, at least about 0.8 mm, at least about 0.9 mm, at least about 1 mm, at least about 1.1 mm, at least about 1.2 mm, at least about 1.3 mm, at least about 1.4 mm, at least about 1.5 mm, at least about 2.0 mm, at least about 3.0 mm, at least about 4.0 mm, or at least about 5.0 mm. In some embodiments, the average inner diameter of the hollow fibers of the fiber bundle is about 5.0 mm or less, about 4.0 mm or less, about 3.0 mm or less, about 2.0 mm or less, about 1.5 mm or less, about 1.4 mm or less, about 1.3 mm or less, about 1.2 mm or less, about 1.1 mm or less, about 1 mm or less, about 0.9 mm or less, about 0.8 mm or less, about 0.7 mm or less, about 0.6 mm or less, or about 0.5 mm or less. In some embodiments, the average inner diameter of the hollow fibers of the fiber bundle is in a range between about 0.5 mm and about 0.6 mm, between about 0.5 mm and about 0.7 mm, between about 0.5 mm and about 0.8 mm, between about 0.5 mm and about 0.9 mm, between about 0.5 mm and about 1 mm, between about 0.5 mm and about 1.1 mm, between about 0.5 mm and about 1.2 mm, between about 0.5 mm and about 1.3 mm, between about 0.5 mm and about 1.4 mm, between about 0.5 mm and about 1.5 mm, between about 0.5 mm and about 2.0 mm, between about 0.5 mm and about 3.0 mm, between about 0.5 mm and about 4.0 mm, between about 0.5 mm and about 5.0 mm, between about 0.8 mm and about 0.9 mm, between about 0.8 mm and about 1 mm, between about 0.8 mm and about 1.1 mm, between about 0.8 mm and about 1.2 mm, between about 0.8 mm and about 1.3 mm, between about 0.8 mm and about 1.4 mm, between about 0.8 mm and about 1.5 mm, between about 1.0 mm and about 1.1 mm, between about 1.0 mm and about 1.2 mm, between about 1.0 mm and about 1.3 mm, between about 1.0 mm and about 1.4 mm, between about 1.0 mm and about 1.5 mm, between about 1.0 mm and about 2.0 mm, between about 1.0 mm and about 3.0 mm, between about 1.0 mm and about 4.0 mm, between about 1.0 mm and about 5.0 mm, between about 2.0 mm and about 5.0 mm, between about 3.0 mm and about 5.0 mm, or between about 4.0 mm and about 5.0 mm.

In some embodiments, the hollow fibers of the fiber bundle may comprise a plurality of pores. According to certain embodiments, at least one hollow fiber within the fiber bundle comprises a plurality of pores having an average pore size of at least about 0.025 microns (μm), at least about 0.05 μm, at least about 0.08 μm, at least about 0.1 μm, at least about 0.2 μm, at least about 0.3 μm, at least about 0.4

μm, at least about 0.5 μm, at least about 0.8 μm, at least about 1 μm, at least about 1.5 μm, or at least about 2.0 μm. In certain instances, at least one hollow fiber within the fiber bundle comprises a plurality of pores having an average pore size of about 2.0 μm or less, about 1.5 μm or less, about 1 μm or less, about 0.8 μm or less, about 0.5 μm or less, about 0.4 μm or less, about 0.3 μm or less, about 0.2 μm or less, about 0.1 μm or less, about 0.08 μm or less, about 0.05 μm or less, or about 0.025 μm or less. In some embodiments, at least one hollow fiber within the fiber bundle comprises a plurality of pores having an average pore size in a range from about 0.025 μm to about 0.05 μm, about 0.025 μm to about 0.1 μm, about 0.025 μm to about 0.5 μm, about 0.025 μm to about 1 μm, about 0.025 μm to about 1.5 μm, about 0.025 μm to about 2.0 μm, about 0.05 μm to about 0.1 μm, about 0.05 μm to about 0.5 μm, about 0.05 μm to about 1 μm, about 0.05 μm to about 1.5 μm, about 0.05 μm to about 2.0 μm, about 0.1 μm to about 0.5 μm, about 0.1 μm to about 1 μm, about 0.1 μm to about 1.5 μm, about 0.1 μm to about 2.0 μm, about 0.2 μm to about 0.5 μm, about 0.2 μm to about 1 μm, about 0.2 μm to about 1.5 μm, about 0.2 μm to about 2.0 μm, about 0.5 μm to about 1 μm, about 0.5 μm to about 1.5 μm, about 0.5 μm to about 2.0 μm, or about 1.0 μm to about 2.0 μm. The average pore size of a hollow fiber may be measured according to any method known in the art. For example, the average pore size may be obtained by porometry (e.g., capillary flow porometry).

In some embodiments, each hollow fiber within the fiber bundle has an average pore size of at least about 0.025 μm, at least about 0.05 μm, at least about 0.08 μm, at least about 0.1 μm, at least about 0.2 μm, at least about 0.3 μm, at least about 0.4 μm, at least about 0.5 μm, at least about 0.8 μm, at least about 1 μm, at least about 1.5 μm, or at least about 2.0 μm. In some embodiments, each hollow fiber within the fiber bundle has an average pore size of about 2.0 μm or less, about 1.5 μm or less, about 1 μm or less, about 0.8 μm or less, about 0.5 μm or less, about 0.4 μm or less, about 0.3 μm or less, about 0.2 μm or less, about 0.1 μm or less, about 0.08 μm or less, about 0.05 μm or less, or about 0.025 μm or less. In some embodiments, each hollow fiber within the fiber bundle has an average pore size in a range from about 0.025 μm to about 0.05 μm, about 0.025 μm to about 0.1 μm, about 0.025 μm to about 0.5 μm, about 0.025 μm to about 1 μm, about 0.025 μm to about 1.5 μm, about 0.025 μm to about 2.0 μm, about 0.05 μm to about 0.1 μm, about 0.05 μm to about 0.5 μm, about 0.05 μm to about 1 μm, about 0.05 μm to about 1.5 μm, about 0.05 μm to about 2.0 μm, about 0.1 μm to about 0.5 μm, about 0.1 μm to about 1 μm, about 0.1 μm to about 1.5 μm, about 0.1 μm to about 2.0 μm, about 0.2 μm to about 0.5 μm, about 0.2 μm to about 1 μm, about 0.2 μm to about 1.5 μm, about 0.2 μm to about 2.0 μm, about 0.5 μm to about 1 μm, about 0.5 μm to about 1.5 μm, about 0.5 μm to about 2.0 μm, or about 1.0 μm to about 2.0 μm.

In some instances, the plurality of pores of a hollow fiber may be characterized by a molecular weight cut-off pore size. The molecular weight cut-off pore size of a hollow fiber generally refers to the lowest molecular weight solute for which 90% of the solute is rejected by the hollow fiber. The molecular weight cut-off pore size of a hollow fiber may be determined by standard methods that are well known in the art. For example, the molecular weight cut-off pore size may be obtained by conducting permeation tests with solutes of different molecular weights. In some embodiments, at least one hollow fiber within the fiber bundle has a molecular weight cut-off pore size of at least about 1 kDa, at least about 5 kDa, at least about 10 kDa, at least about 20 kDa, at least about 50 kDa, at least about 100 kDa, at least about 150 kDa, at least about 200 kDa, at least about 250 kDa, at least about 300 kDa, at least about 350 kDa, at least about 400 kDa, at least about 450 kDa, at least about 500 kDa, at least about 1,000 kDa, at least about 5,000 kDa, at least about 10,000 kDa, at least about 20,000 kDa, at least about 50,000 kDa, or at least about 100,000 kDa. In some embodiments, at least one hollow fiber within the fiber bundle has a molecular weight cut-off pore size of about 100,000 kDa or less, about 50,000 kDa or less, about 20,000 kDa or less, about 10,000 kDa or less, about 5,000 kDa or less, about 1,000 kDa or less, about 500 kDa or less, about 450 kDa or less, about 400 kDa or less, about 350 kDa or less, about 300 kDa or less, about 250 kDa or less, about 200 kDa or less, about 150 kDa or less, about 100 kDa or less, about 50 kDa or less, about 20 kDa or less, about 10 kDa or less, about 5 kDa or less, or about 1 kDa or less. In some embodiments, at least one hollow fiber within the fiber bundle has a molecular weight cut-off pore size between about 1 kDa and about 5 kDa, between about 1 kDa and about 10 kDa, between about 1 kDa and about 20 kDa, between about 1 kDa and about 50 kDa, between about 1 kDa and about 100 kDa, between about 1 kDa and about 200 kDa, between about 1 kDa and about 300 kDa, between about 1 kDa and about 400 kDa, between about 1 kDa and about 500 kDa, between about 1 kDa and about 1,000 kDa, between about 1 kDa and about 5,000 kDa, between about 1 kDa and about 10,000 kDa, between about 1 kDa and about 20,000 kDa, between about 1 kDa and about 50,000 kDa, between about 1 kDa and about 100,000 kDa, between about 10 kDa and about 50 kDa, between about 10 kDa and about 100 kDa, between about 10 kDa and about 200 kDa, between about 10 kDa and about 300 kDa, between about 10 kDa and about 400 kDa, between about 10 kDa and about 500 kDa, between about 10 kDa and about 1,000 kDa, between about 10 kDa and about 5,000 kDa, between about 10 kDa and about 10,000 kDa, between about 10 kDa and about 20,000 kDa, between about 10 kDa and about 50,000 kDa, between about 10 kDa and about 100,000 kDa, between about 100 kDa and about 200 kDa, between about 100 kDa and about 300 kDa, between about 100 kDa and about 400 kDa, between about 100 kDa and about 500 kDa, between about 100 kDa and about 1,000 kDa, between about 100 kDa and about 5,000 kDa, between about 100 kDa and about 10,000 kDa, between about 100 kDa and about 20,000 kDa, between about 100 kDa and about 50,000 kDa, between about 100 kDa and about 100,000 kDa, between about 500 kDa and about 1,000 kDa, between about 500 kDa and about 5,000 kDa, between about 500 kDa and about 10,000 kDa, between about 500 kDa and about 20,000 kDa, between about 500 kDa and about 50,000 kDa, between about 500 kDa and about 100,000 kDa, between about 1,000 kDa and about 5,000 kDa, between about 1,000 kDa and about 10,000 kDa, between about 1,000 kDa and about 20,000 kDa, between about 1,000 kDa and about 50,000 kDa, between about 1,000 kDa and about 100,000 kDa, between about 5,000 kDa and about 10,000 kDa, between about 5,000 kDa and about 20,000 kDa, between about 5,000 kDa and about 50,000 kDa, between about 5,000 kDa and about 100,000 kDa, between about 10,000 kDa and about 20,000 kDa, between about 10,000 kDa and about 50,000 kDa, between about 10,000 kDa and about 100,000 kDa, or between about 50,000 kDa and about 100,000 kDa.

In some embodiments, each hollow fiber within the fiber bundle has a molecular weight cut-off pore size of at least about 1 kDa, at least about 5 kDa, at least about 10 kDa, at least about 20 kDa, at least about 50 kDa, at least about 100 kDa, at least about 150 kDa, at least about 200 kDa, at least about 250 kDa, at least about 300 kDa, at least about 350 kDa, at least about 400 kDa, at least about 450 kDa, at least about 500 kDa, at least about 1,000 kDa, at least about 5,000 kDa, at least about 10,000 kDa, at least about 20,000 kDa, at least about 50,000 kDa, or at least about 100,000 kDa. In some embodiments, each hollow fiber within the fiber bundle has a molecular weight cut-off pore size of about 100,000 kDa or less, about 50,000 kDa or less, about 20,000 kDa or less, about 10,000 kDa or less, about 5,000 kDa or less, about 1,000 kDa or less, about 500 kDa or less, about 450 kDa or less, about 400 kDa or less, about 350 kDa or less, about 300 kDa or less, about 250 kDa or less, about 200 kDa or less, about 150 kDa or less, about 100 kDa or less, about 50 kDa or less, about 20 kDa or less, about 10 kDa or less, about 5 kDa or less, or about 1 kDa or less. In some embodiments, each hollow fiber within the fiber bundle has a molecular weight cut-off pore size between about 1 kDa and about 5 kDa, between about 1 kDa and about 10 kDa, between about 1 kDa and about 20 kDa, between about 1 kDa and about 50 kDa, between about 1 kDa and about 100 kDa, between about 1 kDa and about 200 kDa, between about 1 kDa and about 300 kDa, between about 1 kDa and about 400 kDa, between about 1 kDa and about 500 kDa, between about 1 kDa and about 1,000 kDa, between about 1 kDa and about 5,000 kDa, between about 1 kDa and about 10,000 kDa, between about 1 kDa and about 20,000 kDa, between about 1 kDa and about 50,000 kDa, between about 1 kDa and about 100,000 kDa, between about 10 kDa and about 50 kDa, between about 10 kDa and about 100 kDa, between about 10 kDa and about 200 kDa, between about 10 kDa and about 300 kDa, between about 10 kDa and about 400 kDa, between about 10 kDa and about 500 kDa, between about 10 kDa and about 1,000 kDa, between about 10 kDa and about 5,000 kDa, between about 10 kDa and about 10,000 kDa, between about 10 kDa and about 20,000 kDa, between about 10 kDa and about 50,000 kDa, between about 10 kDa and about 100,000 kDa, between about 100 kDa and about 200 kDa, between about 100 kDa and about 300 kDa, between about 100 kDa and about 400 kDa, between about 100 kDa and about 500 kDa, between about 100 kDa and about 1,000 kDa, between about 100 kDa and about 5,000 kDa, between about 100 kDa and about 10,000 kDa, between about 100 kDa and about 20,000 kDa, between about 100 kDa and about 50,000 kDa, between about 100 kDa and about 100,000 kDa, between about 500 kDa and about 1,000 kDa, between about 500 kDa and about 5,000 kDa, between about 500 kDa and about 10,000 kDa, between about 500 kDa and about 20,000 kDa, between about 500 kDa and about 50,000 kDa, between about 500 kDa and about 100,000 kDa, between about 1,000 kDa and about 5,000 kDa, between about 1,000 kDa and about 10,000 kDa, between about 1,000 kDa and about 20,000 kDa, between about 1,000 kDa and about 50,000 kDa, between about 1,000 kDa and about 100,000 kDa, between about 5,000 kDa and about 10,000 kDa, between about 5,000 kDa and about 20,000 kDa, between about 5,000 kDa and about 50,000 kDa, between about 5,000 kDa and about 100,000 kDa, between about 10,000 kDa and about 20,000 kDa, between about 10,000 kDa and about 50,000 kDa, between about 10,000 kDa and about 100,000 kDa, or between about 50,000 kDa and about 100,000 kDa.

In some embodiments, the center-to-center distance between any two hollow fibers (e.g., including directly adjacent hollow fibers) within the fiber bundle is relatively large. In certain embodiments, the center-to-center distance between any two hollow fibers within the fiber bundle at one or more points along a length of the fiber bundle is greater than or equal to an average outer diameter of the hollow fibers of the fiber bundle, greater than or equal to 1.5 times the average outer diameter, greater than or equal to 2 times the average outer diameter, greater than or equal to 2.5 times the average outer diameter, greater than or equal to 3 times the average outer diameter, greater than or equal to 3.5 times the average outer diameter, greater than or equal to 4 times the average outer diameter, greater than or equal to 4.5 times the average outer diameter, or greater than or equal to 5 times the average outer diameter. In some embodiments, the center-to-center distance between any two hollow fibers within the fiber bundle at one or more points along a length of the fiber bundle is between 1 and 1.5 times the average outer diameter, between 1 and 2 times the average outer diameter, between 1 and 2.5 times the average outer diameter, between 1 and 3 times the average outer diameter, between 1 and 3.5 times the average outer diameter, between 1 and 4 times the average outer diameter, between 1 and 4.5 times the average outer diameter, between 1 and 5 times the average outer diameter, between 2 and 2.5 times the average outer diameter, between 2 and 3 times the average outer diameter, between 2 and 3.5 times the average outer diameter, between 2 and 4 times the average outer diameter, between 2 and 4.5 times the average outer diameter, between 2 and 5 times the average outer diameter, between 2.5 and 3 times the average outer diameter, between 2.5 and 3.5 times the average outer diameter, between 2.5 and 4 times the average outer diameter, between 2.5 and 4.5 times the average outer diameter, between 2.5 and 5 times the average outer diameter, between 3 and 3.5 times the average outer diameter, between 3 and 4 times the average outer diameter, between 3 and 4.5 times the average outer diameter, between 3 and 5 times the average outer diameter, between 3.5 and 4 times the average outer diameter, between 3.5 and 4.5 times the average outer diameter, between 3.5 and 5 times the average outer diameter, between 4 and 4.5 times the average outer diameter, between 4 and 5 times the average outer diameter, or between 4.5 and 5 times the average outer diameter. The center-to-center distance between hollow fibers within a fiber bundle may be measured according to any method known in the art. For example, the center-to-center distance may be measured using calipers.

In certain embodiments, the center-to-center distance between any two hollow fibers within the fiber bundle at one or more points along a length of the fiber bundle is greater than or equal to a minimum diameter of the two hollow fibers, greater than or equal to 1.1 times a minimum diameter of the two hollow fibers, greater than or equal to 1.2 times a minimum diameter of the two hollow fibers, greater than or equal to 1.3 times a minimum diameter of the two hollow fibers, greater than or equal to 1.4 times a minimum diameter of the two hollow fibers, greater than or equal to 1.5 times a minimum diameter of the two hollow fibers, greater than or equal to 2 times a minimum diameter of the two hollow fibers, greater than or equal to 2.5 times a minimum diameter of the two hollow fibers, greater than or equal to 3 times a minimum diameter of the two hollow fibers, greater than or equal to 3.5 times a minimum diameter of the two hollow fibers, greater than or equal to 4 times a minimum diameter of the two hollow fibers, greater than or equal to 4.5 times a minimum diameter of the two hollow fibers, or greater than or equal to 5 times a minimum diameter of the two hollow fibers. In some embodiments, the center-to-center distance between any two hollow fibers within the fiber bundle at one or more points along a length of the fiber bundle is between 1 and 1.5 times a minimum diameter of the two hollow fibers, between 1 and 2 times a minimum diameter of the two hollow fibers, between 1 and 2.5 times a minimum diameter of the two hollow fibers, between 1 and 3 times a minimum diameter of the two hollow fibers, between 1 and 3.5 times a minimum diameter of the two hollow fibers, between 1 and 4 times a minimum diameter of the two hollow fibers, between 1 and 4.5 times a minimum diameter of the two hollow fibers, between 1 and 5 times a minimum diameter of the two hollow fibers, between 1.1 and 1.5 times a minimum diameter of the two hollow fibers, between 1.1 and 2 times a minimum diameter of the two hollow fibers, between 1.1 and 2.5 times a minimum diameter of the two hollow fibers, between 1.1 and 3 times a minimum diameter of the two hollow fibers, between 1.1 and 3.5 times a minimum diameter of the two hollow fibers, between 1.1 and 4 times a minimum diameter of the two hollow fibers, between 1.1 and 4.5 times a minimum diameter of the two hollow fibers, between 1.1 and 5 times a minimum diameter of the two hollow fibers, between 2 and 2.5 times a minimum diameter of the two hollow fibers, between 2 and 3 times a minimum diameter of the two hollow fibers, between 2 and 3.5 times a minimum diameter of the two hollow fibers, between 2 and 4 times a minimum diameter of the two hollow fibers, between 2 and 4.5 times a minimum diameter of the two hollow fibers, between 2 and 5 times a minimum diameter of the two hollow fibers, between 2.5 and 3 times a minimum diameter of the two hollow fibers, between 2.5 and 3.5 times a minimum diameter of the two hollow fibers, between 2.5 and 4 times a minimum diameter of the two hollow fibers, between 2.5 and 4.5 times a minimum diameter of the two hollow fibers, between 2.5 and 5 times a minimum diameter of the two hollow fibers, between 3 and 3.5 times a minimum diameter of the two hollow fibers, between 3 and 4 times a minimum diameter of the two hollow fibers, between 3 and 4.5 times a minimum diameter of the two hollow fibers, between 3 and 5 times a minimum diameter of the two hollow fibers, between 3.5 and 4 times a minimum diameter of the two hollow fibers, between 3.5 and 4.5 times a minimum diameter of the two hollow fibers, between 3.5 and 5 times a minimum diameter of the two hollow fibers, between 4 and 4.5 times a minimum diameter of the two hollow fibers, between 4 and 5 times a minimum diameter of the two hollow fibers, or between 4.5 and 5 times a minimum diameter of the two hollow fibers. A minimum diameter of a hollow fiber generally refers to a smallest cross-sectional dimension of the hollow fiber. A minimum diameter of two hollow fibers (e.g., a first hollow fiber, a second hollow fiber) generally refers to the smaller value of the minimum diameter of the first hollow fiber and the minimum diameter of the second hollow fiber.

In some embodiments, the center-to-center distance between any two hollow fibers within the fiber bundle at one or more points along a length of the fiber bundle is at least about 0.5 mm, at least about 1 mm, at least about 1.5 mm, at least about 2 mm, at least about 2.5 mm, at least about 3 mm, at least about 3.5 mm, at least about 4 mm, at least about 4.5 mm, or at least about 5 mm. In some embodiments, the center-to-center distance between any two hollow fibers within the fiber bundle at one or more points along a length of the fiber bundle is between about 0.5 mm and about 1 mm, between about 0.5 mm and about 1.5 mm, between about 0.5 mm and about 2 mm, between about 0.5 mm and about 2.5 mm, between about 0.5 mm and about 3 mm, between about 0.5 mm and about 3.5 mm, between about 0.5 mm and about 4 mm, between about 0.5 mm and about 4.5 mm, between about 0.5 mm and about 5 mm, between about 1 mm and about 2 mm, between about 1 mm and about 2.5 mm, between about 1 mm and about 3 mm, between about 1 mm and about 3.5 mm, between about 1 mm and about 4 mm, between about 1 mm and about 4.5 mm, between about 1 mm and about 5 mm, between about 2 mm and about 3 mm, between about 2 mm and about 3.5 mm, between about 2 mm and about 4 mm, between about 2 mm and about 4.5 mm, between about 2 mm and about 5 mm, between about 3 mm and about 5 mm, or between about 4 mm and about 5 mm.

In some embodiments, the average center-to-center distance of the hollow fibers of a fiber bundle (e.g., the number average of the distances between each hollow fiber and its nearest neighbor) is relatively large. In certain embodiments, the average center-to-center distance of the hollow fibers of a fiber bundle at one or more points along a length of the fiber bundle is greater than or equal to an average outer diameter of the hollow fibers of the fiber bundle, greater than or equal to 1.5 times the average outer diameter, greater than or equal to 2 times the average outer diameter, greater than or equal to 2.5 times the average outer diameter, greater than or equal to 3 times the average outer diameter, greater than or equal to 3.5 times the average outer diameter, greater than or equal to 4 times the average outer diameter, greater than or equal to 4.5 times the average outer diameter, or greater than or equal to 5 times the average outer diameter. In some embodiments, the average center-to-center distance of the hollow fibers of a fiber bundle at one or more points along a length of the fiber bundle is between 1 and 1.5 times the average outer diameter of the hollow fibers of the fiber bundle, between 1 and 2 times the average outer diameter, between 1 and 2.5 times the average outer diameter, between 1 and 3 times the average outer diameter, between 1 and 3.5 times the average outer diameter, between 1 and 4 times the average outer diameter, between 1 and 4.5 times the average outer diameter, between 1 and 5 times the average outer diameter, between 2 and 2.5 times the average outer diameter, between 2 and 3 times the average outer diameter, between 2 and 3.5 times the average outer diameter, between 2 and 4 times the average outer diameter, between 2 and 4.5 times the average outer diameter, between 2 and 5 times the average outer diameter, between 2.5 and 3 times the average outer diameter, between 2.5 and 3.5 times the average outer diameter, between 2.5 and 4 times the average outer diameter, between 2.5 and 4.5 times the average outer diameter, between 2.5 and 5 times the average outer diameter, between 3 and 3.5 times the average outer diameter, between 3 and 4 times the average outer diameter, between 3 and 4.5 times the average outer diameter, between 3 and 5 times the average outer diameter, between 3.5 and 4 times the average outer diameter, between 3.5 and 4.5 times the average outer diameter, between 3.5 and 5 times the average outer diameter, between 4 and 4.5 times the average outer diameter, between 4 and 5 times the average outer diameter, or between 4.5 and 5 times the average outer diameter.

In certain embodiments, the average center-to-center distance of the hollow fibers of a fiber bundle at one or more points along a length of the fiber bundle is greater than or equal to the minimum diameter of the hollow fibers, greater than or equal to 1.1 times the minimum diameter of the hollow fibers, greater than or equal to 1.2 times the minimum diameter of the hollow fibers, greater than or equal to 1.3 times the minimum diameter of the hollow fibers, greater than or equal to 1.4 times the minimum diameter of the hollow fibers, greater than or equal to 1.5 times the minimum diameter of the hollow fibers, greater than or equal to 2 times the minimum diameter of the hollow fibers, greater than or equal to 2.5 times the minimum diameter of the hollow fibers, greater than or equal to 3 times the minimum diameter of the hollow fibers, greater than or equal to 3.5 times the minimum diameter of the hollow fibers, greater than or equal to 4 times the minimum diameter of the hollow fibers, greater than or equal to 4.5 times the minimum diameter of the hollow fibers, or greater than or equal to 5 times the minimum diameter of the hollow fibers. In some embodiments, the average center-to-center distance of the hollow fibers of a fiber bundle at one or more points along a length of the fiber bundle is between 1 and 1.5 times the minimum diameter of the hollow fibers, between 1 and 2 times the minimum diameter of the hollow fibers, between 1 and 2.5 times the minimum diameter of the hollow fibers, between 1 and 3 times the minimum diameter of the hollow fibers, between 1 and 3.5 times the minimum diameter of the hollow fibers, between 1 and 4 times the minimum diameter of the hollow fibers, between 1 and 4.5 times the minimum diameter of the hollow fibers, between 1 and 5 times the minimum diameter of the hollow fibers, between 1.1 and 1.5 times the minimum diameter of the hollow fibers, between 1.1 and 2 times the minimum diameter of the hollow fibers, between 1.1 and 2.5 times the minimum diameter of the hollow fibers, between 1.1 and 3 times the minimum diameter of the hollow fibers, between 1.1 and 3.5 times the minimum diameter of the hollow fibers, between 1.1 and 4 times the minimum diameter of the hollow fibers, between 1.1 and 4.5 times the minimum diameter of the hollow fibers, between 1.1 and 5 times the minimum diameter of the hollow fibers, between 2 and 2.5 times the minimum diameter of the hollow fibers, between 2 and 3 times the minimum diameter of the hollow fibers, between 2 and 3.5 times the minimum diameter of the hollow fibers, between 2 and 4 times the minimum diameter of the hollow fibers, between 2 and 4.5 times the minimum diameter of the hollow fibers, between 2 and 5 times the minimum diameter of the hollow fibers, between 2.5 and 3 times the minimum diameter of the hollow fibers, between 2.5 and 3.5 times the minimum diameter of the hollow fibers, between 2.5 and 4 times the the minimum diameter of the hollow fibers, between 2.5 and 4.5 times the minimum diameter of the hollow fibers, between 2.5 and 5 times the minimum diameter of the hollow fibers, between 3 and 3.5 times the minimum diameter of the hollow fibers, between 3 and 4 times the minimum diameter of the hollow fibers, between 3 and 4.5 times the minimum diameter of the hollow fibers, between 3 and 5 times the minimum diameter of the hollow fibers, between 3.5 and 4 times the minimum diameter of the hollow fibers, between 3.5 and 4.5 times the minimum diameter of the hollow fibers, between 3.5 and 5 times the minimum diameter of the hollow fibers, between 4 and 4.5 times the minimum diameter of the hollow fibers, between 4 and 5 times the minimum diameter of the hollow fibers, or between 4.5 and 5 times the minimum diameter of the hollow fibers.

In some embodiments, the average center-to-center distance of the hollow fibers of a fiber bundle at one or more points along a length of the fiber bundle is at least about 0.5 mm, at least about 1 mm, at least about 1.5 mm, at least about 2 mm, at least about 2.5 mm, at least about 3 mm, at least about 3.5 mm, at least about 4 mm, at least about 4.5 mm, or at least about 5 mm. In some embodiments, the average center-to-center distance of the hollow fibers of a fiber bundle at one or more points along a length of the fiber bundle is between about 0.5 mm and about 1 mm, between about 0.5 mm and about 1.5 mm, between about 0.5 mm and about 2 mm, between about 0.5 mm and about 2.5 mm, between about 0.5 mm and about 3 mm, between about 0.5 mm and about 3.5 mm, between about 0.5 mm and about 4 mm, between about 0.5 mm and about 4.5 mm, between about 0.5 mm and about 5 mm, between about 1 mm and about 2 mm, between about 1 mm and about 2.5 mm, between about 1 mm and about 3 mm, between about 1 mm and about 3.5 mm, between about 1 mm and about 4 mm, between about 1 mm and about 4.5 mm, between about 1 mm and about 5 mm, between about 2 mm and about 3 mm, between about 2 mm and about 3.5 mm, between about 2 mm and about 4 mm, between about 2 mm and about 4.5 mm, between about 2 mm and about 5 mm, between about 3 mm and about 5 mm, or between about 4 mm and about 5 mm.

In some embodiments, the filter probe has a relatively small diameter. As used herein, the diameter of the filter probe refers to the largest cross-sectional dimension of the filter probe. In certain cases, the filter probe has a diameter of about 50 mm or less, about 45 mm or less, about 40 mm or less, about 35 mm or less, about 30 mm or less, about 25 mm or less, about 20 mm or less, about 15 mm or less, about 13.4 mm or less, about 10 mm or less, or about 5 mm or less. In some embodiments, the filter probe has a diameter between about 5 mm and about 10 mm, between about 5 mm and about 13.4 mm, between about 5 mm and about 20 mm, between about 5 mm and about 30 mm, between about 5 mm and about 40 mm, between about 5 mm and about 50 mm, between about 10 mm and about 20 mm, between about 10 mm and about 30 mm, between about 10 mm and about 40 mm, between about 10 mm and about 50 mm, between about 20 mm and about 30 mm, between about 20 mm and about 40 mm, between about 20 mm and about 50 mm, between about 30 mm and about 40 mm, between about 30 mm and about 50 mm, or between about 40 mm and about 50 mm.

In some embodiments, a filter probe having a certain diameter comprises a relatively small number of hollow fibers. In some instances, the filter probe has a diameter of at least about 5 mm, at least about 10 mm, at least about 13.4 mm, at least about 15 mm, at least about 20 mm, or at least about 25 mm. In certain embodiments, the filter probe having a diameter of at least about 5 mm, at least about 10 mm, at least about 15 mm, at least about 20 mm, or at least about 25 mm comprises 2500 or fewer fibers, 2200 or fewer fibers, 2000 or fewer fibers, 1500 or fewer fibers, 1000 or fewer fibers, 500 or fewer fibers, 100 or fewer fibers, 50 or fewer fibers, 10 or fewer fibers, 5 or fewer fibers, or 2 or fewer fibers. In some embodiments, the filter probe having a diameter of at least about 5 mm, at least about 10 mm, at least about 13.4 mm, at least about 15 mm, at least about 20 mm, or at least about 25 mm comprises between 2 and 5 fibers, between 2 and 10 fibers, between 2 and 50 fibers, between 2 and 100 fibers, between 2 and 500 fibers, between 2 and 1000 fibers, between 2 and 1500 fibers, between 2 and 2000 fibers, between 2 and 2200 fibers, between 2 and 2500 fibers, between 10 and 50 fibers, between 10 and 100 fibers, between 10 and 500 fibers, between 10 and 1000 fibers, between 10 and 1500 fibers, between 10 and 2000 fibers, between 10 and 2200 fibers, between 10 and 2500 fibers, between 50 and 100 fibers, between 50 and 500 fibers, between 50 and 1000 fibers, between 50 and 1500 fibers, between 50 and 2000 fibers, between 50 and 2200 fibers, between 50 and 2500 fibers, between 100 and 500 fibers, between 100 and 1000 fibers, between 100 and 1500 fibers, between 100 and 2000 fibers, between 100 and 2200 fibers, between 100 and 2500 fibers, between 500 and 1000 fibers, between 500 and 1500 fibers, between 500 and 2000 fibers, between 500 and 2200 fibers, between 500 and 2500 fibers, between 1000 and 1500 fibers, between 1000 and 2000 fibers, between 1000 and 2200 fibers, between 1000 and 2500 fibers, between 1500 and 2000 fibers, between 1500 and 2200 fibers, between 1500 and 2500 fibers, or between 2000 and 2500 fibers.

The filter probe may have any suitable length (e.g., the longest dimension of the filter probe). In certain embodiments, the filter probe has a length that is relatively large compared to a height of a bioreactor (e.g., the largest vertical dimension of the reaction chamber of the bioreactor). In some embodiments, the filter probe has a length that is at least about 10%, at least about 20%, at least about 30%, at least about 40%, at least about 50%, at least about 60%, at least about 70%, at least about 80%, at least about 90%, or at least about 95% of the height of the bioreactor. In some embodiments, the filter probe has a length that is between about 10% and about 50% of the height of the bioreactor, between about 10% and about 60% of the height of the bioreactor, between about 10% and about 70% of the height of the bioreactor, between about 10% and about 80% of the height of the bioreactor, between about 10% and about 90% of the height of the bioreactor, between about 10% and about 95% of the height of the bioreactor, between about 20% and about 50% of the height of the bioreactor, between about 20% and about 60% of the height of the bioreactor, between about 20% and about 70% of the height of the bioreactor, between about 20% and about 80% of the height of the bioreactor, between about 20% and about 90% of the height of the bioreactor, between about 20% and about 95% of the height of the bioreactor, between about 50% and about 60% of the height of the bioreactor, between about 50% and about 70% of the height of the bioreactor, between about 50% and about 80% of the height of the bioreactor, between about 50% and about 90% of the height of the bioreactor, between about 50% and about 95% of the height of the bioreactor, between about 60% and about 70% of the height of the bioreactor, between about 60% and about 80% of the height of the bioreactor, between about 60% and about 90% of the height of the bioreactor, between about 60% and about 95% of the height of the bioreactor, between about 70% and about 80% of the height of the bioreactor, between about 70% and about 90% of the height of the bioreactor, between about 70% and about 95% of the height of the bioreactor, between about 80% and about 90% of the height of the bioreactor, between about 80% and about 95% of the height of the bioreactor, between about 90% and about 95% of the height of the bioreactor, or between about 95% and about 100% of the height of the bioreactor.

The filter probe may have any suitable shape. In some embodiments, the filter probe has a cross section that is substantially circular, substantially hexagonal, substantially elliptical, substantially square, substantially rectangular, or substantially triangular. In certain embodiments, the filter probe is substantially a cylinder, a hexagonal prism, a rectangular prism, or a triangular prism.

In some embodiments, the filter bundle of the filter probe comprises a structured segment. As used herein, the structured segment of the filter bundle refers to a segment comprising the majority of the active filtering length over which the plurality of hollow fibers is exposed to the external environment (e.g., bioreactor fluid) during use and in which the hollow fibers have relatively large center-to-center distances—in comparison to inlet and outlet regions where the hollow fibers are typically more densely packed with lesser center-to-center spacing. In some instances, for example, the center-to-center distance between any two hollow fibers within the structured segment is greater than or equal to the average outer diameter, greater than or equal to 1.5 times the average outer diameter, greater than or equal to 2 times the average outer diameter, greater than or equal to 2.5 times the average outer diameter, greater than or equal to 3 times the average outer diameter, greater than or equal to 3.5 times the average outer diameter, greater than or equal to 4 times the average outer diameter, greater than or equal to 4.5 times the average outer diameter, or greater than or equal to 5 times the average outer diameter. In some embodiments, the center-to-center distance between any two hollow fibers within the structured segment is between 1 and 1.5 times the average outer diameter, between 1 and 2 times the average outer diameter, between 1 and 2.5 times the average outer diameter, between 1 and 3 times the average outer diameter, between 1 and 3.5 times the average outer diameter, between 1 and 4 times the average outer diameter, between 1 and 4.5 times the average outer diameter, between 1 and 5 times the average outer diameter, between 2 and 2.5 times the average outer diameter, between 2 and 3 times the average outer diameter, between 2 and 3.5 times the average outer diameter, between 2 and 4 times the average outer diameter, between 2 and 4.5 times the average outer diameter, between 2 and 5 times the average outer diameter, between 2.5 and 3 times the average outer diameter, between 2.5 and 3.5 times the average outer diameter, between 2.5 and 4 times the average outer diameter, between 2.5 and 4.5 times the average outer diameter, between 2.5 and 5 times the average outer diameter, between 3 and 3.5 times the average outer diameter, between 3 and 4 times the average outer diameter, between 3 and 4.5 times the average outer diameter, between 3 and 5 times the average outer diameter, between 3.5 and 4 times the average outer diameter, between 3.5 and 4.5 times the average outer diameter, between 3.5 and 5 times the average outer diameter, between 4 and 4.5 times the average outer diameter, between 4 and 5 times the average outer diameter, or between 4.5 and 5 times the average outer diameter.

In certain embodiments, the center-to-center distance between any two hollow fibers within the structured segment is greater than or equal to a minimum diameter of the two hollow fibers, greater than or equal to 1.1 times a minimum diameter of the two hollow fibers, greater than or equal to 1.2 times a minimum diameter of the two hollow fibers, greater than or equal to 1.3 times a minimum diameter of the two hollow fibers, greater than or equal to 1.4 times a minimum diameter of the two hollow fibers, greater than or equal to 1.5 times a minimum diameter of the two hollow fibers, greater than or equal to 2 times a minimum diameter of the two hollow fibers, greater than or equal to 2.5 times a minimum diameter of the two hollow fibers, greater than or equal to 3 times a minimum diameter of the two hollow fibers, greater than or equal to 3.5 times a minimum diameter of the two hollow fibers, greater than or equal to 4 times a minimum diameter of the two hollow fibers, greater than or equal to 4.5 times a minimum diameter of the two hollow fibers, or greater than or equal to 5 times a minimum diameter of the two hollow fibers. In some embodiments, the center-to-center distance between any two hollow fibers within the structured segment is between 1 and 1.5 times a minimum diameter of the two hollow fibers, between 1 and 2 times a minimum diameter of the two hollow fibers, between 1 and 2.5 times a minimum diameter of the two hollow fibers, between 1 and 3 times a minimum diameter of the two hollow fibers, between 1 and 3.5 times a minimum diameter of the two hollow fibers, between 1 and 4 times a minimum diameter of the two hollow fibers, between 1 and 4.5 times a minimum diameter of the two hollow fibers, between 1 and 5 times a minimum diameter of the two hollow fibers, between 1.1 and 1.5 times a minimum diameter of the two hollow fibers, between 1.1 and 2 times a minimum diameter of the two hollow fibers, between 1.1 and 2.5 times a minimum diameter of the two hollow fibers, between 1.1 and 3 times a minimum diameter of the two hollow fibers, between 1.1 and 3.5 times a minimum diameter of the two hollow fibers, between 1.1 and 4 times a minimum diameter of the two hollow fibers, between 1.1 and 4.5 times a minimum diameter of the two hollow fibers, between 1.1 and 5 times a minimum diameter of the two hollow fibers, between 2 and 2.5 times a minimum diameter of the two hollow fibers, between 2 and 3 times a minimum diameter of the two hollow fibers, between 2 and 3.5 times a minimum diameter of the two hollow fibers, between 2 and 4 times a minimum diameter of the two hollow fibers, between 2 and 4.5 times a minimum diameter of the two hollow fibers, between 2 and 5 times a minimum diameter of the two hollow fibers, between 2.5 and 3 times a minimum diameter of the two hollow fibers, between 2.5 and 3.5 times a minimum diameter of the two hollow fibers, between 2.5 and 4 times a minimum diameter of the two hollow fibers, between 2.5 and 4.5 times a minimum diameter of the two hollow fibers, between 2.5 and 5 times a minimum diameter of the two hollow fibers, between 3 and 3.5 times a minimum diameter of the two hollow fibers, between 3 and 4 times a minimum diameter of the two hollow fibers, between 3 and 4.5 times a minimum diameter of the two hollow fibers, between 3 and 5 times a minimum diameter of the two hollow fibers, between 3.5 and 4 times a minimum diameter of the two hollow fibers, between 3.5 and 4.5 times a minimum diameter of the two hollow fibers, between 3.5 and 5 times a minimum diameter of the two hollow fibers, between 4 and 4.5 times a minimum diameter of the two hollow fibers, between 4 and 5 times a minimum diameter of the two hollow fibers, or between 4.5 and 5 times a minimum diameter of the two hollow fibers. A minimum diameter of a hollow fiber generally refers to a smallest cross-sectional dimension of the hollow fiber. A minimum diameter of two hollow fibers (e.g., a first hollow fiber, a second hollow fiber) generally refers to the smaller value of the minimum diameter of the first hollow fiber and the minimum diameter of the second hollow fiber.

In some embodiments, the center-to-center distance between any two hollow fibers within the structured segment is at least about 0.5 mm, at least about 1 mm, at least about 1.5 mm, at least about 2 mm, at least about 2.5 mm, at least about 3 mm, at least about 3.5 mm, at least about 4 mm, at least about 4.5 mm, or at least about 5 mm. In some embodiments, the center-to-center distance between any two hollow fibers within the structured segment is between about 0.5 mm and about 1 mm, between about 0.5 mm and about 1.5 mm, between about 0.5 mm and about 2 mm, between about 0.5 mm and about 2.5 mm, between about 0.5 mm and about 3 mm, between about 0.5 mm and about 3.5 mm, between about 0.5 mm and about 4 mm, between about 0.5 mm and about 4.5 mm, between about 0.5 mm and about 5 mm, between about 1 mm and about 2 mm, between about 1 mm and about 2.5 mm, between about 1 mm and about 3 mm, between about 1 mm and about 3.5 mm, between about 1 mm and about 4 mm, between about 1 mm and about 4.5 mm, between about 1 mm and about 5 mm, between about 2 mm and about 3 mm, between about 2 mm and about 3.5 mm, between about 2 mm and about 4 mm, between about 2 mm and about 4.5 mm, between about 2 mm and about 5 mm, between about 3 mm and about 5 mm, or between about 4 mm and about 5 mm.

The structured segment may have any suitable length. In some embodiments, the structured segment has a length of at least about 10 mm, at least about 20 mm, at least about 50 mm, at least about 100 mm, at least about 150 mm, at least about 200 mm, at least about 250 mm, at least about 300 mm, at least about 350 mm, at least about 400 mm, at least about 450 mm, or at least about 500 mm. In some embodiments, the structured segment has a length of about 500 mm or less, about 450 mm or less, about 400 mm or less, about 350 mm or less, about 300 mm or less, about 250 mm or less, about 200 mm or less, about 150 mm or less, about 100 mm or less, about 50 mm or less, about 20 mm or less, or about 10 mm or less. In some embodiments, the structured segment has a length between about 10 mm and about 20 mm, between about 10 mm and about 50 mm, between about 10 mm and about 100 mm, between about 10 mm and about 150 mm, between about 10 mm and about 200 mm, between about 10 mm and about 250 mm, between about 10 mm and about 300 mm, between about 10 mm and about 350 mm, between about 10 mm and about 400 mm, between about 10 mm and about 450 mm, between about 10 mm and about 500 mm, between about 50 mm and about 100 mm, between about 50 mm and about 150 mm, between about 50 mm and about 200 mm, between about 50 mm and about 250 mm, between about 50 mm and about 300 mm, between about 50 mm and about 350 mm, between about 50 mm and about 400 mm, between about 50 mm and about 450 mm, between about 50 mm and about 500 mm, between about 100 mm and about 150 mm, between about 100 mm and about 200 mm, between about 100 mm and about 250 mm, between about 100 mm and about 300 mm, between about 100 mm and about 350 mm, between about 100 mm and about 400 mm, between about 100 mm and about 450 mm, between about 100 mm and about 500 mm, between about 200 mm and about 250 mm, between about 200 mm and about 300 mm, between about 200 mm and about 350 mm, between about 200 mm and about 400 mm, between about 200 mm and about 450 mm, between about 200 mm and about 500 mm, between about 300 mm and about 500 mm, or between about 400 nm and about 500 nm.

In some embodiments, the structured segment has a length that is relatively large compared to a height of a bioreactor (e.g., the largest vertical dimension of the reaction chamber of the bioreactor). In some embodiments, the structured segment has a length that is at least about 10%, at least about 20%, at least about 30%, at least about 40%, at least about 50%, at least about 60%, at least about 70%, at least about 80%, at least about 90%, or at least about 95% of the height of the bioreactor. In some embodiments, the structured segment has a length that is between about 10% and about 50% of the height of the bioreactor, between about 10% and about 60% of the height of the bioreactor, between about 10% and about 70% of the height of the bioreactor, between about 10% and about 80% of the height of the bioreactor, between about 10% and about 90% of the height of the bioreactor, between about 10% and about 95% of the height of the bioreactor, between about 20% and about 50% of the height of the bioreactor, between about 20% and about 60% of the height of the bioreactor, between about 20% and about 70% of the height of the bioreactor, between about 20% and about 80% of the height of the bioreactor, between about 20% and about 90% of the height of the bioreactor, between about 20% and about 95% of the height of the bioreactor, between about 50% and about 60% of the height of the bioreactor, between about 50% and about 70% of the height of the bioreactor, between about 50% and about 80% of the height of the bioreactor, between about 50% and about 90% of the height of the bioreactor, between about 50% and about 95% of the height of the bioreactor, between about 60% and about 70% of the height of the bioreactor, between about 60% and about 80% of the height of the bioreactor, between about 60% and about 90% of the height of the bioreactor, between about 60% and about 95% of the height of the bioreactor, between about 70% and about 80% of the height of the bioreactor, between about 70% and about 90% of the height of the bioreactor, between about 70% and about 95% of the height of the bioreactor, between about 80% and about 90% of the height of the bioreactor, between about 80% and about 95% of the height of the bioreactor, between about 90% and about 95% of the height of the bioreactor, or between about 95% and about 100% of the height of the bioreactor.

The structured segment may have any suitable diameter. In some embodiments, the diameter of the structured segment is at least about 5 mm, at least about 10 mm, at least about 15 mm, at least about 20 mm, at least about 25 mm, at least about 30 mm, at least about 35 mm, at least about 40 mm, at least about 45 mm, or at least about 50 mm. In some embodiments, the diameter of the structured segment is about 50 mm or less, about 45 mm or less, about 40 mm or less, about 35 mm or less, about 30 mm or less, about 25 mm or less, about 20 mm or less, about 15 mm or less, about 10 mm or less, or about 5 mm or less. In some embodiments, the diameter of the structured segment is between about 5 mm and about 10 mm, between about 5 mm and about 20 mm, between about 5 mm and about 30 mm, between about 5 mm and about 40 mm, between about 5 mm and about 50 mm, between about 10 mm and about 20 mm, between about 10 mm and about 30 mm, between about 10 mm and about 40 mm, between about 10 mm and about 50 mm, between about 20 mm and about 30 mm, between about 20 mm and about 40 mm, between about 20 mm and about 50 mm, between about 30 mm and about 40 mm, between about 30 mm and about 50 mm, or between about 40 mm and about 50 mm.

In some embodiments, the fiber bundle has a relatively high surface area within the structured segment. In some embodiments, the fiber bundle has a surface area within the structured segment of at least about 20 cm$^2$, at least about 50 cm$^2$, at least about 100 cm$^2$, at least about 150 cm$^2$, at least about 200 cm$^2$, at least about 250 cm$^2$, at least about 300 cm$^2$, at least about 350 cm$^2$, at least about 400 cm$^2$, at least about 450 cm$^2$, at least about 500 cm$^2$, at least about 1000 cm$^2$, at least about 5000 cm$^2$, at least about 10,000 cm$^2$, at least about 15,000 cm$^2$, or at least about 20,000 cm$^2$, at least about 30,000 cm$^2$, at least about 40,000 cm$^2$, or at least about 50,000 cm$^2$. In some embodiments, the fiber bundle has a surface area within the structured segment between about 20 cm$^2$ and about 50 cm$^2$, between about 20 cm$^2$ and about 100 cm$^2$, between about 20 cm$^2$ and about 150 cm$^2$, between about 20 cm$^2$ and about 200 cm$^2$, between about 20 cm$^2$ and about 250 cm$^2$, between about 20 cm$^2$ and about 300 cm$^2$, between about 20 cm$^2$ and about 350 cm$^2$, between about 20 cm$^2$ and about 400 cm$^2$, between about 20 cm$^2$ and about 450 cm$^2$, between about 20 cm$^2$ and about 500 cm$^2$, between about 20 cm$^2$ and about 1000 cm$^2$, between about 20 cm$^2$ and about 5000 cm$^2$, between about 20 cm$^2$ and about 10,000 cm$^2$, between about 20 cm$^2$ and about 15,000 cm$^2$, between about 20 cm$^2$ and about 20,000 cm$^2$, between about 20 cm$^2$ and about 30,000 cm$^2$, between about 20 cm$^2$ and about 40,000 cm$^2$, between about 20 cm$^2$ and about 50,000 cm$^2$, between about 100 cm$^2$ and about 200 cm$^2$, between about 100 cm$^2$ and about 250 cm$^2$, between about 100 cm$^2$ and about 300 cm$^2$, between about 100 cm$^2$ and about 350 cm$^2$, between about 100 cm$^2$ and about 400 cm$^2$, between about 100 cm$^2$ and about 450 cm$^2$, between about 100 cm$^2$ and about 500 cm$^2$, between about 100 cm$^2$ and about 1000 cm$^2$, between about 100 cm$^2$ and about 5000 cm$^2$, between about 100 cm$^2$ and about 10,000 cm$^2$, between about 100 cm$^2$ and about 15,000 cm$^2$, between about 100 cm$^2$ and about 20,000 cm$^2$, between about 100 cm$^2$ and about 30,000 cm$^2$, between about 100 cm$^2$ and about 40,000 cm$^2$, between about 100 cm$^2$ and about 50,000 cm$^2$, between about 500 cm$^2$ and about 1000 cm$^2$, between about 500 cm$^2$ and about 5000 cm$^2$, between about 500 cm$^2$ and about 10,000 cm$^2$, between about 500 cm$^2$ and about 15,000 cm$^2$, between about 500 cm$^2$ and about 20,000 cm$^2$, between about 500 cm$^2$ and about 30,000 cm$^2$, between about 500 cm$^2$ and about 40,000 cm$^2$, between about 500 cm$^2$ and about 50,000 cm$^2$, between about 1000 cm$^2$ and about 5000 cm$^2$, between about 1000 cm$^2$ and about 10,000 cm$^2$, between about 1000 cm$^2$ and about 15,000 cm$^2$, between about 1000 cm$^2$ and about 20,000 cm$^2$, between about 1000 cm$^2$ and about 30,000 cm$^2$, between about 1000 cm$^2$ and about 40,000 cm$^2$, between about 1000 cm$^2$ and about 50,000 cm$^2$, between about 5000 cm$^2$ and about 10,000 cm$^2$, between about 5000 cm$^2$ and about 15,000 cm$^2$, between about 5000 cm$^2$ and about 20,000 cm$^2$, between about 5000 cm$^2$ and about 30,000 cm$^2$, between about 5000 cm$^2$ and about 40,000 cm$^2$, between about 5000 cm$^2$ and about 50,000 cm$^2$, between about 10,000 cm$^2$ and about 20,000 cm$^2$, between about 10,000 cm$^2$ and about 30,000 cm$^2$, between about 10,000 cm$^2$ and about 40,000 cm$^2$, between about 10,000 cm$^2$ and about 50,000 cm$^2$, or between about 10,000 cm$^2$ and about 50,000 cm$^2$.

The hollow fibers of the fiber bundle may be positioned in any suitable arrangement. In some embodiments, the hollow fibers of the fiber bundle are arranged in an array. According to certain embodiments, the array may be a hexagonal, linear, annular, or square array.

The hollow fibers of the fiber bundle may comprise any suitable material. In some embodiments, at least one hollow fiber within the fiber bundle comprises a polymer. In some instances, each hollow fiber within the fiber bundle comprises a polymer. Non-limiting examples of suitable polymers include polytetrafluoroethylene (PTFE), polyvinylidene fluoride (PVDF), and polyethersulfone (PES) and other polysulfones. In some embodiments, at least one hollow fiber within the fiber bundle comprises a ceramic and/or a metal (e.g., a porous metal). In some instances, each hollow fiber within the fiber bundle comprises a ceramic and/or a metal (e.g., a porous metal). A non-limiting example of a suitable ceramic is alumina. Examples of suitable metals include, but are not limited to, steel, platinum, aluminum, titanium, gold, and alloys thereof. In some cases, the hollow fibers of the fiber bundle comprise materials that are chemically stable in the presence of a cell culture medium. In certain cases, the hollow fibers of the fiber bundle are chemically stable in the presence of methanol and/or glycerol.

In some embodiments, at least one hollow fiber of the fiber bundle is associated with (e.g., fluidically connected to) a secondary filter (e.g., a device configured to further filter a filtrate stream flowing through the lumen of a hollow fiber). In some cases, the presence of a secondary filter associated with (e.g., fluidically connected to) a hollow fiber may advantageously maintain filtration capacity of the hollow fiber in the event of a failure of the fiber (e.g., a loss of integrity that results in cells flowing into the lumen of the hollow fiber). This may be particularly advantageous in systems in which filtrate streams from individual hollow fibers are consolidated before exiting the filter probe, as failure of a single hollow fiber in such systems may result in loss of overall filtration capacity and/or introduction of cells into at least one filtrate stream.

In some embodiments, at least about 10%, at least about 25%, at least about 50%, at least about 75%, at least about 90%, at least about 95%, at least about 99%, or about 100% of the hollow fibers of the fiber bundle are associated with (e.g., fluidically connected to) a secondary filter. In some embodiments, one or more hollow fibers associated with a secondary filter are associated with different secondary filters. In certain embodiments, each hollow fiber associated with a secondary filter is associated with a different secondary filter. In some cases, associating each hollow fiber with a different secondary filter may advantageously minimize any filtration capacity loss resulting from failure of any single hollow fiber. In certain instances, one or more hollow fibers associated with a secondary filter are associated with the same secondary filter. In some cases, each hollow fiber associated with a secondary filter is associated with the same secondary filter (e.g., a single secondary filter positioned downstream of the filter probe).

In some embodiments, a secondary filter associated with (e.g., fluidically connected to) a hollow fiber is positioned externally to the hollow fiber. In such embodiments, the external secondary filter may be any suitable type of filter (e.g., a membrane filter). In some embodiments, a secondary filter associated with a hollow fiber is positioned internally to the hollow fiber. In certain instances, the secondary filter may form an integral portion of the hollow fiber. In certain cases, for example, a hollow fiber may comprise a first region (e.g., a region at least partially within the structured segment of the filter probe) exposed to the contents of the bioreactor and a second region isolated from the contents of the bioreactor (e.g., by filter housing and/or a potting region). In certain cases, the second region of the hollow fiber may function as a secondary filter.

Figure 6:
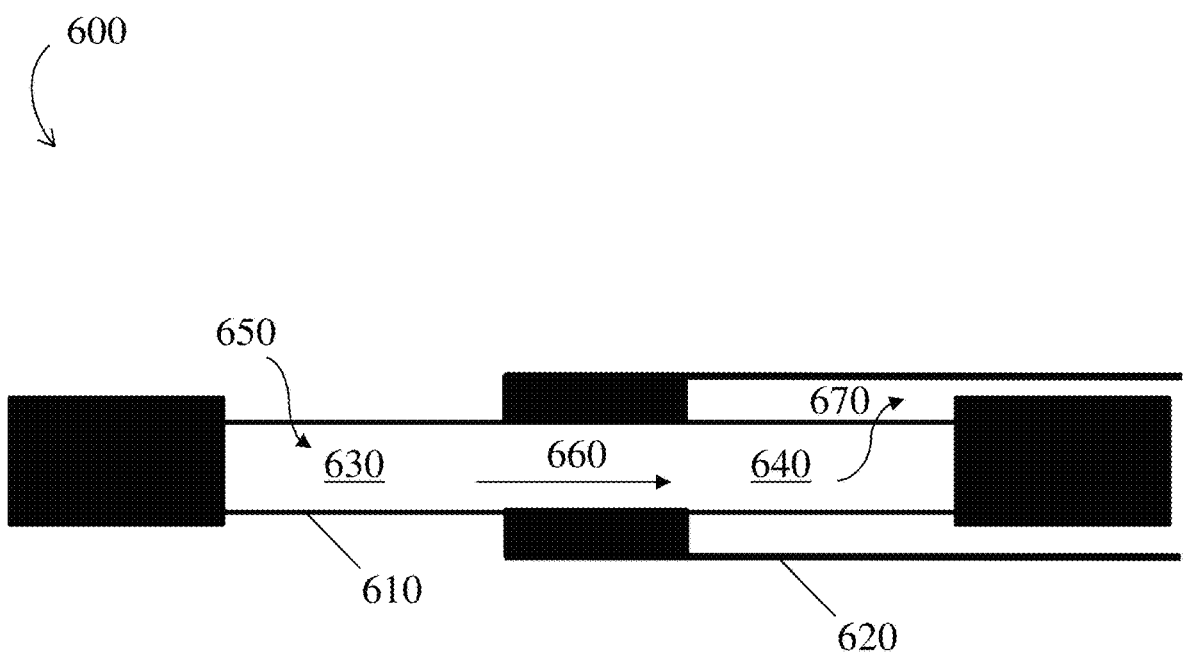
FIG. 6 is, according to some embodiments, a schematic illustration of an exemplary filter probe comprising a hollow fiber associated with a secondary filter.

A schematic diagram of an exemplary hollow fiber associated with a secondary filter is illustrated in FIG. 6. As shown in FIG. 6, filter probe 600 comprises hollow fiber 610 and filter housing 620. In some embodiments, filter probe 600 further comprises first potting region 680 at a first end of hollow fiber 610 and/or second potting region 690 at a second, opposite end of hollow fiber 610. First potting region 680 and/or second potting region 690 may prevent a fluid stream (e.g., a cell suspension stream) from entering the central cavity (i.e., lumen) of hollow fiber 610 through one or more ends of hollow fiber 610. Hollow fiber 610 comprises first region 630 (e.g., comprising a structured segment), which is exposed to the contents of a bioreactor, and second region 640. As shown in FIG. 6, second region 640 is isolated from the contents of the bioreactor by filter housing 620, first potting region 680, and second potting region 690. In some cases, hollow fiber 610 is fluidically sealed to filter housing 620 such that there are no gaps between hollow fiber 610 and filter housing 620 through which a fluid may pass.

In operation, a cell suspension stream comprising biological cells, at least one biologically-produced product, and a cell culture medium may be directed to flow through first region 630 of hollow fiber 610 to produce a first filtrate stream, as indicated by arrow 650. According to some embodiments, the first filtrate stream comprises the at least one biologically-produced product and is lean in the biological cells relative to the cell suspension stream. In some embodiments, the first filtrate stream is directed to flow through the lumen of hollow fiber 610 from first region 630 to second region 640, as indicated by arrow 660. The first filtrate stream may then be directed to flow from second region 640 to the interior of filter housing 620, as indicated by arrow 670, to produce a second filtrate stream. First region 630 thus acts as a primary filter, and second region 640 acts as a secondary filter associated with hollow fiber 610. In the event of loss of integrity of first region 630, biomass (e.g., biological cells) within the cell suspension stream may be permitted to enter first region 630 and flow along the lumen of hollow fiber 610, but may be prevented from exiting hollow fiber 610 through second region 640.

In some embodiments, the second region of a hollow fiber may have a relatively high surface area to mitigate the effects of pore fouling and concentration polarization (e.g., due to lack of exposure to the bioreactor flow field). In certain embodiments, at least one hollow fiber of the fiber bundle comprises a second region having a surface area of at least about 10 $cm^2$, at least about 50 $cm^2$, at least about 100 $cm^2$, at least about 200 $cm^2$, at least about 500 $cm^2$, at least about 800 $cm^2$, at least about 1000 $cm^2$, at least about 5000 $cm^2$, at least about 8000 $cm^2$, at least about 10,000 $cm^2$, at least about 20,000 $cm^2$, at least about 50,000 $cm^2$, at least about 80,000 $cm^2$, or at least about 100,000 $cm^2$. In some embodiments, at least one hollow fiber of the fiber bundle comprises a second region having a surface area between about 10 $cm^2$ and about 50 $cm^2$, between about 10 $cm^2$ and about 100 $cm^2$, between about 10 $cm^2$ and about 200 $cm^2$, between about 10 $cm^2$ and about 500 $cm^2$, between about 10 $cm^2$ and about 800 $cm^2$, between about 10 $cm^2$ and about 1000 $cm^2$, between about 10 $cm^2$ and about 5000 $cm^2$, between about 10 $cm^2$ and about 8000 $cm^2$, between about 10 $cm^2$ and about 10,000 $cm^2$, between about 10 $cm^2$ and about 20,000 $cm^2$, between about 10 $cm^2$ and about 50,000 $cm^2$, between about 10 $cm^2$ and about 80,000 $cm^2$, between about 10 $cm^2$ and about 100,000 $cm^2$, between about 50 $cm^2$ and about 100 $cm^2$, between about 50 $cm^2$ and about 200 $cm^2$, between about 50 $cm^2$ and about 500 $cm^2$, between about 50 $cm^2$ and about 800 $cm^2$, between about 50 $cm^2$ and about 1000 $cm^2$, between about 50 $cm^2$ and about 5000 $cm^2$, between about 50 $cm^2$ and about 8000 $cm^2$, between about 50 $cm^2$ and about 10,000 $cm^2$, between about 50 $cm^2$ and about 20,000 $cm^2$, between about 50 $cm^2$ and about 50,000 $cm^2$, between about 50 $cm^2$ and about 80,000 $cm^2$, between about 50 $cm^2$ and about 100,000 $cm^2$, between about 100 $cm^2$ and about 500 $cm^2$, between about 100 $cm^2$ and about 1000 $cm^2$, between about 100 $cm^2$ and about 5000 $cm^2$, between about 100 $cm^2$ and about 8000 $cm^2$, between about 100 $cm^2$ and about 10,000 $cm^2$, between about 100 $cm^2$ and about 20,000 $cm^2$, between about 100 $cm^2$ and about 50,000 $cm^2$, between about 100 $cm^2$ and about 80,000 $cm^2$, between about 100 $cm^2$ and about 100,000 $cm^2$, between about 500 $cm^2$ and about 1000 $cm^2$, between about 500 $cm^2$ and about 5000 $cm^2$, between about 500 $cm^2$ and about 8000 $cm^2$, between about 500 $cm^2$ and about 10,000 $cm^2$, between about 500 $cm^2$ and about 20,000 $cm^2$, between about 500 $cm^2$ and about 50,000 $cm^2$, between about 500 $cm^2$ and about 80,000 $cm^2$, between about 500 $cm^2$ and about 100,000 $cm^2$, between about 1000 $cm^2$ and about 5000 $cm^2$, between about 1000 $cm^2$ and about 8000 $cm^2$, between about 1000 $cm^2$ and about 10,000 $cm^2$, between about 1000 $cm^2$ and about 20,000 $cm^2$, between about 1000 $cm^2$ and about 50,000 $cm^2$, between about 1000 $cm^2$ and about 80,000 $cm^2$, between about 1000 $cm^2$ and about 100,000 $cm^2$, between about 5000 $cm^2$ and about 10,000 $cm^2$, between about 5000 $cm^2$ and about 20,000 $cm^2$, between about 5000 $cm^2$ and about 50,000 $cm^2$, between about 5000 $cm^2$ and about 80,000 $cm^2$, between about 5000 $cm^2$ and about 100,000 $cm^2$, between about 10,000 $cm^2$ and about 20,000 $cm^2$, between about 10,000 $cm^2$ and about 50,000 $cm^2$, between about 10,000 cm² and about 80,000 cm², between about 10,000 cm² and about 100,000 cm², or between about 50,000 cm² and about 100,000 cm².

In certain embodiments, each hollow fiber of the fiber bundle comprises a second region having a surface area of at least about 10 cm², at least about 50 cm², at least about 100 cm², at least about 200 cm², at least about 500 cm², at least about 800 cm², at least about 1000 cm², at least about 5000 cm², at least about 8000 cm², at least about 10,000 cm², at least about 20,000 cm², at least about 50,000 cm², at least about 80,000 cm², or at least about 100,000 cm². In some embodiments, each hollow fiber of the fiber bundle comprises a second region having a surface area between about 10 cm² and about 50 cm², between about 10 cm² and about 100 cm², between about 10 cm² and about 200 cm², between about 10 cm² and about 500 cm², between about 10 cm² and about 800 cm², between about 10 cm² and about 1000 cm², between about 10 cm² and about 5000 cm², between about 10 cm² and about 8000 cm², between about 10 cm² and about 10,000 cm², between about 10 cm² and about 20,000 cm², between about 10 cm² and about 50,000 cm², between about 10 cm² and about 80,000 cm², between about 10 cm² and about 100,000 cm², between about 50 cm² and about 100 cm², between about 50 cm² and about 200 cm², between about 50 cm² and about 500 cm², between about 50 cm² and about 800 cm², between about 50 cm² and about 1000 cm², between about 50 cm² and about 5000 cm², between about 50 cm² and about 8000 cm², between about 50 cm² and about 10,000 cm², between about 50 cm² and about 20,000 cm², between about 50 cm² and about 50,000 cm², between about 50 cm² and about 80,000 cm², between about 50 cm² and about 100,000 cm², between about 100 cm² and about 500 cm², between about 100 cm² and about 1000 cm², between about 100 cm² and about 5000 cm², between about 100 cm² and about 8000 cm², between about 100 cm² and about 10,000 cm², between about 100 cm² and about 20,000 cm², between about 100 cm² and about 50,000 cm², between about 100 cm² and about 80,000 cm², between about 100 cm² and about 100,000 cm², between about 500 cm² and about 1000 cm², between about 500 cm² and about 5000 cm², between about 500 cm² and about 8000 cm², between about 500 cm² and about 10,000 cm², between about 500 cm² and about 20,000 cm², between about 500 cm² and about 50,000 cm², between about 500 cm² and about 80,000 cm², between about 500 cm² and about 100,000 cm², between about 1000 cm² and about 5000 cm², between about 1000 cm² and about 8000 cm², between about 1000 cm² and about 10,000 cm², between about 1000 cm² and about 20,000 cm², between about 1000 cm² and about 50,000 cm², between about 1000 cm² and about 80,000 cm², between about 1000 cm² and about 100,000 cm², between about 5000 cm² and about 10,000 cm², between about 5000 cm² and about 20,000 cm², between about 5000 cm² and about 50,000 cm², between about 5000 cm² and about 80,000 cm², between about 5000 cm² and about 100,000 cm², between about 10,000 cm² and about 20,000 cm², between about 10,000 cm² and about 50,000 cm², between about 10,000 cm² and about 80,000 cm², between about 10,000 cm² and about 100,000 cm², or between about 50,000 cm² and about 100,000 cm².

In some embodiments, the second region of a hollow fiber comprises a plurality of pores. The plurality of pores of the second region of the hollow fiber may have an average pore size that is the same or different from the average pore size of the plurality of pores of the first region of the hollow fiber. In some embodiments, at least one hollow fiber within the fiber bundle comprises a second region comprising a plurality of pores having an average pore size of at least about 0.025 µm, at least about 0.05 µm, at least about 0.08 µm, at least about 0.1 µm, at least about 0.2 µm, at least about 0.3 µm, at least about 0.4 µm, at least about 0.5 µm, at least about 0.8 µm, at least about 1 µm, at least about 1.5 µm, or at least about 2.0 µm. In certain instances, at least one hollow fiber within the fiber bundle comprises a second region comprising a plurality of pores having an average pore size of about 2.0 µm or less, about 1.5 µm or less, about 1 µm or less, about 0.8 µm or less, about 0.5 µm or less, about 0.4 µm or less, about 0.3 µm or less, about 0.2 µm or less, about 0.1 µm or less, about 0.08 µm or less, about 0.05 µm or less, or about 0.025 µm or less. In some embodiments, at least one hollow fiber within the fiber bundle comprises a second region comprising a plurality of pores having an average pore size in a range from about 0.025 µm to about 0.05 µm, about 0.025 µm to about 0.1 µm, about 0.025 µm to about 0.5 µm, about 0.025 µm to about 1 µm, about 0.025 µm to about 1.5 µm, about 0.025 µm to about 2.0 µm, about 0.05 µm to about 0.1 µm, about 0.05 µm to about 0.5 µm, about 0.05 µm to about 1 µm, about 0.05 µm to about 1.5 µm, about 0.05 µm to about 2.0 µm, about 0.1 µm to about 0.5 µm, about 0.1 µm to about 1 µm, about 0.1 µm to about 1.5 µm, about 0.1 µm to about 2.0 µm, about 0.2 µm to about 0.5 µm, about 0.2 µm to about 1 µm, about 0.2 µm to about 1.5 µm, about 0.2 µm to about 2.0 µm, about 0.5 µm to about 1 µm, about 0.5 µm to about 1.5 µm, about 0.5 µm to about 2.0 µm, or about 1.0 µm to about 2.0 µm.

In some embodiments, each hollow fiber within the fiber bundle comprises a second region having an average pore size of at least about 0.025 µm, at least about 0.05 µm, at least about 0.08 µm, at least about 0.1 µm, at least about 0.2 µm, at least about 0.3 µm, at least about 0.4 µm, at least about 0.5 µm, at least about 0.8 µm, at least about 1 µm, at least about 1.5 µm, or at least about 2.0 µm. In some embodiments, each hollow fiber within the fiber bundle comprises a second region having an average pore size of about 2.0 µm or less, about 1.5 µm or less, about 1 µm or less, about 0.8 µm or less, about 0.5 µm or less, about 0.4 µm or less, about 0.3 µm or less, about 0.2 µm or less, about 0.1 µm or less, about 0.08 µm or less, about 0.05 µm or less, or about 0.025 µm or less. In some embodiments, each hollow fiber within the fiber bundle comprises a second region having an average pore size in a range from about 0.025 µm to about 0.05 µm, about 0.025 µm to about 0.1 µm, about 0.025 µm to about 0.5 µm, about 0.025 µm to about 1 µm, about 0.025 µm to about 1.5 µm, about 0.025 µm to about 2.0 µm, about 0.05 µm to about 0.1 µm, about 0.05 µm to about 0.5 µm, about 0.05 µm to about 1 µm, about 0.05 µm to about 1.5 µm, about 0.05 µm to about 2.0 µm, about 0.1 µm to about 0.5 µm, about 0.1 µm to about 1 µm, about 0.1 µm to about 1.5 µm, about 0.1 µm to about 2.0 µm, about 0.2 µm to about 0.5 µm, about 0.2 µm to about 1 µm, about 0.2 µm to about 1.5 µm, about 0.2 µm to about 2.0 µm, about 0.5 µm to about 1 µm, about 0.5 µm to about 1.5 µm, about 0.5 µm to about 2.0 µm, or about 1.0 µm to about 2.0 µm.

The plurality of pores of the second region of the hollow fiber may have a molecular weight cut-off pore size that is the same or different from the molecular weight cut-off pore size of the first region of the hollow fiber. In some embodiments, at least one hollow fiber within the fiber bundle comprises a second region having a molecular weight cut-off pore size of at least about 1 kDa, at least about 5 kDa, at least about 10 kDa, at least about 20 kDa, at least about 50 kDa, at least about 100 kDa, at least about 150 kDa, at least about 200 kDa, at least about 250 kDa, at least about 300 kDa, at least about 350 kDa, at least about 400 kDa, at least about 450 kDa, at least about 500 kDa, at least about 1,000 kDa, at least about 5,000 kDa, at least about 10,000 kDa, at least about 20,000 kDa, at least about 50,000 kDa, or at least about 100,000 kDa. In some embodiments, at least one hollow fiber within the fiber bundle comprises a second region having a molecular weight cut-off pore size of about 100,000 kDa or less, about 50,000 kDa or less, about 20,000 kDa or less, about 10,000 kDa or less, about 5,000 kDa or less, about 1,000 kDa or less, about 500 kDa or less, about 450 kDa or less, about 400 kDa or less, about 350 kDa or less, about 300 kDa or less, about 250 kDa or less, about 200 kDa or less, about 150 kDa or less, about 100 kDa or less, about 50 kDa or less, about 20 kDa or less, about 10 kDa or less, about 5 kDa or less, or about 1 kDa or less. In some embodiments, at least one hollow fiber within the fiber bundle comprises a second region having a molecular weight cut-off pore size between about 1 kDa and about 5 kDa, between about 1 kDa and about 10 kDa, between about 1 kDa and about 20 kDa, between about 1 kDa and about 50 kDa, between about 1 kDa and about 100 kDa, between about 1 kDa and about 200 kDa, between about 1 kDa and about 300 kDa, between about 1 kDa and about 400 kDa, between about 1 kDa and about 500 kDa, between about 1 kDa and about 1,000 kDa, between about 1 kDa and about 5,000 kDa, between about 1 kDa and about 10,000 kDa, between about 1 kDa and about 20,000 kDa, between about 1 kDa and about 50,000 kDa, between about 1 kDa and about 100,000 kDa, between about 10 kDa and about 50 kDa, between about 10 kDa and about 100 kDa, between about 10 kDa and about 200 kDa, between about 10 kDa and about 300 kDa, between about 10 kDa and about 400 kDa, between about 10 kDa and about 500 kDa, between about 10 kDa and about 1,000 kDa, between about 10 kDa and about 5,000 kDa, between about 10 kDa and about 10,000 kDa, between about 10 kDa and about 20,000 kDa, between about 10 kDa and about 50,000 kDa, between about 10 kDa and about 100,000 kDa, between about 100 kDa and about 200 kDa, between about 100 kDa and about 300 kDa, between about 100 kDa and about 400 kDa, between about 100 kDa and about 500 kDa, between about 100 kDa and about 1,000 kDa, between about 100 kDa and about 5,000 kDa, between about 100 kDa and about 10,000 kDa, between about 100 kDa and about 20,000 kDa, between about 100 kDa and about 50,000 kDa, between about 100 kDa and about 100,000 kDa, between about 500 kDa and about 1,000 kDa, between about 500 kDa and about 5,000 kDa, between about 500 kDa and about 10,000 kDa, between about 500 kDa and about 20,000 kDa, between about 500 kDa and about 50,000 kDa, between about 500 kDa and about 100,000 kDa, between about 1,000 kDa and about 5,000 kDa, between about 1,000 kDa and about 10,000 kDa, between about 1,000 kDa and about 20,000 kDa, between about 1,000 kDa and about 50,000 kDa, between about 1,000 kDa and about 100,000 kDa, between about 5,000 kDa and about 10,000 kDa, between about 5,000 kDa and about 20,000 kDa, between about 5,000 kDa and about 50,000 kDa, between about 5,000 kDa and about 100,000 kDa, between about 10,000 kDa and about 20,000 kDa, between about 10,000 kDa and about 50,000 kDa, between about 10,000 kDa and about 100,000 kDa, or between about 50,000 kDa and about 100,000 kDa.

In some embodiments, each hollow fiber within the fiber bundle comprises a second region having a molecular weight cut-off pore size of at least about 1 kDa, at least about 5 kDa, at least about 10 kDa, at least about 20 kDa, at least about 50 kDa, at least about 100 kDa, at least about 150 kDa, at least about 200 kDa, at least about 250 kDa, at least about 300 kDa, at least about 350 kDa, at least about 400 kDa, at least about 450 kDa, at least about 500 kDa, at least about 1,000 kDa, at least about 5,000 kDa, at least about 10,000 kDa, at least about 20,000 kDa, at least about 50,000 kDa, or at least about 100,000 kDa. In some embodiments, each hollow fiber within the fiber bundle comprises a second region having a molecular weight cut-off pore size of about 100,000 kDa or less, about 50,000 kDa or less, about 20,000 kDa or less, about 10,000 kDa or less, about 5,000 kDa or less, about 1,000 kDa or less, about 500 kDa or less, about 450 kDa or less, about 400 kDa or less, about 350 kDa or less, about 300 kDa or less, about 250 kDa or less, about 200 kDa or less, about 150 kDa or less, about 100 kDa or less, about 50 kDa or less, about 20 kDa or less, about 10 kDa or less, about 5 kDa or less, or about 1 kDa or less. In some embodiments, each hollow fiber within the fiber bundle comprises a second region having a molecular weight cut-off pore size between about 1 kDa and about 5 kDa, between about 1 kDa and about 10 kDa, between about 1 kDa and about 20 kDa, between about 1 kDa and about 50 kDa, between about 1 kDa and about 100 kDa, between about 1 kDa and about 200 kDa, between about 1 kDa and about 300 kDa, between about 1 kDa and about 400 kDa, between about 1 kDa and about 500 kDa, between about 1 kDa and about 1,000 kDa, between about 1 kDa and about 5,000 kDa, between about 1 kDa and about 10,000 kDa, between about 1 kDa and about 20,000 kDa, between about 1 kDa and about 50,000 kDa, between about 1 kDa and about 100,000 kDa, between about 10 kDa and about 50 kDa, between about 10 kDa and about 100 kDa, between about 10 kDa and about 200 kDa, between about 10 kDa and about 300 kDa, between about 10 kDa and about 400 kDa, between about 10 kDa and about 500 kDa, between about 10 kDa and about 1,000 kDa, between about 10 kDa and about 5,000 kDa, between about 10 kDa and about 10,000 kDa, between about 10 kDa and about 20,000 kDa, between about 10 kDa and about 50,000 kDa, between about 10 kDa and about 100,000 kDa, between about 100 kDa and about 200 kDa, between about 100 kDa and about 300 kDa, between about 100 kDa and about 400 kDa, between about 100 kDa and about 500 kDa, between about 100 kDa and about 1,000 kDa, between about 100 kDa and about 5,000 kDa, between about 100 kDa and about 10,000 kDa, between about 100 kDa and about 20,000 kDa, between about 100 kDa and about 50,000 kDa, between about 100 kDa and about 100,000 kDa, between about 500 kDa and about 1,000 kDa, between about 500 kDa and about 5,000 kDa, between about 500 kDa and about 10,000 kDa, between about 500 kDa and about 20,000 kDa, between about 500 kDa and about 50,000 kDa, between about 500 kDa and about 100,000 kDa, between about 1,000 kDa and about 5,000 kDa, between about 1,000 kDa and about 10,000 kDa, between about 1,000 kDa and about 20,000 kDa, between about 1,000 kDa and about 50,000 kDa, between about 1,000 kDa and about 100,000 kDa, between about 5,000 kDa and about 10,000 kDa, between about 5,000 kDa and about 20,000 kDa, between about 5,000 kDa and about 50,000 kDa, between about 5,000 kDa and about 100,000 kDa, between about 10,000 kDa and about 20,000 kDa, between about 10,000 kDa and about 50,000 kDa, between about 10,000 kDa and about 100,000 kDa, or between about 50,000 kDa and about 100,000 kDa.

In some embodiments, the filter probe is capable of withstanding a relatively high pressure differential. A person of ordinary skill in the art would understand a pressure differential to refer to a difference between pressure in a lumen of a hollow fiber of the filter probe and pressure in the bioreactor. In some cases, the pressure differential may be negative due to pressurization of the bioreactor above atmospheric pressure (i.e., about 1 bar) and/or application of a vacuum to the lumen of the hollow fiber. In some embodiments, the filter probe is capable of withstanding a pressure differential of at least about −5 bar, at least about −4 bar, at least about −3 bar, at least about −2 bar, at least about −1 bar, at least about −0.5 bar, at least about 0 bar, at least about 0.5 bar, at least about 1 bar, at least about 2 bar, at least about 3 bar, at least about 4 bar, or at least about 5 bar. In some embodiments, the filter probe is capable of withstanding a pressure differential of about 5 bar or less, about 4 bar or less, about 3 bar or less, about 2 bar or less, about 1 bar or less, about 0.5 bar or less, about 0 bar or less, about −0.5 bar or less, about −1 bar or less, about −2 bar or less, about −3 bar or less, about −4 bar or less, or about −5 bar or less. In some embodiments, the filter probe is capable of withstanding a pressure differential between about −5 bar and about −1 bar, between about −5 bar and about 0 bar, between about −5 bar and about 1 bar, between about −5 bar and about 5 bar, between about −1 bar and about 0 bar, between about −1 bar and about 1 bar, between about −1 bar and about 5 bar, between about 0 bar and about 1 bar, between about 0 bar and about 5 bar, between about 1 bar and about 2 bar, between about 1 bar and about 3 bar, between about 1 bar and about 4 bar, between about 1 bar and about 5 bar, between about 2 bar and about 5 bar, between about 3 bar and about 5 bar, or between about 4 bar and about 5 bar.

In some embodiments, the filter probe is capable of withstanding sterilization. In certain instances, for example, the filter probe is capable of withstanding exposure to radiation (e.g., gamma radiation), steam, dry heat, and/or sterilizing chemicals (e.g., ethylene oxide, nitrogen dioxide, ozone, hydrogen peroxide). In some embodiments, the filter probe is capable of withstanding relatively high gamma radiation. In some instances, the ability of the filter probe to withstand relatively high gamma radiation may be advantageous at least in part because it would allow the filter probe to be safely sterilized using gamma radiation. In some embodiments, the filter probe is capable of withstanding at least about 10 kGy, at least about 20 kGy, at least about 30 kGy, at least about 40 kGy, at least about 50 kGy, or at least about 100 kGy of gamma radiation. In some embodiments, the filter probe is capable of withstanding between about 10 kGy and about 50 kGy, between about 10 kGy and about 100 kGy, between about 20 kGy and about 50 kGy, between about 20 kGy and about 100 kGy, or between 50 kGy and about 100 kGy of gamma radiation. Any method known in the art may be used to determine whether the filter probe is capable of withstanding a certain amount of gamma radiation. For example, post-irradiation testing to ensure integrity may be conducted.

In some embodiments, the filter probe further comprises a central shaft (e.g., shaft 120 in FIG. 1). The central shaft may have any suitable size and shape. In certain instances, for example, the central shaft is substantially cylindrical. In some embodiments, the filter probe further comprises one or more spacing elements (e.g., spacing elements 130A-B in FIG. 1). In some cases, the one or more spacing elements encircle the central shaft. In some instances, for example, the one or more spacing elements comprise a central clearance hole (e.g., a hole extending from a first surface of the spacing element to a second, opposing surface of the spacing element) through which the shaft may be inserted. In some instances, the one or more spacing elements further comprise clearance holes for at least one hollow fiber of the fiber bundle. In some instances, the one or more spacing elements comprise clearance holes for each hollow fiber of the fiber bundle. The one or more spacing elements may, in some instances, maintain a desired spacing between hollow fibers (e.g., a spacing greater than the average outer diameter of the plurality of hollow fibers). The one or more spacing elements may also, in certain instances, provide mechanical stability. A schematic illustration of an exemplary spacing element is shown in FIG. 3B.

The filter probe may comprise any number of spacing elements. In some embodiments, the filter probe comprises at least 1, at least 2, at least 3, at least 4, at least 5, at least 10, at least 15, at least 20, or at least 50 spacing elements. In some embodiments, the filter probe comprises between 1 and 2, between 1 and 3, between 1 and 4, between 1 and 5, between 1 and 10, between 1 and 15, between 1 and 20, between 1 and 50, between 2 and 3, between 2 and 4, between 2 and 5, between 2 and 10, between 2 and 15, between 2 and 20, between 2 and 50, between 3 and 4, between 3 and 5, between 3 and 10, between 3 and 15, between 3 and 20, between 3 and 50, between 4 and 5, between 4 and 10, between 4 and 15, between 4 and 20, between 4 and 50, between 5 and 10, between 5 and 15, between 5 and 20, between 5 and 50, between 10 and 15, between 10 and 20, between 10 and 50, or between 20 and 50 spacing elements.

In some embodiments, the filter probe further comprises an end piece. The end piece may comprise one or more separate pieces. In some embodiments, the end piece comprises a hub and/or a mounting collar. FIG. 3C shows schematic illustrations of exemplary hub 330A and exemplary mounting collar 330B. In some instances, hub 330A comprises a central clearance hole through which the central shaft of the filter probe may be inserted. In some instances, hub 330A further comprises open areas for hollow fibers to pass through. In some embodiments, hollow fibers passing through the hub may have a relatively high packing density.

In some cases, hub 330A may be physically connected (e.g., directly physically connected) to mounting collar 330B. For example, hub 330A may be welded or epoxied to mounting collar 330B. In some cases, hub 330A distributes forces from fluid applied to the hollow fibers and shaft of the filter probe to mounting collar 330B. In certain embodiments, mounting collar 330B accepts hub 330A and necks down the hollow fibers for potting. Necking may advantageously avoid the need for double-walled features, which may increase hollow fiber count without increasing the outer diameter of the filter probe. At the top of the mounting collar, the hollow fibers may be potted and cleaved. In some cases, the mounting collar may be threaded and attached to another shaft to permit placement at a desired depth within the bioreactor fluid.

In some embodiments, a fully assembled filter probe (e.g., a filter probe that does not require further assembly) may be inserted into a bioreactor (e.g., through a port of the bioreactor). In certain other embodiments, a first portion of a filter probe may be inserted into a bioreactor (e.g., through a port of the bioreactor), and one or more additional portions of the filter probe may be separately installed in the bioreactor (e.g., through a bottom portion of the bioreactor). In some embodiments, one or more steps (e.g., inserting part of one portion into part of another portion, turning part of a portion) may be required to complete assembly of the filter probe. In some cases, there may be advantages associated with separately inserting two or more portions of a filter probe into a bioreactor. For example, small-scale bioreactors may have ports with a small cross-sectional area, which may necessitate tight tolerances (e.g., in the diameter of the filter probe in order to maximize fiber area). In some cases, filter probes with a tight tolerance for diameter may be susceptible to human error. For example, human error during insertion of a filter probe (e.g., a fully assembled filter probe having a tight tolerance for diameter) through a port of a bioreactor may cause one or more fibers of the filter probe to physically contact a bioreactor component, which may cause damage to the one or more fibers and result in loss of filter integrity. In some cases, a filter probe comprising two or more portions, one or more of which may be installed in a way other than insertion through a port of a bioreactor (e.g., a port in a headplate of a bioreactor), may advantageously minimize damage caused by human error during insertion of the filter probe into the bioreactor.

Figure 7A:
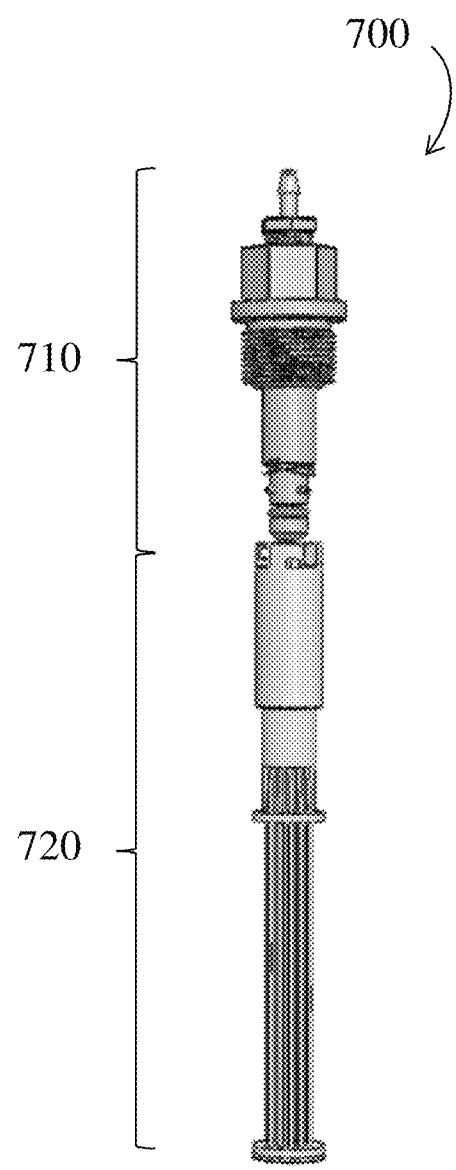
FIG. 7A is a schematic illustration of an exemplary filter probe comprising a first portion and a second portion, according to some embodiments.
Figure 7B:
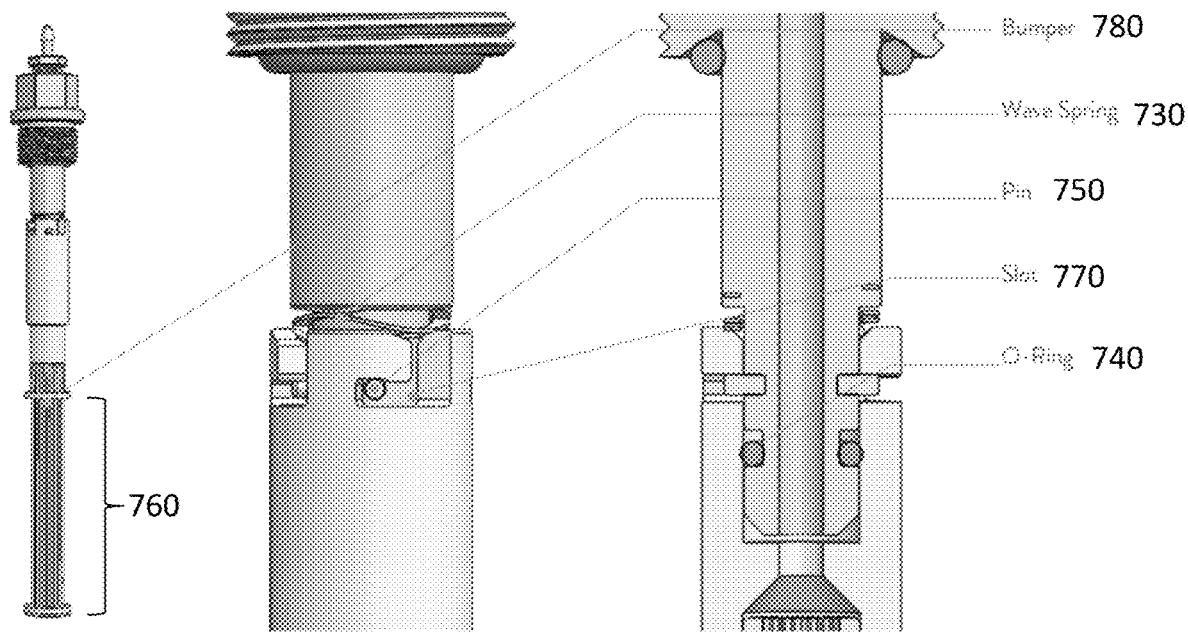
FIG. 7B is a schematic illustration of parts of a first portion and a second portion of an exemplary filter probe, according to some embodiments.

FIG. 7A is a schematic illustration of an exemplary filter probe comprising first portion (e.g., upper portion) 710 and second portion (e.g., lower portion) 720. FIG. 7B provides detailed views of portions of certain components of first portion 710 and second portion 720, particularly those components relating to a mechanism connecting first portion 710 to second portion 720. As shown in FIG. 7B, first portion 710 comprises wave spring 730, O-ring 740, and four retention pins 750. In some embodiments, a first portion of a filter probe may be configured to inserted into a port of a bioreactor (e.g., a PG13.5 port). The first portion may be formed from any suitable material, including but not limited to a metal, a metal alloy (e.g., stainless steel), or a polymer. As shown in FIG. 7B, second portion 720 comprises hollow fibers 760, four slots 770, and bumper 780.

Figures 7C, 7D, 7E:
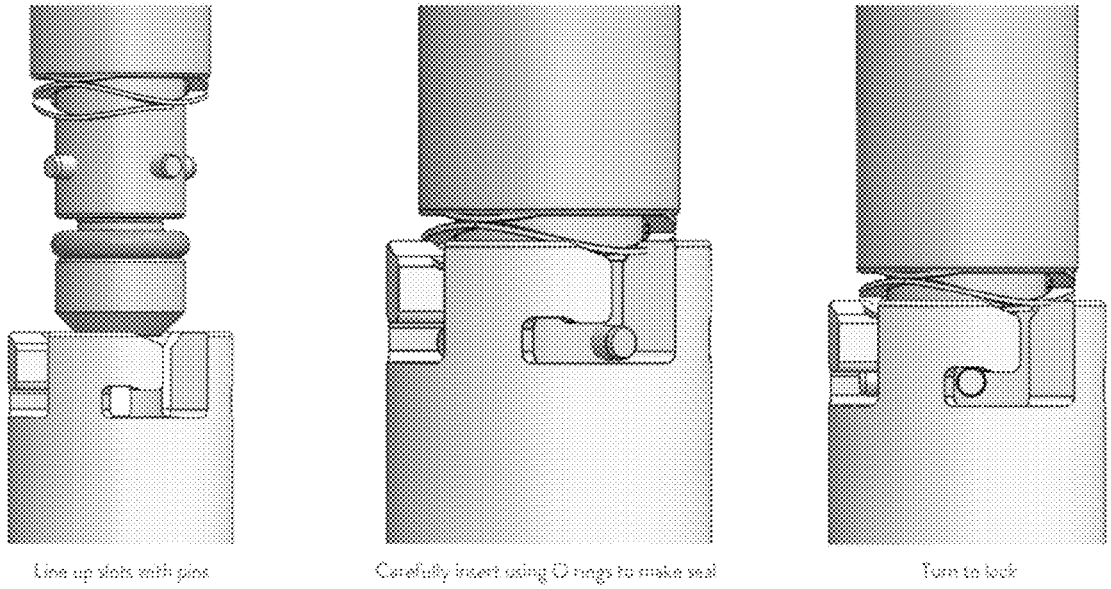
FIG. 7C is a schematic illustration of an exemplary first step of connecting a first portion and a second portion of an exemplary filter probe, according to some embodiments.
FIG. 7D is a schematic illustration of an exemplary second step of connecting a first portion and a second portion of an exemplary filter probe, according to some embodiments.
FIG. 7E is a schematic illustration of an exemplary third step of connecting a first portion and a second portion of an exemplary filter probe, according to some embodiments.

FIGS. 7C-7E illustrate exemplary steps for connecting first portion 710 and second portion 720. As shown in FIG. 7C, the four retention pins 750 of first portion 710 may be aligned with the four slots 770 of segment 720. As shown in FIG. 7D, first portion 710 may then be inserted into second portion 720, and O-ring 740 may provide a fluidic seal separating any fluid flowing through filter probe 700 from the environment of a bioreactor (e.g., the headspace of a bioreactor). As shown in FIG. 7E, first portion 710 and/or second portion 720 may be at least partially turned (e.g., engaged in a quarter turn) to connect the two segments. In some embodiments, bumper 780 may reduce the possibility of an external object (e.g., the appendages of a person assembling first portion 710 and second portion 720) contacting and potentially damaging hollow fibers 760 of second portion 720 during the assembly process.

Figure 7F:
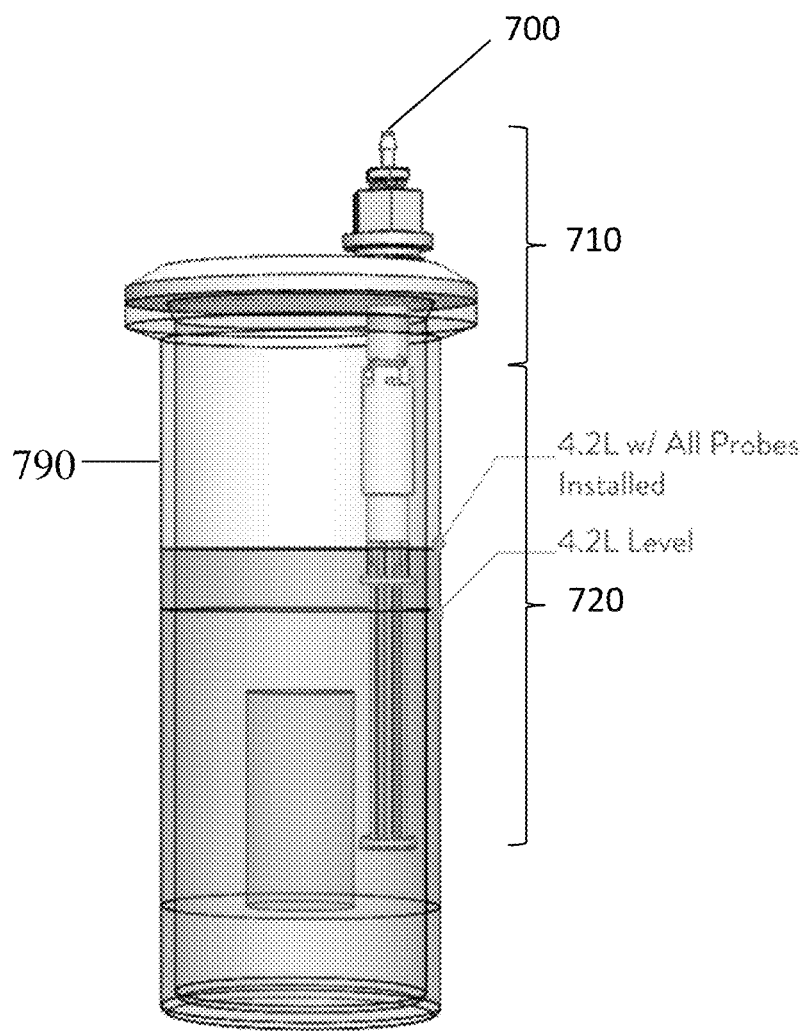
FIG. 7F is a schematic illustration of an exemplary system comprising a bioreactor and an exemplary filter probe comprising a first portion and a second portion, according to some embodiments.

FIG. 7F shows a system comprising fully assembled filter probe 700 installed in bioreactor 790. Filter probe 700 may be assembled according to any suitable assembly process.

In one exemplary process, first portion 710 and second portion 720 may be installed in bioreactor 790, and bioreactor 790 may subsequently be sterilized.

In another exemplary process, first portion 710 may be installed in bioreactor 790. Bioreactor 790 may subsequently undergo sterilization. Bioreactor 790 may then be opened in a cleanroom environment, and second portion 720 may be installed.

In yet another exemplary process, second portion 720 may be installed in bioreactor 790. First portion 710 may subsequently be inserted into bioreactor 790 (e.g., through a port of bioreactor 790).

In some cases, first portion 710 may be connected to second portion 720 through the steps shown in FIGS. 7C-7E (e.g., aligning retention pins and slots and turning at least a part of first portion 710 and/or second portion 720). In some embodiments, wave spring 730, retention pins 750, and/or slots 770 may allow second portion 720 to remain in position and avoid being dislodged by any vibrations (e.g., vibrations transmitted through a fluid stream and/or a component of a bioreactor).

In some embodiments, the filter probe is configured to rotate (e.g., about its longitudinal axis). In certain cases, rotation of the filter probe (e.g., about its longitudinal axis) may advantageously prevent fouling and/or facilitate defouling of hollow fibers of the filter probe (e.g., by increasing shear rate). In some embodiments, the filter probe comprises one or more bearings to facilitate rotation. The filter probe may be driven by any type of suitable drive (e.g., a magnetic drive, a direct drive) and may be configured to rotate in a clockwise direction and/or a counterclockwise direction. In some embodiments, the filter probe may be rotated at a speed of at least about 10 revolutions per minute (RPM), at least about 20 RPM, at least about 50 RPM, at least about 100 RPM, at least about 150 RPM, at least about 200 RPM, at least about 300 RPM, at least about 400 RPM, at least about 500 RPM, at least about 600 RPM, at least about 700 RPM, at least about 800 RPM, at least about 900 RPM, at least about 1,000 RPM, at least about 2,000 RPM, or at least about 5,000 RPM. In some embodiments, the filter probe may be rotated at a speed between about 10 RPM and about 50 RPM, between about 10 RPM and about 100 RPM, between about 10 RPM and about 500 RPM, between about 10 RPM and about 1,000 RPM, between about 10 RPM and about 2,000 RPM, between about 10 RPM and about 5,000 RPM, between about 100 RPM and about 500 RPM, between about 100 RPM and about 1,000 RPM, between about 100 RPM and about 2,000 RPM, between about 100 RPM and about 5,000 RPM, between about 500 RPM and about 1,000 RPM, between about 500 RPM and about 2,000 RPM, between about 500 RPM and about 5,000 RPM, or between about 1,000 RPM and about 5,000 RPM.

Certain embodiments described herein are directed to kits. In some embodiments, a kit comprises a filter probe described herein and a container (e.g., a storage container). The storage container may be any container large enough to house the filter probe.

Certain embodiments described herein are directed to systems comprising a bioreactor and a filter probe. In some instances, a filter probe described herein may be used in a system comprising a bioreactor. Suitable systems comprising a bioreactor include those described in U.S. Provisional Patent Application Ser. No. 62/480,428, filed Apr. 1, 2017, and entitled "Process/Equipment for High Concentration/Throughput Rapid Perfusion Based Production of Biotherapeutics," and in a U.S. patent application entitled "Level Sensing Systems for Perfusion-Based Systems and Methods for Manufacturing Biologically-Produced Products," both of which are incorporated herein by reference in their entireties for all purposes.

In some embodiments, the bioreactor is a perfusion bioreactor. A perfusion bioreactor generally refers to a bioreactor that is continuously operated (e.g., an input stream and an output stream have a non-zero flow rate over a specified period of time) such that at least a portion of the cells are retained within a reaction chamber of the bioreactor but at least a portion of the cell culture medium is continuously removed (and replenished). In some instances, a perfusion bioreactor may be associated with certain advantages over a fed-batch bioreactor (e.g., a bioreactor in which cells, media, and products remain in the bioreactor until the end of a run), such as higher cell concentrations and product yields, lower levels of accumulated waste, immediate availability and reduced degradation (e.g., oxidation, aggregation, deamidation, proteolysis) of biologically-produced products (e.g., expressed proteins) for purification, and more consistent expression profiles. In some cases, immediate availability of biologically-produced products may allow rescue of a desired product in the event of contamination. In addition, due to the higher cell concentrations that can be achieved in perfusion bioreactors, a perfusion bioreactor having a certain level of productivity may have a substantially smaller physical size than a corresponding fed-batch reactor having the same level of productivity. In some cases, the smaller physical size of perfusion bioreactors may make them attractive candidates for single-use, disposable biomanufacturing systems.

In some embodiments, the bioreactor is a chemostat. A chemostat generally refers to a bioreactor that is continuously operated such that an input stream comprising a cell culture medium is continuously supplied and an output stream comprising at least a portion of the cell culture medium and the biological cells is continuously removed such that the wet cell weight of the biological cells is maintained at a substantially constant value. In some embodiments, the bioreactor is a continuous stirred tank reactor (CSTR).

In some embodiments, the bioreactor comprises a reaction chamber. In certain embodiments, the reaction chamber has an internal volume (i.e., a volume capable of containing a fluid such as a cell suspension) of at least about 50 mL, at least about 100 mL, at least about 200 mL, at least about 500 mL, at least about 1 L, at least about 2 L, at least about 5 L, at least about 10 L, at least about 50 L, at least about 100 L, at least about 150 L, or at least about 200 L. In some embodiments, the reaction chamber has an internal volume of about 200 L or less, about 150 L or less, about 100 L or less, about 50 L or less, about 10 L or less, about 5 L or less, about 2 L or less, about 1 L or less, about 500 mL or less, about 200 mL or less, about 100 mL or less, or about 50 mL or less. In some embodiments, the reaction chamber has an internal volume in the range of about 50 mL to about 100 mL, about 50 mL to about 500 mL, about 50 mL to about 1 L, about 50 mL to about 5 L, about 50 mL to about 10 L, about 50 mL to about 50 L, about 50 mL to about 100 L, about 50 mL to about 200 L, about 100 mL to about 500 mL, about 100 mL to about 1 L, about 100 mL to about 5 L, about 100 mL to about 10 L, about 100 mL to about 50 L, about 100 mL to about 100 L, about 100 mL to about 200 L, about 500 mL to about 1 L, about 500 mL to about 5 L, about 500 mL to about 10 L, about 500 mL to about 50 L, about 500 mL to about 100 L, about 500 mL to about 200 L, about 1 L to about 10 L, about 1 L to about 50 L, about 1 L to about 100 L, about 1 L to about 200 L, about 10 L to about 50 mL, about 10 L to about 100 L, about 10 L to about 200 L, about 50 L to about 100 L, about 50 L to about 200 L, or about 100 L to about 200 L.

The reaction chamber of the bioreactor may have any suitable shape. According to certain embodiments, for example, the reaction chamber may be substantially cylindrical. The reaction chamber also may be formed of any suitable material. Non-limiting examples of a suitable material include stainless steel, glass, and plastic. In some embodiments, the reaction chamber comprises one or more internal components, such as an agitator. An agitator may, for example, promote suspension of the cells within the cell culture medium. In some embodiments, the bioreactor is fluidically connected (e.g., directly fluidically connected) to a gas concentration device. In certain cases, the gas concentration device is an oxygen concentrator.

In some embodiments, the bioreactor is operated in at least two phases: a cell growth phase and a biologically-produced product production phase. According to certain embodiments, in the cell growth phase, the bioreactor receives a first type of biological cells configured to express at least one biologically-produced product (i.e., the bioreactor is "inoculated" with the first type of biological cells) and receives a feed stream comprising a growth cell culture medium configured to promote the growth of the first type of biological cells. In some embodiments, the first type of biological cells are incubated in the growth cell culture medium for a period of at least about 1 hour, at least about 6 hours, at least about 12 hours, at least about 24 hours, at least about 32 hours, at least about 36 hours, at least about 2 days, at least about 3 days, at least about 4 days, at least about 5 days, at least about 6 days, at least about 7 days. In some embodiments, the first type of biological cells are incubated in the growth cell culture medium for a period in the range of about 1 hour to about 12 hours, about 1 hour to about 24 hours, about 1 hour to about 32 hours, about 1 hour to about 36 hours, about 1 hour to about 48 hours, about 1 hour to about 72 hours, about 1 hour to about 4 days, about 1 hour to about 5 days, about 1 hour to about 6 days, about 1 hour to about 7 days, about 12 hours to about 24 hours, about 12 hours to about 36 hours, about 12 hours to about 48 hours, about 12 hours to about 72 hours, about 12 hours to about 4 days, about 12 hours to about 5 days, about 12 hours to about 6 days, about 12 hours to about 7 days, about 24 hours to about 36 hours, about 24 hours to about 48 hours, about 24 hours to about 72 hours, about 24 hours to about 4 days, about 24 hours to about 5 days, about 24 hours to about 6 days, about 24 hours to about 7 days, about 36 hours to about 72 hours, about 3 days to about 4 days, about 3 days to about 5 days, about 3 days to about 6 days, about 3 days to about 7 days, about 4 days to about 7 days, or about 5 days to about 7 days.

In some embodiments, the first type of biological cells are incubated in the growth cell culture medium until they reach a wet cell weight of at least about 150 g/L, at least about 200 g/L, at least about 250 g/L, at least about 300 g/L, at least about 350 g/L, at least about 400 g/L, at least about 450 g/L, at least about 500 g/L, at least about 550 g/L, at least about 600 g/L, at least about 650 g/L, or at least about 700 g/L. In some embodiments, the first type of biological cells are incubated in the growth cell culture medium until they reach a wet cell weight in the range of about 150 g/L to about 200 g/L, about 150 g/L to about 300 g/L, about 150 g/L to about 400 g/L, about 150 g/L to about 500 g/L, about 150 g/L to about 550 g/L, about 150 g/L to about 600 g/L, about 150 g/L to about 660 g/L, about 150 g/L to about 700 g/L, about 200 g/L to about 300 g/L, about 200 g/L to about 400 g/L, about 200 g/L to about 500 g/L, about 200 g/L to about 550 g/L, about 200 g/L to about 600 g/L, about 200 g/L to about 660 g/L, about 200 g/L to about 700 g/L, about 300 g/L to about 500 g/L, about 300 g/L to about 550 g/L, about 300 g/L to about 600 g/L, about 300 g/L to about 660 g/L, about 300 g/L to about 700 g/L, about 400 g/L to about 500 g/L, about 400 g/L to about 550 g/L, about 400 g/L to about 600 g/L, about 400 g/L to about 660 g/L, about 400 g/L to about 700 g/L, about 500 g/L to about 600 g/L, about 500 g/L to about 700 g/L, or about 600 g/L to about 700 g/L. The wet cell weight may be measured by a mass balance.

According to some embodiments, the cell growth phase is ended by removing the growth cell culture medium from the reaction chamber of the bioreactor. In some embodiments, the biologically-produced product production phase is initiated by introducing a production cell culture medium configured to promote expression of the at least one biologically-produced product into the reaction chamber.

According to some embodiments, in the biologically-produced product production phase, the bioreactor receives a feed stream comprising the production cell culture medium.

In some embodiments, the first type of biological cells suspended in the production cell culture medium produce at least one biologically-produced product for a period of at least about 1 day, at least about 2 days, at least about 3 days, at least about 4 days, at least about 5 days, at least about 6 days, at least about 7 days, at least about 2 weeks, at least about 4 weeks, at least about 6 weeks, or at least about 10 weeks. In some embodiments, the first type of biological cells suspended in the production cell culture medium produce at least one biologically-produced product for a period in the range of about 1 day to about 7 days, about 1 day to about 2 weeks, about 1 day to about 4 weeks, about 1 day to about 6 weeks, about 1 day to about 10 weeks, about 7 days to about 2 weeks, about 7 days to about 4 weeks, about 7 days to about 6 weeks, about 7 days to about 10 weeks, about 4 weeks to about 6 weeks, or about 4 weeks to about 10 weeks.

In some embodiments, the first type of biological cells suspended in the production cell culture medium have a wet cell weight of at least about 150 g/L, at least about 200 g/L, at least about 250 g/L, at least about 300 g/L, at least about 350 g/L, at least about 400 g/L, at least about 450 g/L, at least about 500 g/L, at least about 550 g/L, at least about 600 g/L, at least about 650 g/L, or at least about 700 g/L. In some embodiments, the first type of biological cells suspended in the production cell culture medium have a wet cell weight in the range of about 150 g/L to about 200 g/L, about 150 g/L to about 300 g/L, about 150 g/L to about 400 g/L, about 150 g/L to about 500 g/L, about 150 g/L to about 550 g/L, about 150 g/L to about 600 g/L, about 150 g/L to about 660 g/L, about 150 g/L to about 700 g/L, about 200 g/L to about 300 g/L, about 200 g/L to about 400 g/L, about 200 g/L to about 500 g/L, about 200 g/L to about 550 g/L, about 200 g/L to about 600 g/L, about 200 g/L to about 660 g/L, about 200 g/L to about 700 g/L, about 300 g/L to about 500 g/L, about 300 g/L to about 550 g/L, about 300 g/L to about 600 g/L, about 300 g/L to about 660 g/L, about 300 g/L to about 700 g/L, about 400 g/L to about 500 g/L, about 400 g/L to about 550 g/L, about 400 g/L to about 600 g/L, about 400 g/L to about 660 g/L, about 400 g/L to about 700 g/L, about 500 g/L to about 600 g/L, about 500 g/L to about 700 g/L, or about 600 g/L to about 700 g/L.

In some embodiments, at least a portion of the suspension (e.g., the first type of biological cells suspended in a cell culture medium) flows through the filter probe at a relatively high flow rate to produce a filtrate stream. In some embodiments, the flow rate is at least about 0.1 mL/min, at least about 0.5 mL/min, at least about 1 mL/min, at least about 2 mL/min, at least about 3 mL/min, at least about 4 mL/min, at least about 5 mL/min, at least about 6 mL/min, at least about 7 mL/min, at least about 8 mL/min, at least about 9 mL/min, at least about 10 mL/min, at least about 15 mL/min, at least about 20 mL/min, at least about 50 mL/min, at least about 100 mL/min, at least about 150 mL/min, at least about 200 mL/min, at least about 250 mL/min, or at least about 300 mL/min. In some embodiments, the flow rate is between about 0.1 mL/min and about 1 mL/min, between about 0.1 mL/min and about 5 mL/min, between about 0.1 mL/min and about 10 mL/min, between about 0.1 mL/min and about 15 mL/min, between about 0.1 mL/min and about 20 mL/min, between about 0.1 mL/min and about 50 mL/min, between about 0.1 mL/min and about 100 mL/min, between about 0.1 mL/min and about 150 mL/min, between about 0.1 mL/min and about 200 mL/min, between about 0.1 mL/min and about 250 mL/min, between about 0.1 mL/min and about 300 mL/min, between about 1 mL/min and about 5 mL/min, between about 1 mL/min and about 10 mL/min, between about 1 mL/min and about 15 mL/min, between about 1 mL/min and about 20 mL/min, between about 1 mL/min and about 50 mL/min, between about 1 mL/min and about 100 mL/min, between about 1 mL/min and about 150 mL/min, between about 1 mL/min and about 200 mL/min, between about 1 mL/min and about 250 mL/min, between about 1 mL/min and about 300 mL/min, between about 5 mL/min and about 10 mL/min, between about 5 mL/min and about 15 mL/min, between about 5 mL/min and about 20 mL/min, between about 5 mL/min and about 50 mL/min, between about 5 mL/min and about 100 mL/min, between about 5 mL/min and about 150 mL/min, between about 5 mL/min and about 200 mL/min, between about 5 mL/min and about 250 mL/min, between about 5 mL/min and about 300 mL/min, between about 10 mL/min and about 20 mL/min, between about 10 mL/min and about 50 mL/min, between about 10 mL/min and about 100 mL/min, between about 10 mL/min and about 150 mL/min, between about 10 mL/min and about 200 mL/min, between about 10 mL/min and about 250 mL/min, between about 10 mL/min and about 300 mL/min, between about 50 mL/min and about 100 mL/min, between about 50 mL/min and about 150 mL/min, between about 50 mL/min and about 200 mL/min, between about 50 mL/min and about 250 mL/min, between about 50 mL/min and about 300 mL/min, between about 100 mL/min and about 200 mL/min, or between about 100 mL/min and about 300 mL/min over a specified time period. The flow rate of any fluid stream within a system may be measured using any suitable flow rate measurement device known in the art. Non-limiting examples of suitable flow rate measurement devices include ultrasonic flow meters, paddle wheel flow meters, rotameters, vortex flow meters, magnetic flow meters, turbine flow meters, and optical flow sensors (e.g., microparticle or bubble detection devices).

In some embodiments, the specified time period is at least about 1 hour, at least about 2 hours, at least about 5 hours, at least about 10 hours, at least about 1 day, at least about 2 days, at least about 3 days, at least about 4 days, at least about 5 days, at least about 6 days, at least about 7 days, at least about 2 weeks, at least about 5 weeks, or at least about 10 weeks.

In some embodiments, at least a portion of a filtrate stream may be backflushed through the filter probe at a relatively high flow rate to de-foul the filter probe. In some embodiments, the flow rate is at least about 1 mL/min, at least about 2 mL/min, at least about 3 mL/min, at least about 4 mL/min, at least about 5 mL/min, at least about 6 mL/min, at least about 7 mL/min, at least about 8 mL/min, at least about 9 mL/min, at least about 10 mL/min, at least about 11 mL/min, at least about 12 mL/min, at least about 13 mL/min, at least about 14 mL/min, at least about 15 mL/min, at least about 20 mL/min, at least about 30 mL/min, at least about 40 mL/min, at least about 50 mL/min, at least about 100 mL/min, at least about 150 mL/min, at least about 200 mL/min, at least about 250 mL/min, at least about 300 mL/min, at least about 350 mL/min, at least about 400 mL/min, at least about 450 mL/min, at least about 500 mL/min, at least about 550 mL/min, or at least about 600 mL/min. In some embodiments, the flow rate is between about 1 mL/min and about 5 mL/min, between about 1 mL/min and about 10 mL/min, between about 1 mL/min and about 15 mL/min, between about 1 mL/min and about 20 mL/min, between 1 mL/min and about 30 mL/min, between about 1 mL/min and about 40 mL/min, between about 1 mL/min and about 50 mL/min, between about 1 mL/min and about 100 mL/min, between about 1 mL/min and about 200 mL/min, between about 1 mL/min and about 300 mL/min, between about 1 mL/min and about 400 mL/min, between about 1 mL/min and about 500 mL/min, between about 1 mL/min and about 600 mL/min, between about 5 mL/min and about 10 mL/min, between about 5 mL/min and about 15 mL/min, between about 5 mL/min and about 20 mL/min, between 5 mL/min and about 30 mL/min, between about 5 mL/min and about 40 mL/min, between about 5 mL/min and about 50 mL/min, between about 5 mL/min and about 100 mL/min, between about 5 mL/min and about 200 mL/min, between about 5 mL/min and about 300 mL/min, between about 5 mL/min and about 400 mL/min, between about 5 mL/min and about 500 mL/min, between about 5 mL/min and about 600 mL/min, between about 10 mL/min and about 20 mL/min, between 10 mL/min and about 30 mL/min, between about 10 mL/min and about 40 mL/min, between about 10 mL/min and about 50 mL/min, between about 10 mL/min and about 100 mL/min, between about 10 mL/min and about 200 mL/min, between about 10 mL/min and about 300 mL/min, between about 10 mL/min and about 400 mL/min, between about 10 mL/min and about 500 mL/min, between about 10 mL/min and about 600 mL/min, between 20 mL/min and about 30 mL/min, between about 20 mL/min and about 40 mL/min, between about 20 mL/min and about 50 mL/min, between about 20 mL/min and about 100 mL/min, between about 20 mL/min and about 200 mL/min, between about 20 mL/min and about 300 mL/min, between about 20 mL/min and about 400 mL/min, between about 20 mL/min and about 500 mL/min, between about 20 mL/min and about 600 mL/min, between about 50 mL/min and about 100 mL/min, between about 50 mL/min and about 200 mL/min, between about 50 mL/min and about 300 mL/min, between about 50 mL/min and about 400 mL/min, between about 50 mL/min and about 500 mL/min, between about 50 mL/min and about 600 mL/min, between about 100 mL/min and about 200 mL/min, between about 100 mL/min and about 300 mL/min, between about 100 mL/min and about 400 mL/min, between about 100 mL/min and about 500 mL/min, between about 100 mL/min and about 600 mL/min, between about 200 mL/min and about 600 mL/min, between about 300 mL/min and about 600 mL/min, between about 400 mL/min and about 600 mL/min, or between about 500 mL/min and about 600 mL/min over a specified time period.

In some embodiments, the specified time period is at least about 1 second, at least about 5 seconds, at least about 10 seconds, at least about 30 seconds, at least about 1 minute, at least about 2 minutes, at least about 3 minutes, at least about 4 minutes, at least about 5 minutes, at least about 6 minutes, at least about 7 minutes, at least about 8 minutes, at least about 9 minutes, or at least about 10 minutes. In some embodiments, the specified time period is between about 1 second and about 10 seconds, between about 1 second and about 30 seconds, between about 1 second and about 1 minute, between about 1 second and about 5 minutes, between about 1 second and about 10 minutes, between about 1 minute and about 5 minutes, between about 1 minute and about 10 minutes, or between about 5 minutes and about 10 minutes.

In some embodiments, a relatively large portion of the suspension (e.g., the first type of biological cells suspended in a cell culture medium) flows through the filter probe per day. In certain embodiments, the flow rate is at least about 0.5 reactor volumes per day (RV/day), at least about 1 RV/day, at least about 1.5 RV/day, at least about 2 RV/day, at least about 2.5 RV/day, at least about 3 RV/day, at least about 3.5 RV/day, at least about 4 RV/day, at least about 4.5 RV/day, or at least about 5 RV/day. In some embodiments, the flow rate is between about 0.5 RV/day and about 1 RV/day, between about 0.5 RV/day and about 1.5 RV/day, between about 0.5 RV/day and about 2 RV/day, between about 0.5 RV/day and about 2.5 RV/day, between about 0.5 RV/day and about 3 RV/day, between about 0.5 RV/day and about 3.5 RV/day, between about 0.5 RV/day and about 4 RV/day, between about 0.5 RV/day and about 4.5 RV/day, between about 0.5 RV/day and about 5 RV/day, between about 1 RV/day and about 1.5 RV/day, between about 1 RV/day and about 2 RV/day, between about 1 RV/day and about 2.5 RV/day, between about 1 RV/day and about 3 RV/day, between about 1 RV/day and about 3.5 RV/day, between about 1 RV/day and about 4 RV/day, between about 1 RV/day and about 4.5 RV/day, between about 1 RV/day and about 5 RV/day, between about 2 RV/day and about 2.5 RV/day, between about 2 RV/day and about 3 RV/day, between about 2 RV/day and about 3.5 RV/day, between about 2 RV/day and about 4 RV/day, between about 2 RV/day and about 4.5 RV/day, between about 2 RV/day and about 5 RV/day, between about 3 RV/day and about 3.5 RV/day, between about 3 RV/day and about 4 RV/day, between about 3 RV/day and about 4.5 RV/day, between about 3 RV/day and about 5 RV/day, between about 4 RV/day and about 4.5 RV/day, or between about 4 RV/day and about 5 RV/day. As used herein, a reactor volume refers to the volume of the reaction chamber of a bioreactor.

In some embodiments, a relatively large portion of the suspension (e.g., the first type of biological cells suspended in a cell culture medium) flows through a filter probe having a relatively small diameter per day. In certain embodiments, a filter probe having a diameter of about 25 mm or less, about 20 mm or less, about 15 mm or less, about 10 mm or less, or about 5 mm or less has a flow rate of at least about 0.5 RV/day, at least about 1 RV/day, at least about 1.5 RV/day, at least about 2 RV/day, at least about 2.5 RV/day, at least about 3 RV/day, at least about 3.5 RV/day, at least about 4 RV/day, at least about 4.5 RV/day, or at least about 5 RV/day. In some embodiments, a filter probe having a diameter of about 25 mm or less, about 20 mm or less, about 15 mm or less, about 10 mm or less, or about 5 mm or less has a flow rate between about 0.5 RV/day and about 1 RV/day, between about 0.5 RV/day and about 1.5 RV/day, between about 0.5 RV/day and about 2 RV/day, between about 0.5 RV/day and about 2.5 RV/day, between about 0.5 RV/day and about 3 RV/day, between about 0.5 RV/day and about 3.5 RV/day, between about 0.5 RV/day and about 4 RV/day, between about 0.5 RV/day and about 4.5 RV/day, between about 0.5 RV/day and about 5 RV/day, between about 1 RV/day and about 1.5 RV/day, between about 1 RV/day and about 2 RV/day, between about 1 RV/day and about 2.5 RV/day, between about 1 RV/day and about 3 RV/day, between about 1 RV/day and about 3.5 RV/day, between about 1 RV/day and about 4 RV/day, between about 1 RV/day and about 4.5 RV/day, between about 1 RV/day and about 5 RV/day, between about 2 RV/day and about 2.5 RV/day, between about 2 RV/day and about 3 RV/day, between about 2 RV/day and about 3.5 RV/day, between about 2 RV/day and about 4 RV/day, between about 2 RV/day and about 4.5 RV/day, between about 2 RV/day and about 5 RV/day, between about 3 RV/day and about 3.5 RV/day, between about 3 RV/day and about 4 RV/day, between about 3 RV/day and about 4.5 RV/day, between about 3 RV/day and about 5 RV/day, between about 4 RV/day and about 4.5 RV/day, or between about 4 RV/day and about 5 RV/day.

In some embodiments, the filtrate stream is lean in the first type of biological cells relative to the cell suspension contained in the bioreactor. In certain embodiments, for example, the wet cell weight of the first type of biological cells in the filtrate stream is about 1 µg/L or less, about 0.5 µg/L or less, about 0.1 µg/L or less, about 0.05 µg/L or less, or about 0.01 µg/L or less. In some embodiments, the ratio of wet cell weight of the first type of biological cells in the growth medium in the bioreactor to the wet cell weight of the first type of biological cells in the filtrate stream is at least about $1 \times 10^6$, at least about $1 \times 10^7$, at least about $1 \times 10^8$, or at least about $1 \times 10^9$.

In some embodiments, the first type of biological cells is configured to express at least one biologically-produced product. For example, the first type of biological cells may be genetically engineered to express at least one biologically-produced product (e.g., via site-directed mutagenesis, gene insertion, viral vectors, microinjection, plasmids, recombinant DNA, metal nanoparticles, electroporation, chemical poration). In some embodiments, the biologically-produced product is a protein product and/or a pharmaceutical product. Non-limiting examples of a suitable biologically-produced product include a cytokine, an antibody, an antibody fragment, a nanobody, a hormone, an enzyme, a growth factor, a blood factor, a recombinant immunogen, and a fusion protein. In some embodiments, the antibody is a single-chain antibody, a bispecific antibody, and/or a monoclonal antibody. In some embodiments, the cytokine is an interferon. According to certain embodiments, the at least one biologically-produced product comprises human growth hormone (hGH), granulocyte-colony stimulating factor (G-CSF), and/or interferon-α2b (IFN-α2b).

The first type of biological cells may be any suitable type of cells. In some embodiments, the first type of biological cells is a prokaryotic cell. Non-limiting examples of suitable prokaryotic cells include cyanobacteria algae and bacteria. The bacterium may be a gram-negative bacterium, including, but not limited to, including *Escherichia*, *Salmonella*, *Shigella*, *Pseudomonas*, *Neisseria*, *Chlamydia*, *Yersinia*, *Moraxella*, *Haemophilus*, *Helicobacter*, *Acinetobacter*, *Stenotrophomonas*, *Bdellovibrio*, *Legionella*, and acetic acid bacteria. In other embodiments, the bacterium may be a gram-positive bacterium, including, but not limited to, *Streptococcus*, *Staphylococcus*, *Corynebacterium*, *Listeria*, *Bacillus*, *Clostridium*, *Lactobacillus*, and *Mycobacterium*.

In some embodiments, the first type of biological cells is a lower eukaryotic cell. Lower eukaryotes include yeast, fungi, collar-*flagellates*, microsporidia, alveolates (e.g., dinoflagellates), stramenopiles (e.g., brown algae, protozoa), rhodophyta (e.g., red algae), plants (e.g., green algae, plant cells, moss) and other protists. In some embodiments, the first type of biological cells are microalgae cells. A non-limiting example of microalgae cells is *Chlamydomonas reinhardtii* cells. In some embodiments, the first type of biological cells are diatom cells. A non-limiting example of diatom cells is *Phaeodactylum tricornutum* cells. In some embodiments, the first type of biological cells are plant cells (e.g., carrot cells).

In some embodiments, the first type of biological cells is a yeast cell. Examples of yeast cells include, but are not limited to, *Arxula adeninivorans*, *Aureobasidium pullulans*, *Aureobasidium melanogenum*, *Aureobasidium namibiae*, *Aureobasidium subglaciale*, *Brettanomyces bruxellensis*, *Brettanomyces claussenii*, *Candida albicans*, *Candida auris*, *Candida bracarensis*, *Candida bromeliacearum*, *Candida dubliniensis*, *Candida glabrata*, *Candida humilis*, *Candida keroseneae*, *Candida krusei*, *Candida lusitaniae*, *Candida oleophila*, *Candida parapsilosis*, *Candida rhizophoriensis*, *Candida sharkiensis*, *Candida stellate*, *Candida theae*, *Candida tolerans*, *Candida tropicalis*, *Candida ubatubensis*, *Candida viswanathii*, *Candida zemplinina*, *Cryptococcus gattii*, *Cryptococcus neoformans*, *Debaryomyces hansenii*, *Hansenula polymorpha*, *Hanseniaspora guilliermondii*, *Kluyveromyces lactis* and like kinds, *Kluyveromyces marxianus*, *Leucosporidium frigidum*, *Macrorhabdus ornithogaster*, *Malassezia caprae*, *Malassezia dermatis*, *Malassezia equine*, *Malassezia japonica*, *Malassezia nana*, *Malassezia sympodialis*, *Ogataea methanolica*, *Ogataea polymorpha*, *Pachysolen tannophilus*, *Pichia anomala*, *Pichia guilliermondii*, *Pichia pastoris*, *Pichia stipites*, *Pichia finlandica*, *Pichia trehalophila*, *Pichia koclamae*, *Pichia membranaefaciens*, *Pichia minuta* (*Ogataea minuta*, *Pichia lindneri*), *Pichia opuntiae*, *Pichia thermotolerans*, *Pichia salictaria*, *Pichia guercuum*, *Pichia pijperi*, *Pichia stiptis*, *Pichia methanolica*, *Rhodotorula cladiensis*, *Rhodotorula evergladiensis*, *Saccharomyces bayanus*, *Saccharomyces boulardii*, *Saccharomyces cerevisiae*, *Saccharomyces paradoxus*, *Schizosaccharomyces pombe*, *Yarrowia lipolytica*, and *Zygosaccharomyces bailii*. In one embodiment, the yeast is *Pichia pastoris*.

In some embodiments, the first type of biological cells is a filamentous fungi. Non-limiting examples of filamentous fungi include *Trichoderma*, for example from *Trichoderma reesei*; *Neurospora*, for example from *Neurospora crassa*; *Sordaria*, for example from *Sordaria macrospora*; *Aspergillus*, for example from *Aspergillus niger*, *Aspergillus nidulans*, *Aspergillus oryzae*, or from *Aspergillus sojae*; *Fonsecaea*, for example from *Fonsecaea pedrosoi*; *Cladosporium*, for example from *Cladosporium carrionii*; *Chrysosporium luchiowense*; *Fusarium* sp. (for example, *Fusarium gramineum*, *Fusarium venenatum*); *Physcomitrella patens*; or *Phialophora*, for example from *Phialophora verrucosa*.

The smaller secretome of organisms such as *Pichia pastoris* and similar cells are surprisingly advantageous in the context of designing and operating the integrated systems of certain embodiments. For example, *Pichia pastoris*, which is a methylotrophic yeast, contains the necessary cellular machinery for protein folding, glycosylation, and secretion, so it can be used to produce complex heterologous proteins used as therapeutics. However, its smaller secretome allows for more streamlined downstream (e.g., purification) processes than higher eukaryotic cells.

In some embodiments, the first type of biological cells is a higher eukaryotic cell. Higher eukaryotic cells include mammalian cells. Non-limiting examples of suitable mammalian cells include bovine cells, porcine cells, ovine cells, human cells, mouse cells, Chinese hamster ovary (CHO) cells, canine cells, feline cells, and hybridomas. In some embodiments, the higher eukaryotic cells are insect cells.

In some embodiments, the reaction chamber contains a growth cell culture medium configured to promote growth of the first type of biological cells. Non-limiting examples of a suitable growth cell culture medium include buffered glycerol-complex medium (BMGY), basal salt media, FM22, and d'Anjou media. Other examples of suitable cell culture media are described in PCT Application No. PCT/US2018/025406, entitled "Media for Microorganism Culture and Related Compositions and Methods," and filed on Mar. 30, 2018, U.S. Provisional Patent Application Ser. No. 62/644,820, entitled "Media for Microorganism Culture and Related Compositions and Methods," and filed on Mar. 19, 2018, and U.S. Provisional Patent Application Ser. No. 62/480,416, entitled "Media for Microorganism Culture and Related Compositions and Methods," and filed on Apr. 1, 2017, the contents of all of which are incorporated herein by reference in their entireties for all purposes. In some embodiments, the pH of the growth cell culture medium is at least about 4.0, at least about 5.0, at least about 5.5, at least about 6.0, at least about 6.5, at least about 7.0, at least about 7.5, at least about 8.0, or at least about 8.5. In some embodiments, the pH of the growth cell culture medium is about 8.5 or less, about 8.0 or less, about 7.5 or less, about 7.0 or less, about 6.5 or less, about 6.0 or less, about 5.5 or less, about 5.0 or less, or about 4.0 or less. In some embodiments, the pH of the growth cell culture medium is in the range of about 4.0 to about 6.0, about 4.0 to about 7.0, about 4.0 to about 8.0, about 4.0 to about 8.5, about 5.0 to about 7.0, about 5.0 to about 8.0, about 5.0 to about 8.5, about 6.0 to about 7.0, about 6.0 to about 8.0, about 6.0 to about 8.5, about 7.0 to about 8.0, or about 7.0 to about 8.5. The pH of the growth cell culture medium may be measured according to any method known in the art. For example, the pH may be measured using a digital pH meter.

In some embodiments, the reaction chamber contains a production cell culture medium configured to promote expression of at least one biologically-produced product by the first type of biological cells. Non-limiting examples of a suitable production cell culture medium include buffered methanol-complex medium (BMMY), basal salt media with methanol, FM22 with methanol, and d'Anjou media with methanol. In some embodiments, the pH of the production cell culture medium is at least about 4.0, at least about 5.0, at least about 5.5, at least about 6.0, at least about 6.5, at least about 7.0, at least about 7.5, at least about 8.0, or at least about 8.5. In some embodiments, the pH of the production cell culture medium is about 8.5 or less, about 8.0 or less, about 7.5 or less, about 7.0 or less, about 6.5 or less, about 6.0 or less, about 5.5 or less, about 5.0 or less, or about 4.0 or less. In some embodiments, the pH of the production cell culture medium is in the range of about 4.0 to about 6.0, about 4.0 to about 7.0, about 4.0 to about 8.0, about 4.0 to about 8.5, about 5.0 to about 7.0, about 5.0 to about 8.0, about 5.0 to about 8.5, about 6.0 to about 7.0, about 6.0 to about 8.0, about 6.0 to about 8.5, about 7.0 to about 8.0, or about 7.0 to about 8.5.

Figure 8:
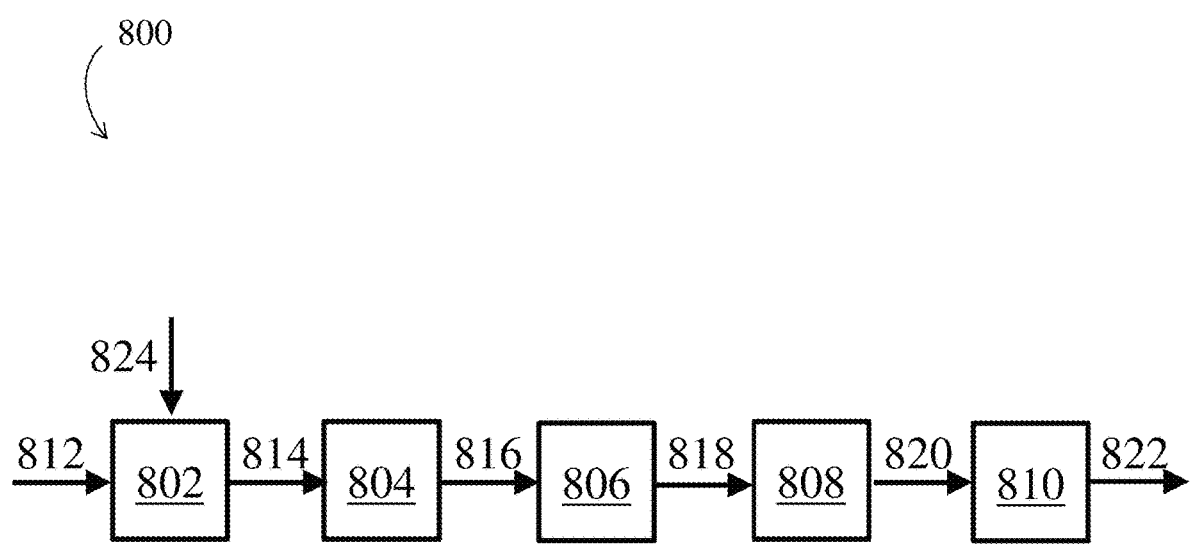
FIG. 8 is, according to some embodiments, a schematic diagram of an exemplary system comprising a bioreactor, a filter probe, an adjustment module, a purification module, and a formulation module.

In some embodiments, the system further comprises additional components in addition to a bioreactor and a filter probe. For example, FIG. 8 is a schematic diagram of exemplary system 800 comprising bioreactor 802, filter probe 804, adjustment module 806, purification module 808, and formulation module 810. According to some embodiments, adjustment module 806 is fluidically connected (e.g., directly fluidically connected) to filter probe 804 and/or bioreactor 802. Adjustment module 806 may be configured to adjust (e.g., increase, decrease) one or more properties (e.g., pH, conductivity, stability) of an outflow of filter probe 804 and/or bioreactor 802. In some embodiments, purification module 808 is fluidically connected (e.g., directly fluidically connected) to bioreactor 802, filter probe 804, and/or adjustment module 806. Purification module 808 may, in some embodiments, be configured to remove at least one type of impurity from an output of adjustment module 806, filter probe 804, and/or bioreactor 802. In certain cases, purification module 808 comprises one or more partitioning units configured to remove the at least one type of impurity. In some embodiments, formulation module 810 is fluidically connected (e.g., directly fluidically connected) to purification module 808, adjustment module 806, filter probe 804, and/or bioreactor 802. In some instances, formulation module 810 is configured to further process an output of bioreactor 802, filter probe 804, adjustment module 806, and/or purification module 808 to produce a formulated product. In some cases, formulation module 810 comprises a filtration unit (e.g., a tangential flow filtration device), a viral removal/inactivation unit, a product packaging unit, and/or a dilution adjustment unit.

In operation, bioreactor 802 receives a first type of biological cells 812 configured to express at least one biologically-produced product, according to some embodiments. In some embodiments, bioreactor 802 further receives feed stream 824 comprising a cell culture medium. The cell culture medium may, for example, be a growth cell culture medium configured to promote growth of the first type of biological cells and/or a production cell culture medium configured to promote expression of the at least one biologically-produced product. In some embodiments, the first type of biological cells are suspended in the cell culture medium, such that the reaction chamber of bioreactor 802 contains a suspension comprising the first type of biological cells and the cell culture medium. According to some embodiments, the first type of biological cells in the suspension proliferate and/or express the at least one biologically-produced product. In certain embodiments, the first type of biological cells secrete the at least one biologically-produced product into the cell culture medium of the suspension.

In some embodiments, at least a portion of the suspension is directed to flow through filter probe 804 as cell suspension stream 814 to produce first filtrate 816. According to some embodiments, first filtrate 816 comprises the at least one biologically-produced product and is lean in the first type of biological cells relative to cell suspension stream 814.

In some embodiments, first filtrate 816 is directed to flow to adjustment module 806, which may adjust (e.g., increase, decrease) one or more properties (e.g., pH, conductivity, stability) of first filtrate 816 to produce adjusted filtrate 818. In some embodiments, adjusted filtrate 818 is directed to flow to purification module 808 to produce purified filtrate 820. According to certain embodiments, one or more properties of adjusted filtrate 818 may be compatible with a partitioning technique and associated conditions applied by purification module 808. In some embodiments, purified filtrate 820 is directed to flow to formulation module 810 to produce formulated product stream 822.

In some embodiments, biomanufacturing system 800 (as illustrated in FIG. 8) is an integrated system. An integrated system generally refers to a system in which each system component is directly fluidically connected to at least one other system component such that a fluidic path (e.g., a closed fluidic path) exists from a first component to a last component of the system. According to some embodiments, for example, each component of biomanufacturing system 800 is directly fluidically connected to at least one other component of biomanufacturing system 800. In certain embodiments, bioreactor 802 is directly fluidically connected to filter probe 804, and filter probe 804 is directly fluidically connected to adjustment module 806. In certain other embodiments, bioreactor 802 is directly fluidically connected to filter probe 804, filter probe 804 is directly fluidically connected to adjustment module 806, adjustment module 806 is directly fluidically connected to purification module 808, and purification module 808 is directly connected to formulation module 810. In some embodiments, system 800 comprises a fluidic path from a first module (e.g., bioreactor 802) to an end module of system 800 (e.g., purification module 808, formulation module 810).

As used herein, a direct fluid connection exists between a first component and a second component (and the two components are said to be "directly fluidically connected" to each other) when they are fluidically connected to each other such that the composition of a connecting fluid stream does not substantially change (i.e., no phase change occurs and no fluid component changes in relative abundance by more than 5%) as it flows from the first component to the second component. As an illustrative example, a first component and a second component are "directly fluidically connected" if a connecting fluid stream undergoes changes in pressure and/or temperature during passage from the first component to the second component, but not if the connecting fluid stream undergoes a separation step or a chemical reaction that substantially alters the chemical composition of the connecting fluid stream during passage from the first component to the second component. In some embodiments, one or more fluidic connections (e.g., direct fluidic connections) between one or more modules are "functionally closed" (e.g., assembled so as to maintain aseptic conditions within the one or more modules).

In some embodiments, system 800 (as illustrated in FIG. 8) is a perfusion system. In certain embodiments, system 800 may be operated under substantially continuous and/or semi-continuous conditions. A system is generally considered to be operated under substantially continuous conditions if at least an input stream and an output stream of the system have a non-zero flow rate over a specified period of time. According to some embodiments, at least one component of system 800 (e.g., bioreactor 802, filter probe 804, adjustment module 806, purification module 808, formulation module 810) is operated under substantially continuous and/or semi-continuous conditions. In some embodiments, each component of system 800 is operated under substantially continuous and/or semi-continuous conditions. In certain embodiments, system 800 as a whole is operated under substantially continuous and/or semi-continuous conditions. According to some embodiments, each component of system 800 is directly fluidically connected to at least one other component such that a fluid stream flows from one component to the other. For example, in some embodiments, first filtrate 816 is a first filtrate stream. In some embodiments, adjusted filtrate 818 is an adjusted filtrate stream. In some embodiments, purified filtrate 820 is a purified filtrate stream.

Example 1

This Example describes an exemplary filter probe comprising 54 hollow fibers. Each of the 54 hollow fibers has an outer diameter of 0.8 mm and an inner diameter of 0.5 mm. The filter probe comprises a structured segment having a length of 250 mm and a diameter of 17.5 mm. Within the structured segment, each hollow fiber is spaced such that the center-to-center distance between hollow fibers is at least 2 mm (2.5 times the outer diameter of 0.8 mm). The exposed surface area of hollow fibers within the structured segment is 340 cm$^2$, which permits a flow rate of 7 mL/min through the filter probe in a broth of *Pichia pastoris* and a backflow rate of 14 mL/min to de-foul the probe. The hollow fibers have an average pore size of 0.2 μm.

In addition to the 54 hollow fibers, the filter probe comprises three spacing elements encircling and fixed to a central shaft. Each spacing element has an outer diameter of 17.5 mm and comprises clearance holes for the central shaft and each of the 54 hollow fibers. Each hollow fiber is spaced at least 2 mm away from the next closest hollow fiber and the central shaft.

The filter probe also comprises a hub and a collar (which collectively form an end piece). After being threaded through the three spacing elements, the hollow fibers are necked down through the hub. Necking eliminates the need for double-walled features, which permits increased hollow fiber count without increasing the outer diameter of the filter probe. The hub, which has a maximum outer diameter of 17.5 mm, has sufficient open area for the 54 hollow fibers to pass through with a 75% packing density. The hub is welded or epoxied to a mounting collar, and the hub distributes forces from fluid applied to the hollow fibers and central shaft to the mounting collar. At the top of the collar, the hollow fibers are potted and cleaved, and the collar can be threaded and attached to a separate shaft to be placed at a desired depth within bioreactor fluid.

The filter probe is capable of withstanding relatively high pressures and levels of radiation. In particular, the filter probe is able to withstand a negative (e.g., vacuum) pressure of 1 bar and a positive pressure of 3 bar. In addition, the filter probe is USP class VI and is able to withstand 50 kGy of gamma radiation. The materials of the filter probe (including the materials of the hollow fibers) are also chemically stable to methanol and glycerol.

Example 2

This Example describes a scaled down version of the filter probe described in Example 1. The filter probe of this Example is capable of being used in an Infors Bioreactor with a standard PG 13.5 port and a 12 mm through hole.

The filter probe comprises 18 hollow fibers. Each of the 18 hollow fibers has an outer diameter of 0.9 mm and an inner diameter of 0.5 mm. The filter probe comprises a structured segment having a length of 56 mm. Within the structured segment, each hollow fiber is spaced such that the center-to-center distance between hollow fibers is at least 2.25 mm (2.5 times the outer diameter of 0.9 mm). The exposed surface area of hollow fibers within the structured segment is 28.4 cm$^2$, which permits a flow rate of 4 mL/min through the filter probe in a broth of *Pichia pastoris* and a backflow rate of 8 mL/min to defoul the probe. The hollow fibers have an average pore size of 0.2 μm.

In addition to the 18 hollow fibers, the filter probe comprises two spacing elements encircling and fixed to a central shaft. Each spacing element comprises clearance holes for the central shaft and each of the 18 hollow fibers, where each hollow fiber clearance hole has a diameter of 1.16 mm (0.26 mm more than the outer diameter of 0.9 mm). Each hollow fiber is spaced at least 2.25 mm away from the next closest hollow fiber and the central shaft.

The filter probe also comprises a hub and a collar. After being threaded through the two spacing elements, the hollow fibers are necked down through the hub and fully potted in epoxy. The exposed hollow fibers (e.g., in the structured segment) are centered in the bioreactor fluid height. The expected wet cell weight is about 400 g/L, and the expected cell viscosity is about 5 cP.

The filter probe is capable of withstanding relatively high pressures and levels of radiation. In particular, the filter probe is able to withstand a negative (e.g., vacuum) pressure of 1 bar and a positive pressure of 3 bar. In addition, the filter probe is USP class VI and is able to withstand 50 kGy of gamma radiation. The materials of the filter probe (including the materials of the hollow fibers) are also chemically stable to methanol and glycerol.

Example 3

This Example describes a hollow fiber filter probe. The filter probe was designed within the envelope of a standard 12 mm PG13.5 port and thus was compatible with off-the-shelf stirred-tank bioreactors. Performance of the probe was demonstrated in a system in which a high-density *Pichia pastoris* culture was used to semi-continuously produce G-CSF.

Internal Hollow Fiber Probe Design

A hollow fiber probe for use within a stirred-tank bioreactor was designed. The bioreactor's agitation and sparging were used to maintain external cross flow, while the permeate flow was achieved by the application of vacuum within the lumen of the hollow fibers. The fibers were sealed and potted at the far end of the probe, while the fibers were potted and left open at the other end and connected to the 12 mm PG13.5 port. The small footprint of the port necessitated a tradeoff between filtration area and the spacing between fibers necessary to achieve the required cross flow velocity to maintain filtration flux.

Computational Fluid Dynamics Analysis

Computational fluid dynamics (CFD) was used to determine the optimal spacing of the fibers. A two-dimensional cross-section of the fiber design was simulated with the surrounding flow velocity equivalent to the rotational speed of the fluid within the bioreactor.

Under the flow conditions, a stagnation point occurred upstream, at the boundary, or inside of the fiber bundle. Based on simulations of multiple fiber diameters and center-to-center distances, it was determined that the center-to-center spacing of fibers should be 2.5 times the fiber diameter in order to avoid stagnation within the fiber bundle and a loss of net cross flow across the fibers.

The shear at the fiber surface was also compared to a reference ceramic filter design and to various designs for supporting the fibers against deflection from shear and for maximization of velocity. The center support was selected for construction, for having the highest average shear at the fiber surfaces and the highest internal flow velocities.

Figure 9A:
FIG. 9A is a schematic illustration of an exemplary filter probe comprising a barbed fitting, a PG13.5 thread, a riser, a hollow fiber section, and a lower cap, according to some embodiments.
Figure 9B:
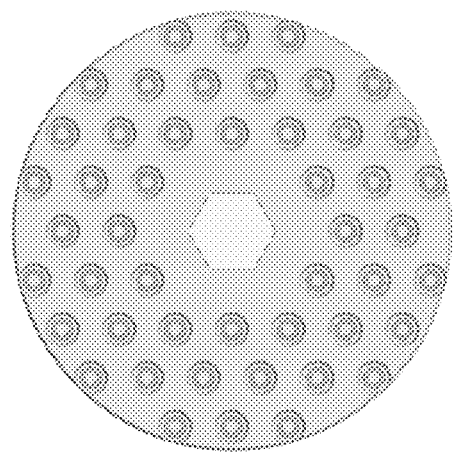
FIG. 9B is a schematic illustration showing the spacing and arrangement of hollow fibers around a hexagonal center support in an exemplary filter probe, according to some embodiments.
Figure 9C:
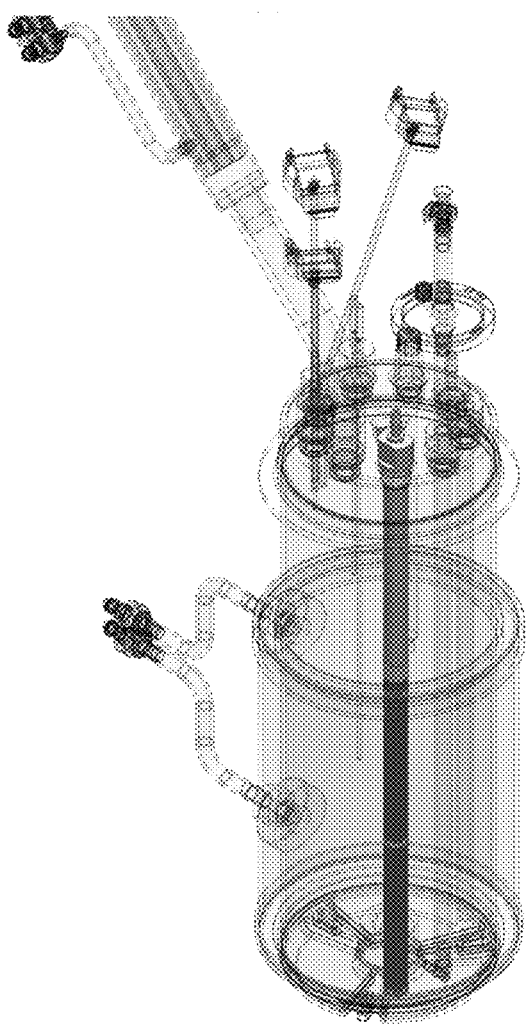
FIG. 9C is a schematic illustration of an exemplary system comprising a bioreactor and an installed filter probe, where the fibers of the filter probe span the height of the liquid within the bioreactor, according to some embodiments.

The fiber assembly was constructed to meet the mechanical strength requirements determined by CFD. A spacer was placed at the midpoint of the exposed fibers, to keep the semi-flexible fibers in the same relative position to each other (FIG. 9A). The fibers were arranged around a hexagonal center support (FIG. 9B), which was positioned off-center within the bioreactor (FIG. 9C).

Hollow Fiber Bioreactor Runs

Figure 10A:
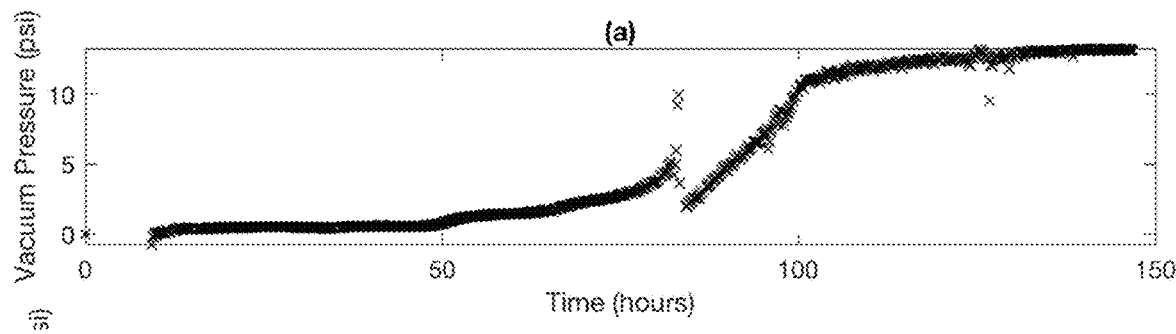
FIG. 10A is, according to some embodiments, an exemplary plot of vacuum pressure during suction across a filter probe (psi) as a function of time (hours) during a *Pichia pastoris* G-CSF bioreactor run.
Figure 10B:
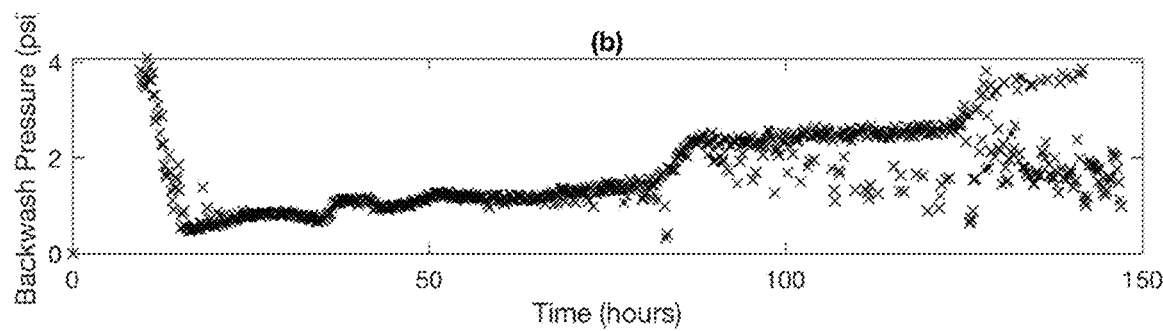
FIG. 10B is, according to some embodiments, an exemplary plot of backwash pressure during pressurization of the clean section of a filter probe (psi) as a function of time (hours) during a *Pichia pastoris* G-CSF bioreactor run.
Figure 10C:
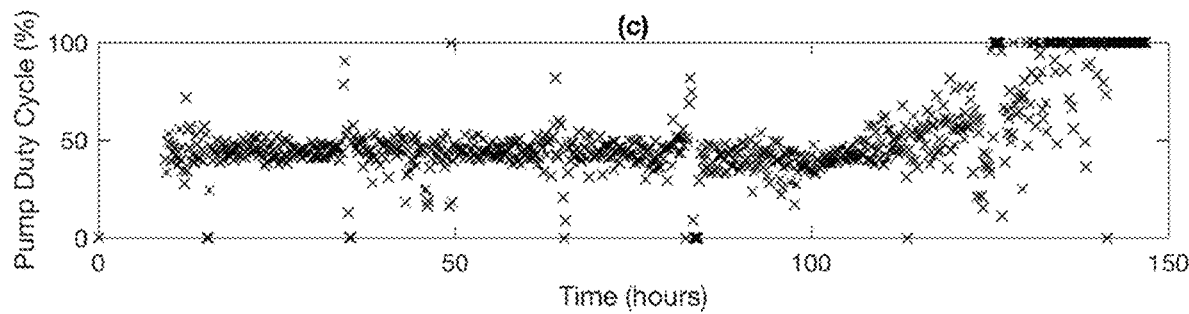
FIG. 10C is, according to some embodiments, an exemplary plot of pump duty cycle (fraction of time the outlet pump is running) (%) as a function of time (hours) during a *Pichia pastoris* G-CSF bioreactor run.

In order to validate the performance of the probe, *Pichia pastoris* was grown in a single-use 5 L bioreactor with the filter probe installed in one of the 12 mm PG13.5 ports. Effluent collected through the port was directed to an in-line pH adjustment and downstream purification module. As shown in FIG. 10A, initially the vacuum pressure was low since limited force was required to remove material fouled on the surface of the fibers, but the vacuum pressure slowly rose over time as an increasing amount of material remained attached to the fiber surfaces after each flushing. The filter probe remained operable for more than 100 hours, as seen by the cycle-averaged vacuum pressure being less than one atmosphere up that time. Although most material was removed during the flush step of each cycle, after an initial transient, the cycle-averaged backwash pressure slowly increased as material slowly built up on the fiber surface (FIG. 10B). The cycle-averaged pump duty cycle was below 100% for up to 130 hours (FIG. 10C), showing that the pump was operating normally up to that point. After 130 hours, fouling caused the vacuum pressure required to maintain reactor level to exceed the capabilities of the pump, resulting in a 100% duty cycle.

Example 4

Figure 11A:
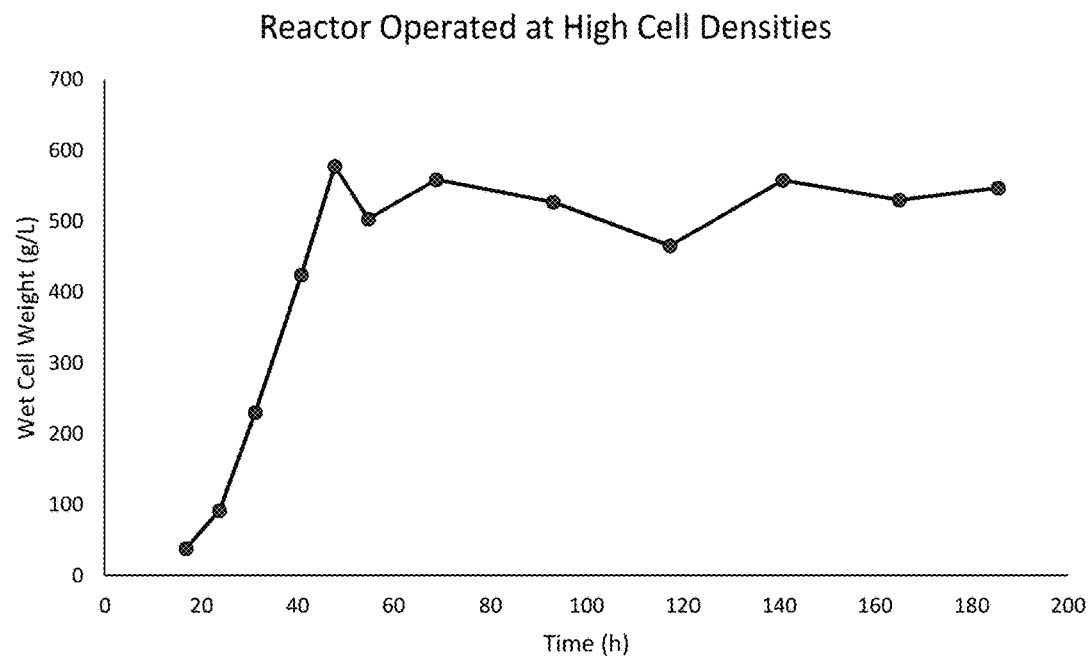
FIG. 11A is an exemplary plot of wet cell weights achieved over time during substantially continuous operation of a bioreactor with *Pichia pastoris*, according to some embodiments.
Figure 11B:
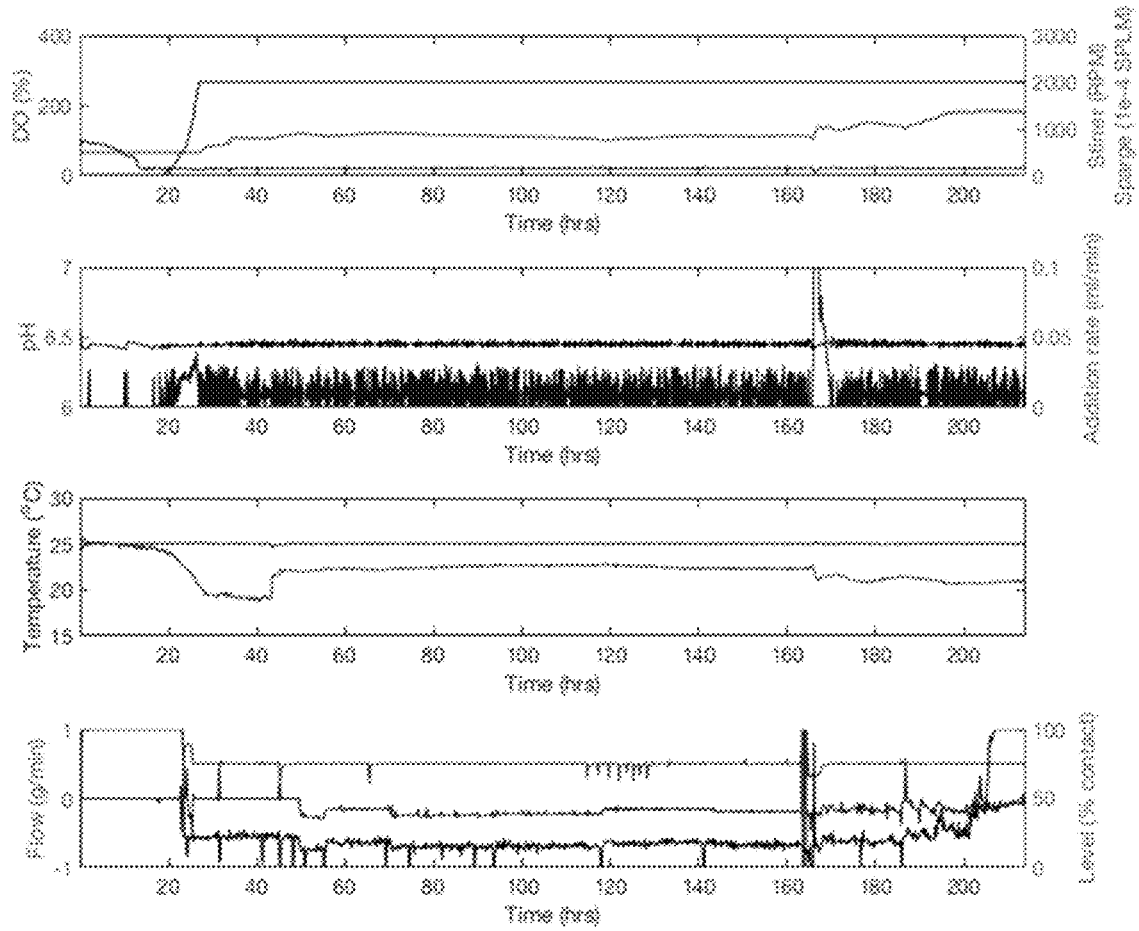
FIG. 11B is an exemplary plot of the fermentogram achieved over time during substantially continuous operation of a bioreactor with *Pichia pastoris*, according to some embodiments.

This Example describes validation of a two-part filter probe comprising an upper portion and a lower portion (e.g., having the structure shown in FIG. 7A). In this Example, *Pichia pastoris* was grown in a glass 0.75 L bioreactor with the filter probe installed in one of the 12 mm PG13.5 ports. Effluent was collected from the reactors over time. As shown in FIG. 11A, wet cell weights of more than 500 g/L were reached in 40 hours of inoculation. The fermentation was conducted for more than 180 hours. As shown in FIG. 11B, the fermentation transitioned from accumulation of biomass or outgrowth for 24 hours to perfusion for 188 h. Ammonium sulfate was added at 165 hours to test for nitrogen deficiency. Flow rates through the system were consistent to that point.

Example 5

This Example describes a hollow fiber probe configured to rotate. The probe design was evaluated using CFD to understand the impact of probe rotation. A 2-dimensional representation of the reactor was created with the hollow fiber probe, two small and two large probes, four baffles, and a six-bladed impeller. The flow field was evaluated using the multiple reference frame approach, where the hollow fiber probe and the impeller blades were evaluated in independent moving reference frames, while the rest of the fluid flow field was evaluated in a single stationary reference frame. Rotating the probe resulted in a visibly higher overall velocity within the probe, allowing for more rapid clearing of previous adherent solid materials removed within a backwash cycle. CFD simulations were conducted for rotation rates of the impeller of 20-80 radians/sec and the probe (clockwise 80 rad/sec to counterclockwise 80 rad/sec). Increasing both the impeller speed and probe speed resulted in an increase in shear rate. Operating the probe in a counterclockwise direction resulted in higher shear rates compared to the clockwise direction.

Example 6

This Example analyzes the impact of utilizing an external filter configuration with a high-density *Pichia pastoris* culture as opposed to a filter positioned internally within a bioreactor as in the previous examples.

The Henry's constant for water is 0.0013 mol/kg-bar, which means that a solution in equilibrium with air has a dissolved oxygen content of 34.8 mg/L of oxygen. *Pichia pastoris* cultures typically operate at about 25% of saturation with air, which corresponds to a dissolved oxygen content of 8.5 mg/L. When cultured on methanol-containing media, *Pichia pastoris* has an approximate oxygen-methanol yield of 1 $gO_2$/gMeOH. At a specific methanol uptake rate of 0.05 g MeOH/gWCW-h and a 500 gWCW/L culture density, the oxygen uptake rate is 6.9 mg/L-s. Under these conditions, oxygen in the culture can be completely consumed in 1.3 seconds.

Based on these results, a typical 10 second cycle time will likely result in hypoxic conditions within the external device. In addition, fluidic dead zones may result in a subset of cells having an extended residence time, exacerbating the problem. Such hypoxic conditions may lead to a loss of culture viability and lysis, causing the release of proteases that contribute to product degradation. Scaling up of the bioreactor volume results in a matched increase in filter area and cartridge volume, leading to longer residence times, compounding the problem further.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention. Having thus described several aspects of at least one embodiment, it is to be appreciated that various alterations, modifications, and improvements will readily occur to those skilled in the art. Such alterations, modifications, and improvements are intended to be within the spirit and scope of the present disclosure. Accordingly, the foregoing description and drawings are by way of example only.

The above-described embodiments of the present disclosure can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the concepts disclosed herein may be embodied as a non-transitory computer-readable medium (or multiple computer-readable media) (e.g., a computer memory, one or more floppy discs, compact discs, optical discs, magnetic tapes, flash memories, circuit configurations in Field Programmable Gate Arrays or other semiconductor devices, or other non-transitory, tangible computer storage medium) encoded with one or more programs that, when executed on one or more computers or other processors, perform methods that implement the various embodiments of the present disclosure discussed above. The computer-readable medium or media can be transportable, such that the program or programs stored thereon can be loaded onto one or more different computers or other processors to implement various aspects of the present disclosure as discussed above.

The terms "program" or "software" are used herein to refer to any type of computer code or set of computer-executable instructions that can be employed to program a computer or other processor to implement various aspects of the present disclosure as discussed above. Additionally, it should be appreciated that according to one aspect of this embodiment, one or more computer programs that when executed perform methods of the present disclosure need not reside on a single computer or processor, but may be distributed in a modular fashion amongst a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various features and aspects of the present disclosure may be used alone, in any combination of two or more, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the concepts disclosed herein may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc. in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall be interpreted as having the same meaning as "and/or" as defined above and shall not be interpreted as indicating exclusive alternatives (i.e. "one or the other but not both") unless preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A filter probe, comprising:
a fiber bundle comprising a plurality of hollow fibers,
wherein a center-to-center distance between any two hollow fibers within the fiber bundle at one or more points along a length of the fiber bundle is greater than or equal to 1.1 times a minimum diameter of the two hollow fibers,
wherein the filter probe has a diameter of about 25 mm or less and comprises 2500 or fewer fibers, and
wherein the filter probe is configured to be at least partially submerged in a liquid medium that is being filtered by the filter probe during operation.

2. The filter probe of claim 1, wherein the hollow fibers of the fiber bundle have an average outer diameter in a range between about 0.5 mm and about 5 mm.

3. The filter probe of claim 1, wherein the hollow fibers of the fiber bundle have an average inner diameter in a range between about 0.1 mm and about 5 mm.

4. The filter probe of claim 1, wherein the hollow fibers of the fiber bundle are arranged in an array.

5. The filter probe of claim 4, wherein the array is a hexagonal, linear, annular, or square array.

6. The filter probe of claim 1, wherein the fiber bundle comprises at least about 10 hollow fibers.

7. The filter probe of claim 1, wherein the filter bundle comprises a structured segment over which the center-to-center distance between any two hollow fibers within the fiber bundle is greater than or equal to the average outer diameter of the hollow fibers of the fiber bundle.

8. The filter probe of claim 1, wherein the filter bundle comprises a structured segment over which the center-to-center distance between any two hollow fibers within the fiber bundle is greater than or equal to 1.1 times a minimum diameter of the two hollow fibers.

9. The filter probe of claim 8, wherein the structured segment has a length of at least about 50 mm.

10. The filter probe of claim 8, wherein the hollow fibers within the structured segment have a surface area of at least about 20 $cm^2$.

11. The filter probe of claim 1, wherein at least one hollow fiber within the fiber bundle comprises a plurality of pores having an average pore size as measured by porometry in a range between about 0.025 μm and about 2.0 μm.

12. The filter probe of claim 1, wherein one or more hollow fibers within the fiber bundle comprise a polymer, a ceramic, and/or a metal.

13. The filter probe of claim 1, wherein the filter probe is configured to withstand a pressure differential between about −5 bar and about 5 bar.

14. The filter probe of claim 1, wherein the plurality of hollow fibers has a variable alignment along a structured segment of the filter probe.

15. The filter probe of claim 1, wherein the filter probe comprises a central shaft and one or more spacing elements associated with the central shaft.

16. The filter probe of claim 15, wherein the one or more spacing elements encircle the central shaft.

17. The filter probe of claim 15, wherein the one or more spacing elements each include a central clearance hole through which the shaft is inserted.

18. The filter probe of claim 1, wherein the center-to-center distance between any two hollow fibers within the fiber bundle at one or more points along a length of the fiber bundle is greater than or equal to 2.5 times a minimum diameter of the two hollow fibers.

19. A filter probe, comprising:
a fiber bundle comprising a plurality of hollow fibers,
wherein a center-to-center distance between any two hollow fibers within the fiber bundle at one or more points along a length of the fiber bundle is greater than or equal to an average outer diameter of the hollow fibers of the fiber bundle,
wherein the filter probe has a diameter of about 25 mm or less and comprises 2500 or fewer fibers, and
wherein the filter probe is configured to be at least partially submerged in a liquid medium that is being filtered by the filter probe during operation.

20. A filter probe, comprising:
a fiber bundle comprising a plurality of hollow fibers; and
a secondary filter,
wherein at least one hollow fiber of the fiber bundle is fluidically connected to the secondary filter,
wherein the filter probe has a diameter of about 25 mm or less and comprises 2500 or fewer fibers, and
wherein the filter probe is configured to be at least partially submerged in a liquid medium that is being filtered by the filter probe during operation.

* * * * *